(12) United States Patent
Nelson et al.

(10) Patent No.: US 11,937,815 B2
(45) Date of Patent: *Mar. 26, 2024

(54) SURGICAL STAPLER HAVING A POWERED HANDLE

(71) Applicant: Applied Medical Resources Corporation, Rancho Santa Margarita, CA (US)

(72) Inventors: Erik D. Nelson, Santa Clara, CA (US); Jonathan R. Nash, Rancho Santa Margarita, CA (US); Timothy M. Hopkins, Rancho Santa Margarita, CA (US); Kevin Hudson, Rancho Santa Margarita, CA (US); Andy Pham, Rancho Santa Margarita, CA (US); Zachary W. Gyugyi, Rancho Santa Margarita, CA (US); Joshua A. Spalding, Los Angeles, CA (US); Christian A Halvorsen, Rancho Santa Margarita, CA (US)

(73) Assignee: Applied Medical Resources Corporation, Rancho Santa Margarita, CA (US)

(*) Notice: Subject to any disclaimer, the term of this patent is extended or adjusted under 35 U.S.C. 154(b) by 151 days.

This patent is subject to a terminal disclaimer.

(21) Appl. No.: 17/337,672

(22) Filed: Jun. 3, 2021

(65) Prior Publication Data

US 2021/0290234 A1    Sep. 23, 2021

Related U.S. Application Data

(63) Continuation of application No. 16/287,748, filed on Feb. 27, 2019, now Pat. No. 11,064,999.

(Continued)

(51) Int. Cl.
*A61B 17/072* (2006.01)
*A61B 17/00* (2006.01)
(Continued)

(52) U.S. Cl.
CPC ............... *A61B 17/07207* (2013.01); *A61B 2017/00017* (2013.01); *A61B 2017/00115* (2013.01);
(Continued)

(58) Field of Classification Search
CPC ................................ A61B 17/07207
See application file for complete search history.

(56) References Cited

U.S. PATENT DOCUMENTS 2,073,960 A    3/1937  Crosby
2,140,593 A   12/1938  Pankonin
(Continued)

FOREIGN PATENT DOCUMENTS

EP    0 251 444 A1    1/1988
EP    0 492 283 A1    7/1992
(Continued)

OTHER PUBLICATIONS

European Patent Office, The International Search Report and Written Opinion for International Application No. PCT/US2020/067540, dated May 3, 2021, entitled "Electrosurgical System with Tissue and Maximum Current Identification," 12 pages.
(Continued)

*Primary Examiner* — Anna K Kinsaul
*Assistant Examiner* — Lucas E. A. Palmer
(74) *Attorney, Agent, or Firm* — Thomas Nguyen; John Heal

(57) ABSTRACT

A powered handle for a surgical stapler can have a drive system including an electric motor. The powered handle can include a manual articulation mechanism to articulate a jaw
(Continued)

assembly coupled to a reload shaft connected to the handle. The manual articulation mechanism can include a ball screw mechanism that translates an articulation member responsive to rotation of an articulation knob when an instrument shaft is engaged with the handle. The articulation mechanism includes a release function that allows the jaw assembly to return to a longitudinally centered orientation. The powered handle includes a battery pack serving as a power supply for the drive system. A control system can control actuation of the motor based on user inputs and operating parameters of the stapler and can provide certain motor drive profiles for predetermined positions of the stapler. The powered handle can include a manual return mechanism.

15 Claims, 58 Drawing Sheets

Related U.S. Application Data

(60) Provisional application No. 62/734,154, filed on Sep. 20, 2018, provisional application No. 62/636,070, filed on Feb. 27, 2018.

(51) Int. Cl.
    *A61B 17/29*       (2006.01)
    *A61B 18/00*       (2006.01)
    *A61B 90/00*       (2016.01)

(52) U.S. Cl.
    CPC ................ *A61B 2017/0019* (2013.01); *A61B 2017/0023* (2013.01); *A61B 2017/00398* (2013.01); *A61B 2017/00407* (2013.01); *A61B 2017/0042* (2013.01); *A61B 2017/0046* (2013.01); *A61B 2017/00734* (2013.01); *A61B 2017/07271* (2013.01); *A61B 2017/07285* (2013.01); *A61B 2017/2923* (2013.01); *A61B 2017/2925* (2013.01); *A61B 2017/2927* (2013.01); *A61B 2017/2946* (2013.01); *A61B 2018/00297* (2013.01); *A61B 2090/064* (2016.02); *A61B 2090/0807* (2016.02); *A61B 2090/0811* (2016.02); *A61B 2090/0814* (2016.02)

(56) References Cited

U.S. PATENT DOCUMENTS

| | | |
|---|---|---|
| 2,351,608 A | 6/1944 | Greenwood |
| 2,487,565 A | 11/1949 | Leber et al. |
| 2,641,154 A | 6/1953 | Heller |
| 3,076,373 A | 2/1963 | Matthews |
| 3,077,812 A | 2/1963 | Dietrich |
| 3,080,564 A | 3/1963 | Strekopitov et al. |
| 3,203,220 A | 8/1965 | Kaepernik |
| 3,252,643 A | 5/1966 | Strekopitov et al. |
| 3,273,562 A | 9/1966 | Brown |
| 3,373,646 A | 3/1968 | Ehlert |
| 3,459,187 A | 8/1969 | Pallotta |
| 3,494,533 A | 2/1970 | Green et al. |
| 3,662,939 A | 5/1972 | Bryan |
| 3,675,688 A | 7/1972 | Bryan et al. |
| 3,692,224 A | 9/1972 | Astafiev et al. |
| 4,261,244 A | 4/1981 | Becht et al. |
| 4,281,785 A | 8/1981 | Brooks |
| 4,304,236 A | 12/1981 | Conta et al. |
| 4,312,363 A | 1/1982 | Rothfuss et al. |
| 4,317,451 A | 3/1982 | Cerwin et al. |
| 4,407,286 A | 10/1983 | Noiles et al. |
| 4,434,796 A | 3/1984 | Karapetian et al. |
| 4,442,964 A | 4/1984 | Becht |
| 4,454,875 A | 6/1984 | Pratt et al. |
| 4,522,327 A | 6/1985 | Korthoff et al. |
| 4,527,724 A | 7/1985 | Chow et al. |
| 4,589,582 A | 5/1986 | Bilotti |
| 4,591,085 A | 5/1986 | Di Giovanni |
| 4,606,344 A | 8/1986 | Di Giovanni |
| 4,608,981 A | 9/1986 | Rothfuss et al. |
| 4,610,383 A | 9/1986 | Rothfuss et al. |
| 4,728,020 A | 3/1988 | Green et al. |
| 4,805,823 A | 2/1989 | Rothfuss |
| 4,892,244 A | 1/1990 | Fox et al. |
| 4,923,350 A | 5/1990 | Hinksman et al. |
| 4,941,623 A | 7/1990 | Pruitt |
| 4,955,959 A | 9/1990 | Tompkins et al. |
| 4,978,049 A | 12/1990 | Green |
| 5,031,814 A | 7/1991 | Tompkins et al. |
| 5,065,929 A | 11/1991 | Schulze et al. |
| 5,071,052 A | 12/1991 | Rodak et al. |
| 5,106,008 A | 4/1992 | Tompkins et al. |
| 5,116,349 A | 5/1992 | Aranyi |
| 5,129,570 A | 7/1992 | Schulze et al. |
| 5,180,092 A | 1/1993 | Crainich |
| 5,201,746 A | 4/1993 | Shichman |
| 5,221,036 A | 6/1993 | Takase |
| 5,236,440 A | 8/1993 | Hlavacek |
| 5,240,163 A | 8/1993 | Stein et al. |
| RE34,519 E | 1/1994 | Fox et al. |
| 5,275,323 A | 1/1994 | Schulze et al. |
| 5,289,963 A | 3/1994 | McGarry et al. |
| D347,474 S | 5/1994 | Olson |
| 5,307,976 A | 5/1994 | Olson et al. |
| 5,308,576 A | 5/1994 | Green et al. |
| 5,326,013 A | 7/1994 | Green et al. |
| 5,350,400 A | 9/1994 | Esposito et al. |
| 5,360,305 A | 11/1994 | Kerrigan |
| 5,364,002 A | 11/1994 | Green et al. |
| 5,366,479 A | 11/1994 | McGarry et al. |
| 5,381,943 A | 1/1995 | Allen et al. |
| 5,389,098 A | 2/1995 | Tsuruta et al. |
| 5,395,034 A | 3/1995 | Allen et al. |
| 5,397,046 A | 3/1995 | Savage et al. |
| 5,413,267 A | 5/1995 | Solyntjes et al. |
| 5,415,334 A | 5/1995 | Williamson, IV et al. |
| 5,415,335 A | 5/1995 | Knodell, Jr. |
| 5,439,155 A | 8/1995 | Viola |
| 5,439,479 A | 8/1995 | Shichman et al. |
| 5,445,304 A | 8/1995 | Plyley et al. |
| 5,447,265 A | 9/1995 | Vidal et al. |
| 5,452,836 A | 9/1995 | Huitema et al. |
| 5,456,401 A | 10/1995 | Green et al. |
| 5,458,279 A | 10/1995 | Plyley |
| 5,462,215 A | 10/1995 | Viola et al. |
| 5,464,144 A | 11/1995 | Guy et al. |
| 5,465,895 A | 11/1995 | Knodel et al. |
| 5,470,006 A | 11/1995 | Rodak |
| 5,470,007 A | 11/1995 | Plyley et al. |
| 5,470,008 A | 11/1995 | Rodak |
| 5,470,009 A | 11/1995 | Rodak |
| 5,472,132 A | 12/1995 | Savage et al. |
| 5,480,089 A | 1/1996 | Blewett |
| 5,485,952 A | 1/1996 | Fontayne |
| 5,487,500 A | 1/1996 | Knodel et al. |
| 5,489,058 A | 2/1996 | Plyley |
| 5,497,933 A | 3/1996 | DeFonzo et al. |
| 5,507,426 A | 4/1996 | Young et al. |
| 5,507,773 A | 4/1996 | Huitema et al. |
| 5,509,596 A | 4/1996 | Green et al. |
| 5,509,920 A | 4/1996 | Phillips et al. |
| 5,529,235 A | 6/1996 | Boiarski et al. |
| 5,547,117 A | 8/1996 | Hamblin et al. |
| 5,553,765 A | 9/1996 | Knodel et al. |
| 5,554,164 A | 9/1996 | Wilson et al. |
| 5,558,266 A | 9/1996 | Green et al. |
| 5,562,241 A | 10/1996 | Knodel et al. |
| 5,562,700 A | 10/1996 | Huitema et al. |
| 5,562,701 A | 10/1996 | Huitema et al. |
| 5,562,702 A | 10/1996 | Huitema et al. |
| 5,564,615 A | 10/1996 | Bishop et al. |
| 5,571,115 A | 11/1996 | Nicholas |

(56) References Cited

U.S. PATENT DOCUMENTS

| | | | |
|---|---|---|---|
| 5,571,285 A | 11/1996 | Chow et al. |
| 5,579,978 A | 12/1996 | Green et al. |
| 5,580,067 A | 12/1996 | Hamblin et al. |
| 5,584,425 A | 12/1996 | Savage et al. |
| 5,586,711 A | 12/1996 | Plyley et al. |
| 5,588,581 A | 12/1996 | Conlon et al. |
| 5,597,107 A | 1/1997 | Knodel et al. |
| 5,601,224 A | 2/1997 | Bishop et al. |
| 5,605,272 A | 2/1997 | Witt et al. |
| 5,607,095 A | 3/1997 | Smith et al. |
| 5,615,820 A | 4/1997 | Viola |
| 5,626,587 A | 5/1997 | Bishop et al. |
| 5,630,539 A | 5/1997 | Plyley et al. |
| 5,634,584 A | 6/1997 | Okorocha et al. |
| 5,636,779 A | 6/1997 | Palmer |
| 5,657,921 A | 8/1997 | Young et al. |
| 5,662,258 A | 9/1997 | Knodel et al. |
| 5,662,662 A | 9/1997 | Bishop et al. |
| 5,662,667 A | 9/1997 | Knodel |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,678,748 A | 10/1997 | Plyley |
| 5,680,982 A | 10/1997 | Schulze et al. |
| 5,680,983 A | 10/1997 | Plyley et al. |
| 5,697,542 A | 12/1997 | Knodel et al. |
| 5,697,543 A | 12/1997 | Burdorff |
| 5,704,534 A | 1/1998 | Huitema et al. |
| 5,704,898 A | 1/1998 | Kokish |
| 5,706,998 A | 1/1998 | Blyley et al. |
| 5,709,334 A | 1/1998 | Sorrentino et al. |
| 5,713,505 A | 2/1998 | Huitema |
| 5,715,988 A | 2/1998 | Palmer |
| 5,718,359 A | 2/1998 | Palmer et al. |
| 5,732,871 A | 3/1998 | Clark et al. |
| 5,735,445 A | 4/1998 | Vidal et al. |
| 5,762,255 A | 6/1998 | Chrisman et al. |
| 5,762,256 A | 6/1998 | Mastri et al. |
| 5,779,130 A | 7/1998 | Alesi et al. |
| 5,782,396 A | 7/1998 | Mastri et al. |
| 5,782,397 A | 7/1998 | Koukline |
| 5,785,232 A | 7/1998 | Vidal et al. |
| 5,792,165 A * | 8/1998 | Klieman | A61B 34/71 606/174 |
| 5,794,834 A | 8/1998 | Hamblin et al. |
| 5,797,536 A | 8/1998 | Smith et al. |
| 5,797,537 A | 8/1998 | Oberlin et al. |
| 5,797,538 A | 8/1998 | Heaton et al. |
| 5,810,240 A | 9/1998 | Robertson |
| 5,814,055 A | 9/1998 | Knodel et al. |
| 5,817,119 A * | 10/1998 | Klieman | A61B 17/29 606/174 |
| 5,820,009 A | 10/1998 | Melling et al. |
| 5,829,662 A | 11/1998 | Allen et al. |
| 5,860,995 A | 1/1999 | Berkelaar |
| 5,865,361 A | 2/1999 | Milliman et al. |
| 5,878,937 A | 3/1999 | Green et al. |
| 5,878,938 A | 3/1999 | Bittner et al. |
| 5,893,506 A | 4/1999 | Powell |
| 5,894,979 A | 4/1999 | Powell |
| 5,901,895 A | 5/1999 | Heaton et al. |
| 5,918,791 A | 7/1999 | Sorrentino et al. |
| 5,931,847 A | 8/1999 | Bittner et al. |
| 5,954,259 A | 9/1999 | Viola et al. |
| 5,964,394 A | 10/1999 | Robertson |
| D416,089 S | 11/1999 | Barton et al. |
| 5,988,479 A | 11/1999 | Palmer |
| 6,032,849 A | 3/2000 | Mastri et al. |
| 6,053,390 A | 4/2000 | Green et al. |
| 6,079,606 A | 6/2000 | Milliman et al. |
| 6,109,500 A | 8/2000 | Alli et al. |
| 6,131,789 A | 10/2000 | Schulze et al. |
| 6,155,473 A | 12/2000 | Tompkins et al. |
| D441,865 S | 5/2001 | Racenet et al. |
| 6,241,139 B1 | 6/2001 | Milliman et al. |
| 6,250,532 B1 | 6/2001 | Green et al. |
| 6,264,087 B1 | 7/2001 | Whitman |
| 6,270,453 B1 | 8/2001 | Sakai |
| 6,325,810 B1 | 12/2001 | Hamilton et al. |
| 6,330,965 B1 | 12/2001 | Milliman et al. |
| 6,488,196 B1 | 12/2002 | Fenton, Jr. |
| 6,550,757 B2 | 4/2003 | Sesek |
| 6,569,171 B2 | 5/2003 | DeGuillebon et al. |
| 6,595,509 B2 | 7/2003 | Sesek |
| 6,619,529 B2 | 9/2003 | Green et al. |
| 6,644,532 B2 | 11/2003 | Green et al. |
| 6,669,073 B2 | 12/2003 | Milliman et al. |
| 6,716,233 B1 | 4/2004 | Whitman |
| 6,786,382 B1 | 9/2004 | Hoffman |
| 6,817,508 B1 | 11/2004 | Racenet et al. |
| 6,821,282 B2 | 11/2004 | Perry et al. |
| 6,835,199 B2 | 12/2004 | McGuckin, Jr. et al. |
| 6,913,181 B2 | 7/2005 | Mochizuki et al. |
| 6,923,360 B2 | 8/2005 | Sesek et al. |
| 6,953,138 B1 | 10/2005 | Dworak et al. |
| 6,953,139 B2 | 10/2005 | Milliman et al. |
| 6,964,363 B2 | 11/2005 | Wales et al. |
| 6,978,921 B2 | 12/2005 | Shelton, IV et al. |
| 6,986,451 B1 | 1/2006 | Mastri et al. |
| 6,988,649 B2 | 1/2006 | Shelton, IV et al. |
| 7,000,818 B2 | 2/2006 | Shelton, IV et al. |
| 7,044,352 B2 | 5/2006 | Shelton, IV et al. |
| 7,044,353 B2 | 5/2006 | Mastri et al. |
| 7,044,947 B2 | 5/2006 | de la Torre et al. |
| 7,055,730 B2 | 6/2006 | Ehrenfels et al. |
| 7,070,083 B2 | 7/2006 | Jankowski |
| 7,097,089 B2 | 8/2006 | Marczyk |
| 7,097,650 B2 | 8/2006 | Weller et al. |
| 7,108,472 B2 | 9/2006 | Norris et al. |
| 7,128,253 B2 | 10/2006 | Mastri et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,147,139 B2 | 12/2006 | Schwemberger et al. |
| 7,213,736 B2 | 5/2007 | Wales et al. |
| 7,225,964 B2 | 6/2007 | Mastri et al. |
| 7,237,708 B1 | 7/2007 | Guy et al. |
| 7,258,262 B2 | 8/2007 | Mastri et al. |
| 7,275,674 B2 | 10/2007 | Racenet et al. |
| 7,278,562 B2 | 10/2007 | Mastri et al. |
| 7,290,692 B2 | 11/2007 | Marks |
| 7,293,685 B2 | 11/2007 | Ehrenfels et al. |
| 7,303,107 B2 | 12/2007 | Milliman et al. |
| 7,308,998 B2 | 12/2007 | Mastri et al. |
| 7,328,828 B2 | 2/2008 | Ortiz et al. |
| 7,334,717 B2 | 2/2008 | Rethy et al. |
| 7,380,695 B2 | 6/2008 | Doll et al. |
| 7,380,696 B2 | 6/2008 | Shelton, IV et al. |
| 7,398,908 B2 | 7/2008 | Holsten et al. |
| 7,399,310 B2 | 7/2008 | Edoga et al. |
| 7,401,721 B2 | 7/2008 | Holsten et al. |
| 7,404,508 B2 | 7/2008 | Smith et al. |
| 7,407,075 B2 | 8/2008 | Holsten et al. |
| 7,407,078 B2 | 8/2008 | Shelton, IV et al. |
| 7,416,101 B2 | 8/2008 | Shelton, IV et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,434,715 B2 | 10/2008 | Shelton, IV et al. |
| 7,434,716 B2 | 10/2008 | Viola |
| 7,455,208 B2 | 11/2008 | Wales et al. |
| 7,455,676 B2 | 11/2008 | Holsten et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |

(56) References Cited

U.S. PATENT DOCUMENTS

| | | |
|---|---|---|
| 7,472,816 B2 | 1/2009 | Holsten et al. |
| 7,481,348 B2 | 1/2009 | Marczyk |
| 7,481,349 B2 | 1/2009 | Holsten et al. |
| 7,487,899 B2 | 2/2009 | Shelton, IV et al. |
| 7,490,749 B2 | 2/2009 | Schall et al. |
| 7,506,790 B2 | 3/2009 | Shelton, IV |
| 7,506,791 B2 | 3/2009 | Omaits et al. |
| 7,513,408 B2 | 4/2009 | Shelton, IV et al. |
| 7,530,484 B1 | 5/2009 | Durrani |
| 7,543,730 B1 | 6/2009 | Marczyk |
| 7,543,731 B2 | 6/2009 | Green et al. |
| 7,546,940 B2 | 6/2009 | Milliman et al. |
| 7,549,564 B2 | 6/2009 | Boudreaux |
| 7,552,854 B2 | 6/2009 | Wixey et al. |
| 7,556,186 B2 | 7/2009 | Milliman |
| 7,565,993 B2 | 7/2009 | Milliman et al. |
| 7,568,604 B2 | 8/2009 | Ehrenfels et al. |
| 7,588,174 B2 | 9/2009 | Holsten et al. |
| 7,588,175 B2 | 9/2009 | Timm et al. |
| 7,588,177 B2 | 9/2009 | Racenet |
| 7,604,151 B2 | 10/2009 | Hess et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,631,793 B2 | 12/2009 | Rethy et al. |
| 7,635,074 B2 | 12/2009 | Olson et al. |
| 7,637,409 B2 | 12/2009 | Marczyk |
| 7,637,410 B2 | 12/2009 | Marczyk |
| 7,641,091 B2 | 1/2010 | Olson et al. |
| 7,641,093 B2 | 1/2010 | Doll et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,781 B2 | 3/2010 | Swayze et al. |
| 7,682,367 B2 | 3/2010 | Shah et al. |
| 7,690,547 B2 | 4/2010 | Racenet et al. |
| 7,703,653 B2 | 4/2010 | Shah et al. |
| 7,717,312 B2 | 5/2010 | Beetel |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,721,936 B2 | 5/2010 | Shelton, IV et al. |
| 7,726,538 B2 | 6/2010 | Holsten et al. |
| 7,726,539 B2 | 6/2010 | Holsten et al. |
| 7,731,073 B2 | 6/2010 | Wixey et al. |
| 7,735,703 B2 | 6/2010 | Morgan et al. |
| 7,753,245 B2 | 7/2010 | Boudreaux et al. |
| 7,753,246 B2 | 7/2010 | Scirica |
| 7,757,925 B2 | 7/2010 | Viola et al. |
| 7,766,210 B2 | 8/2010 | Shelton, IV et al. |
| 7,770,774 B2 | 8/2010 | Mastri et al. |
| 7,780,054 B2 | 8/2010 | Wales |
| 7,780,055 B2 | 8/2010 | Scirica et al. |
| 7,784,662 B2 | 8/2010 | Wales et al. |
| 7,784,663 B2 | 8/2010 | Shelton, IV |
| 7,793,812 B2 | 9/2010 | Moore et al. |
| 7,798,386 B2 | 9/2010 | Schall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,819,298 B2 | 10/2010 | Hall et al. |
| 7,819,896 B2 | 10/2010 | Racenet |
| 7,823,760 B2 | 11/2010 | Zemlok et al. |
| 7,828,188 B2 | 11/2010 | Jankowski |
| 7,828,189 B2 | 11/2010 | Holsten et al. |
| 7,837,079 B2 | 11/2010 | Holsten et al. |
| 7,837,081 B2 | 11/2010 | Holsten et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,857,184 B2 | 12/2010 | Viola |
| 7,857,185 B2 | 12/2010 | Swayze et al. |
| 7,857,187 B2 | 12/2010 | Milliman |
| 7,861,906 B2 | 1/2011 | Doll et al. |
| 7,866,525 B2 | 1/2011 | Scirica |
| 7,866,527 B2 | 1/2011 | Hall et al. |
| 7,891,534 B2 | 2/2011 | Wenchell et al. |
| 7,905,381 B2 | 3/2011 | Baxter, III et al. |
| 7,909,220 B2 | 3/2011 | Viola |
| 7,909,221 B2 | 3/2011 | Viola et al. |
| 7,913,891 B2 | 3/2011 | Doll et al. |
| 7,914,543 B2 | 3/2011 | Roth et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,922,063 B2 | 4/2011 | Zemlok et al. |
| 7,934,628 B2 | 5/2011 | Wenchell et al. |
| 7,934,629 B2 | 5/2011 | Wixey et al. |
| 7,934,630 B2 | 5/2011 | Shelton, IV et al. |
| 7,942,300 B2 | 5/2011 | Rethy et al. |
| 7,954,685 B2 | 6/2011 | Viola |
| 7,954,686 B2 | 6/2011 | Baxter, III et al. |
| 7,959,050 B2 | 6/2011 | Smith et al. |
| 7,963,433 B2 | 6/2011 | Whitman et al. |
| 7,992,758 B2 | 8/2011 | Whitman et al. |
| 8,002,795 B2 | 8/2011 | Beetel |
| 8,006,887 B2 | 8/2011 | Marczyk |
| 8,007,513 B2 | 8/2011 | Nalagatla et al. |
| 8,008,598 B2 | 8/2011 | Whitman et al. |
| 8,011,550 B2 | 9/2011 | Aranyi et al. |
| 8,011,553 B2 | 9/2011 | Mastri et al. |
| 8,012,170 B2 | 9/2011 | Whitman et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,885 B2 | 10/2011 | Smith et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,046 B2 | 10/2011 | Smith et al. |
| 8,052,024 B2 | 11/2011 | Viola et al. |
| 8,056,788 B2 | 11/2011 | Mastri et al. |
| 8,056,789 B1 | 11/2011 | White et al. |
| 8,061,576 B2 | 11/2011 | Cappola |
| 8,061,577 B2 | 11/2011 | Racenet et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,070,036 B1 | 12/2011 | Knodel |
| 8,074,861 B2 | 12/2011 | Ehrenfels et al. |
| 8,083,118 B2 | 12/2011 | Milliman et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,092,493 B2 | 1/2012 | Marczyk |
| 8,100,309 B2 | 1/2012 | Marczyk |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,410 B2 | 2/2012 | Hall et al. |
| 8,118,207 B2 | 2/2012 | Racenet et al. |
| 8,123,100 B2 | 2/2012 | Holsten et al. |
| 8,127,976 B2 | 3/2012 | Scirica et al. |
| 8,136,712 B2 | 3/2012 | Zingman |
| 8,152,041 B2 | 4/2012 | Kostrzewski |
| 8,157,145 B2 | 4/2012 | Shelton, IV et al. |
| 8,157,150 B2 | 4/2012 | Viola et al. |
| 8,157,152 B2 | 4/2012 | Holsten et al. |
| 8,181,839 B2 | 5/2012 | Beetel |
| 8,186,555 B2 | 5/2012 | Shelton, IV et al. |
| 8,186,556 B2 | 5/2012 | Viola |
| 8,186,560 B2 | 5/2012 | Hess et al. |
| 8,191,752 B2 | 6/2012 | Scirica |
| 8,196,795 B2 | 6/2012 | Moore et al. |
| 8,201,721 B2 | 6/2012 | Zemlok et al. |
| 8,205,619 B2 | 6/2012 | Shah et al. |

(56) References Cited

U.S. PATENT DOCUMENTS

| | | |
|---|---|---|
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,416 B2 | 7/2012 | Milliman et al. |
| 8,220,688 B2 | 7/2012 | Laurent et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,256,656 B2 | 9/2012 | Milliman et al. |
| 8,272,552 B2 | 9/2012 | Holsten et al. |
| 8,272,554 B2 | 9/2012 | Whitman et al. |
| 8,281,972 B2 | 10/2012 | Wixey et al. |
| 8,281,973 B2 | 10/2012 | Wenchell et al. |
| 8,286,846 B2 | 10/2012 | Smith et al. |
| 8,292,146 B2 | 10/2012 | Holsten et al. |
| 8,292,148 B2 | 10/2012 | Viola |
| 8,292,151 B2 | 10/2012 | Viola |
| 8,292,152 B2 | 10/2012 | Milliman et al. |
| 8,292,153 B2 | 10/2012 | Jankowski |
| 8,292,157 B2 | 10/2012 | Smith et al. |
| 8,308,041 B2 | 11/2012 | Kostrzewski |
| 8,308,043 B2 | 11/2012 | Bindra et al. |
| 8,317,070 B2 | 11/2012 | Hueil et al. |
| 8,322,455 B2 | 12/2012 | Shelton, IV et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,125 B2 | 1/2013 | Viola et al. |
| 8,348,129 B2 | 1/2013 | Bedi et al. |
| 8,348,131 B2 | 1/2013 | Omaits et al. |
| 8,353,440 B2 | 1/2013 | Whitman et al. |
| 8,360,297 B2 | 1/2013 | Shelton, IV et al. |
| 8,360,299 B2 | 1/2013 | Zemlok et al. |
| 8,393,513 B2 | 3/2013 | Jankowski |
| 8,397,972 B2 | 3/2013 | Kostrzewski |
| 8,397,973 B1 | 3/2013 | Hausen |
| 8,403,198 B2 | 3/2013 | Sorrentino et al. |
| 8,413,868 B2 | 4/2013 | Cappola |
| 8,414,577 B2 | 4/2013 | Boudreaux et al. |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,439,246 B1 | 5/2013 | Knodel |
| 8,444,036 B2 | 5/2013 | Shelton, IV |
| 8,453,907 B2 | 6/2013 | Laurent et al. |
| 8,453,912 B2 | 6/2013 | Mastri et al. |
| 8,453,913 B2 | 6/2013 | Milliman |
| 8,459,520 B2 | 6/2013 | Giordano et al. |
| 8,459,522 B2 | 6/2013 | Marczyk |
| 8,464,922 B2 | 6/2013 | Marczyk |
| 8,469,252 B2 | 6/2013 | Holcomb et al. |
| 8,479,967 B2 | 7/2013 | Marczyk |
| 8,496,152 B2 | 7/2013 | Viola |
| 8,496,155 B2 | 7/2013 | Knodel |
| 8,496,156 B2 | 7/2013 | Sniffin et al. |
| 8,496,683 B2 | 7/2013 | Prommersberger et al. |
| 8,505,799 B2 | 8/2013 | Viola et al. |
| 8,505,801 B2 | 8/2013 | Ehrenfels et al. |
| 8,517,239 B2 | 8/2013 | Scheib et al. |
| 8,517,240 B1 | 8/2013 | Mata et al. |
| 8,523,043 B2 | 9/2013 | Ullrich et al. |
| 8,540,130 B2 | 9/2013 | Moore et al. |
| 8,540,133 B2 | 9/2013 | Bedi et al. |
| 8,540,625 B2 | 9/2013 | Miyoshi |
| 8,544,712 B2 | 10/2013 | Jankowski |
| 8,556,151 B2 | 10/2013 | Viola |
| 8,556,152 B2 | 10/2013 | Marczyk et al. |
| 8,556,153 B1 | 10/2013 | Knodel |
| 8,561,871 B2 | 10/2013 | Rajappa et al. |
| 8,561,874 B2 | 10/2013 | Scirica |
| 8,573,459 B2 | 11/2013 | Smith et al. |
| 8,573,460 B2 | 11/2013 | Cappola |
| 8,573,462 B2 | 11/2013 | Smith et al. |
| 8,573,463 B2 | 11/2013 | Scirica et al. |
| 8,573,464 B2 | 11/2013 | Nalagatla et al. |
| 8,579,176 B2 | 11/2013 | Smith et al. |
| 8,579,177 B2 | 11/2013 | Beetel |
| 8,584,919 B2 | 11/2013 | Hueil et al. |
| 8,584,921 B2 | 11/2013 | Scirica |
| 8,596,513 B2 | 12/2013 | Olson |
| 8,608,043 B2 | 12/2013 | Scirica |
| 8,608,045 B2 | 12/2013 | Smith et al. |
| 8,616,427 B2 | 12/2013 | Viola |
| 8,622,274 B2 | 1/2014 | Yates et al. |
| 8,627,992 B2 | 1/2014 | Edoga et al. |
| 8,627,993 B2 | 1/2014 | Smith et al. |
| 8,627,995 B2 | 1/2014 | Smith et al. |
| 8,631,990 B1 | 1/2014 | Park et al. |
| 8,632,525 B2 | 1/2014 | Kerr et al. |
| 8,632,535 B2 | 1/2014 | Shelton, IV et al. |
| 8,636,189 B1 | 1/2014 | Knodel et al. |
| 8,636,190 B2 | 1/2014 | Zemlok et al. |
| 8,636,192 B2 | 1/2014 | Farascioni et al. |
| 8,636,193 B2 | 1/2014 | Whitman et al. |
| 8,636,762 B2 | 1/2014 | Whitman et al. |
| 8,636,766 B2 | 1/2014 | Milliman et al. |
| 8,657,174 B2 | 2/2014 | Yates et al. |
| 8,657,176 B2 | 2/2014 | Shelton, IV et al. |
| 8,657,178 B2 | 2/2014 | Hueil et al. |
| 8,672,209 B2 | 3/2014 | Crainich |
| 8,672,951 B2 | 3/2014 | Smith et al. |
| 8,685,004 B2 | 4/2014 | Zemlock et al. |
| 8,695,865 B2 | 4/2014 | Smith et al. |
| 8,696,665 B2 | 4/2014 | Hunt et al. |
| 8,708,211 B2 | 4/2014 | Zemlok et al. |
| 8,708,213 B2 | 4/2014 | Shelton, IV et al. |
| 8,740,034 B2 | 6/2014 | Morgan et al. |
| 8,740,035 B2 | 6/2014 | Mastri et al. |
| 8,740,036 B2 | 6/2014 | Williams |
| 8,752,748 B2 | 6/2014 | Whitman et al. |
| 8,763,876 B2 | 7/2014 | Kostrzewski |
| 8,770,458 B2 | 7/2014 | Scirica |
| 8,770,459 B2 | 7/2014 | Racenet et al. |
| 8,789,741 B2 | 7/2014 | Baxter, III et al. |
| 8,800,839 B2 | 8/2014 | Beetel |
| 8,800,840 B2 | 8/2014 | Jankowski |
| 8,800,841 B2 | 8/2014 | Ellerhorst et al. |
| 8,806,973 B2 | 8/2014 | Ross et al. |
| 8,807,414 B2 | 8/2014 | Ross et al. |
| 8,820,603 B2 | 9/2014 | Shelton, IV et al. |
| 8,820,608 B2 | 9/2014 | Miyamoto |
| 8,833,631 B2 | 9/2014 | Munro, III et al. |
| 8,840,003 B2 | 9/2014 | Morgan et al. |
| 8,858,571 B2 | 10/2014 | Shelton, IV et al. |
| 8,875,971 B2 | 11/2014 | Hall et al. |
| 8,875,972 B2 | 11/2014 | Weisenburgh, II et al. |
| 8,887,979 B2 | 11/2014 | Mastri et al. |
| 8,899,462 B2 | 12/2014 | Kostrzewski et al. |
| 8,899,463 B2 | 12/2014 | Schall et al. |
| 8,905,288 B2 | 12/2014 | Wenchell |
| 8,920,435 B2 | 12/2014 | Smith et al. |
| 8,925,783 B2 | 1/2015 | Zemlok et al. |
| 8,931,679 B2 | 1/2015 | Kostrzewski |
| 8,931,683 B2 | 1/2015 | Racenet et al. |
| 8,939,343 B2 | 1/2015 | Milliman et al. |
| 8,967,444 B2 | 3/2015 | Beetel |
| 8,967,446 B2 | 3/2015 | Beardsley et al. |
| 8,967,447 B2 | 3/2015 | Hartoumbekis |
| 8,968,276 B2 | 3/2015 | Zemlok et al. |
| 8,973,803 B2 | 3/2015 | Hall et al. |
| 8,979,827 B2 | 3/2015 | Cappola |
| 9,002,518 B2 * | 4/2015 | Manzo .............. A61B 90/98 901/19 |

(56) References Cited

U.S. PATENT DOCUMENTS

| | | |
|---|---|---|
| 9,004,340 B2 | 4/2015 | Scirica |
| 9,010,611 B2 | 4/2015 | Ross et al. |
| 9,016,541 B2 | 4/2015 | Viola et al. |
| 9,016,545 B2 | 4/2015 | Aranyi et al. |
| 9,022,271 B2 | 5/2015 | Scirica |
| 9,023,014 B2 | 5/2015 | Chowaniec et al. |
| 9,027,817 B2 | 5/2015 | Milliman et al. |
| 9,027,818 B2 | 5/2015 | Scirica et al. |
| 9,033,202 B2 | 5/2015 | Scirica |
| 9,038,880 B1 | 5/2015 | Donohoe |
| 9,055,943 B2 | 6/2015 | Zemlok et al. |
| 9,072,515 B2 | 7/2015 | Hall et al. |
| 9,084,601 B2 | 7/2015 | Moore et al. |
| 9,101,358 B2 | 8/2015 | Kerr et al. |
| 9,161,813 B2 | 10/2015 | Benamou |
| 9,204,876 B2 | 12/2015 | Cappola et al. |
| 9,237,890 B2 | 1/2016 | Kostrzewski |
| 9,265,585 B2 | 2/2016 | Wingardner et al. |
| 9,282,966 B2 | 3/2016 | Shelton, IV et al. |
| 9,386,984 B2 | 7/2016 | Aronhalt et al. |
| 9,402,629 B2 | 8/2016 | Ehrenfels et al. |
| 9,510,830 B2 | 12/2016 | Shelton, IV et al. |
| 9,532,782 B2 | 1/2017 | Kostrzewski |
| 9,662,108 B2 | 5/2017 | Williams |
| 9,737,302 B2 | 8/2017 | Shelton, IV et al. |
| 9,737,303 B2 | 8/2017 | Shelton, IV et al. |
| 9,797,486 B2 | 10/2017 | Zergiebel et al. |
| 10,918,386 B2 * | 2/2021 | Shelton, IV ... A61B 17/320092 |
| 2002/0025243 A1 | 2/2002 | Heck |
| 2002/0029044 A1 | 3/2002 | Monassevitch et al. |
| 2002/0062136 A1 | 5/2002 | Hillstead |
| 2002/0120279 A1 | 8/2002 | Deguillebon et al. |
| 2003/0130677 A1 | 7/2003 | Whitman et al. |
| 2004/0006372 A1 | 1/2004 | Racenet et al. |
| 2004/0138705 A1 | 7/2004 | Heino et al. |
| 2005/0234478 A1 | 10/2005 | Wixey |
| 2006/0097026 A1 | 5/2006 | Shelton, IV |
| 2006/0100644 A1 | 5/2006 | Viola |
| 2006/0180634 A1 | 8/2006 | Shelton, IV et al. |
| 2006/0235442 A1 | 10/2006 | Huitema |
| 2006/0289602 A1 | 12/2006 | Wales et al. |
| 2007/0034664 A1 | 2/2007 | Jiang |
| 2007/0039997 A1 | 2/2007 | Mather et al. |
| 2007/0057014 A1 | 3/2007 | Whitman et al. |
| 2007/0068990 A1 | 3/2007 | Shelton, IV et al. |
| 2007/0084897 A1 | 4/2007 | Shelton, IV et al. |
| 2007/0102472 A1 | 5/2007 | Shelton, IV |
| 2007/0119901 A1 | 5/2007 | Ehrenfels et al. |
| 2007/0131732 A1 | 6/2007 | Holsten et al. |
| 2007/0175950 A1 | 8/2007 | Shelton, IV et al. |
| 2007/0175951 A1 | 8/2007 | Shelton, IV et al. |
| 2008/0029574 A1 | 2/2008 | Shelton et al. |
| 2008/0029575 A1 | 2/2008 | Shelton et al. |
| 2008/0041918 A1 | 2/2008 | Holsten et al. |
| 2008/0078807 A1 | 4/2008 | Hess et al. |
| 2008/0083807 A1 | 4/2008 | Beardsley et al. |
| 2008/0169333 A1 | 7/2008 | Shelton et al. |
| 2008/0179375 A1 | 7/2008 | Scirica |
| 2008/0255607 A1 | 10/2008 | Zemlok |
| 2009/0001129 A1 * | 1/2009 | Marczyk ............ A61B 17/068<br>227/179.1 |
| 2009/0001130 A1 | 1/2009 | Hess et al. |
| 2009/0026245 A1 | 1/2009 | Holsten et al. |
| 2009/0048589 A1 | 2/2009 | Takashino et al. |
| 2009/0057369 A1 | 3/2009 | Smith et al. |
| 2009/0090763 A1 | 4/2009 | Zemlok et al. |
| 2009/0143806 A1 | 6/2009 | Witt et al. |
| 2009/0198272 A1 | 8/2009 | Kerver et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0277948 A1 | 11/2009 | Beardsley et al. |
| 2009/0277949 A1 | 11/2009 | Viola et al. |
| 2010/0069942 A1 | 3/2010 | Shelton, IV |
| 2010/0072258 A1 | 3/2010 | Farascioni et al. |
| 2010/0089970 A1 | 4/2010 | Smith et al. |
| 2010/0193566 A1 | 8/2010 | Scheib et al. |
| 2010/0230465 A1 | 9/2010 | Smith et al. |
| 2010/0331820 A1 | 12/2010 | Prisco et al. |
| 2011/0036892 A1 | 2/2011 | Marczyk et al. |
| 2011/0042440 A1 | 2/2011 | Holsten et al. |
| 2011/0087276 A1 | 4/2011 | Bedi et al. |
| 2011/0108601 A1 | 5/2011 | Clark et al. |
| 2011/0108603 A1 | 5/2011 | Racenet et al. |
| 2011/0121049 A1 | 5/2011 | Malinouskas et al. |
| 2011/0125138 A1 | 5/2011 | Malinouskas et al. |
| 2011/0127185 A1 | 6/2011 | Ward |
| 2011/0139851 A1 * | 6/2011 | McCuen .......... A61B 17/07207<br>227/175.1 |
| 2011/0139852 A1 | 6/2011 | Zingman |
| 2011/0147433 A1 | 6/2011 | Shelton, IV et al. |
| 2011/0155784 A1 | 6/2011 | Shelton, IV et al. |
| 2011/0155787 A1 | 6/2011 | Baxter, III et al. |
| 2011/0163985 A1 * | 7/2011 | Bae .................. G06F 3/016<br>345/173 |
| 2011/0290851 A1 | 12/2011 | Shelton, IV et al. |
| 2011/0290853 A1 | 12/2011 | Shelton, IV et al. |
| 2012/0061446 A1 | 3/2012 | Knodel et al. |
| 2012/0074198 A1 | 3/2012 | Huitema et al. |
| 2012/0074200 A1 | 3/2012 | Schmid et al. |
| 2012/0078243 A1 * | 3/2012 | Worrell ............ A61B 17/07207<br>606/130 |
| 2012/0080482 A1 | 4/2012 | Schall et al. |
| 2012/0080498 A1 | 4/2012 | Shelton, IV et al. |
| 2012/0091182 A1 | 4/2012 | Marczyk |
| 2012/0109186 A1 | 5/2012 | Parrott et al. |
| 2012/0168487 A1 | 7/2012 | Holsten et al. |
| 2012/0193396 A1 | 8/2012 | Zemlok et al. |
| 2012/0203247 A1 | 8/2012 | Shelton, IV et al. |
| 2012/0211542 A1 | 8/2012 | Racenet |
| 2012/0239009 A1 | 9/2012 | Mollere et al. |
| 2012/0253298 A1 | 10/2012 | Henderson et al. |
| 2012/0286022 A1 | 11/2012 | Olson et al. |
| 2012/0318844 A1 | 12/2012 | Shelton, IV et al. |
| 2012/0325893 A1 | 12/2012 | Pastorelli et al. |
| 2013/0001270 A1 | 1/2013 | Kostrzewski |
| 2013/0012958 A1 | 1/2013 | Marczyk et al. |
| 2013/0015229 A1 | 1/2013 | Viola |
| 2013/0015230 A1 | 1/2013 | Wixey et al. |
| 2013/0015232 A1 | 1/2013 | Smith et al. |
| 2013/0015233 A1 | 1/2013 | Viola |
| 2013/0020375 A1 | 1/2013 | Shelton, IV et al. |
| 2013/0030428 A1 * | 1/2013 | Worrell ................ A61B 5/0205<br>606/208 |
| 2013/0037595 A1 | 2/2013 | Gupta et al. |
| 2013/0048697 A1 | 2/2013 | Shelton, IV et al. |
| 2013/0056521 A1 | 3/2013 | Swensgard |
| 2013/0079814 A1 | 3/2013 | Hess et al. |
| 2013/0087603 A1 | 4/2013 | Viola |
| 2013/0092717 A1 | 4/2013 | Marczyk et al. |
| 2013/0098964 A1 | 4/2013 | Smith et al. |
| 2013/0098965 A1 | 4/2013 | Kostrzewski et al. |
| 2013/0098969 A1 | 4/2013 | Scirica et al. |
| 2013/0105545 A1 | 5/2013 | Burbank |
| 2013/0105547 A1 | 5/2013 | Beardsley |
| 2013/0105548 A1 | 5/2013 | Hodgkinson et al. |
| 2013/0105549 A1 | 5/2013 | Holsten et al. |
| 2013/0112730 A1 | 5/2013 | Whitman et al. |
| 2013/0112731 A1 | 5/2013 | Hodgkinson |
| 2013/0116668 A1 * | 5/2013 | Shelton, IV ......... A61B 17/072<br>606/1 |
| 2013/0126583 A1 | 5/2013 | Hueil et al. |
| 2013/0126586 A1 | 5/2013 | Zhang et al. |
| 2013/0146640 A1 | 6/2013 | Jankowski |
| 2013/0172928 A1 | 7/2013 | Kostrzewski |
| 2013/0172929 A1 | 7/2013 | Hess et al. |
| 2013/0175317 A1 | 7/2013 | Yates et al. |
| 2013/0175322 A1 | 7/2013 | Yates et al. |
| 2013/0184718 A1 | 7/2013 | Smith et al. |
| 2013/0186931 A1 | 7/2013 | Beardsley |
| 2013/0186932 A1 | 7/2013 | Shelton, IV et al. |
| 2013/0186933 A1 | 7/2013 | Shelton, IV et al. |
| 2013/0193188 A1 | 8/2013 | Shelton, IV et al. |
| 2013/0200132 A1 | 8/2013 | Moore et al. |

(56) References Cited

U.S. PATENT DOCUMENTS

| | | |
|---|---|---|
| 2013/0206816 A1 | 8/2013 | Penna |
| 2013/0214025 A1 | 8/2013 | Zemlok et al. |
| 2013/0221065 A1 | 8/2013 | Aronhalt et al. |
| 2013/0240604 A1 | 9/2013 | Knodel |
| 2013/0248582 A1 | 9/2013 | Scirica |
| 2013/0256370 A1 | 10/2013 | Smith et al. |
| 2013/0256371 A1 | 10/2013 | Shelton, IV |
| 2013/0270321 A1 | 10/2013 | Marczyk |
| 2013/0270323 A1 | 10/2013 | Marczyk |
| 2013/0284789 A1 | 10/2013 | Smith et al. |
| 2013/0284791 A1 | 10/2013 | Olson et al. |
| 2013/0299552 A1 | 11/2013 | Viola |
| 2013/0306702 A1 | 11/2013 | Viola et al. |
| 2013/0306703 A1 | 11/2013 | Ehrenfels et al. |
| 2013/0306706 A1 | 11/2013 | Knodel |
| 2013/0313303 A1 | 11/2013 | Shelton, IV et al. |
| 2013/0327809 A1 | 12/2013 | Shelton, IV et al. |
| 2013/0327810 A1 | 12/2013 | Swayze et al. |
| 2013/0334278 A1 | 12/2013 | Kerr et al. |
| 2013/0334280 A1 | 12/2013 | Krehel et al. |
| 2013/0334281 A1 | 12/2013 | Williams |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0334286 A1 | 12/2013 | Swayze et al. |
| 2013/0334287 A1 | 12/2013 | Shelton, IV |
| 2013/0334288 A1 | 12/2013 | Shelton, IV |
| 2014/0014704 A1 | 1/2014 | Onukuri et al. |
| 2014/0014707 A1 | 1/2014 | Onukuri et al. |
| 2014/0021239 A1 | 1/2014 | Kostrzewski |
| 2014/0025046 A1 | 1/2014 | Williams et al. |
| 2014/0027491 A1 | 1/2014 | Beardsley et al. |
| 2014/0027493 A1 | 1/2014 | Jankowski |
| 2014/0042204 A1 | 2/2014 | Beetel |
| 2014/0103092 A1 | 4/2014 | Kostrzewski et al. |
| 2014/0103093 A1 | 4/2014 | Koch, Jr. et al. |
| 2014/0107640 A1 | 4/2014 | Yates et al. |
| 2014/0110453 A1* | 4/2014 | Wingardner ............ G05B 9/02 227/175.2 |
| 2014/0131416 A1 | 5/2014 | Whitman et al. |
| 2014/0135832 A1 | 5/2014 | Park et al. |
| 2014/0151433 A1 | 6/2014 | Shelton, IV et al. |
| 2014/0151434 A1 | 6/2014 | Shelton, IV et al. |
| 2014/0158746 A1 | 6/2014 | Mastri et al. |
| 2014/0166727 A1 | 6/2014 | Swayze et al. |
| 2014/0175146 A1 | 6/2014 | Knodel |
| 2014/0175149 A1 | 6/2014 | Smith et al. |
| 2014/0203063 A1 | 7/2014 | Hessler et al. |
| 2014/0205637 A1 | 7/2014 | Widenhouse et al. |
| 2014/0224856 A1 | 8/2014 | Smith et al. |
| 2014/0236173 A1 | 8/2014 | Scirica et al. |
| 2014/0236184 A1 | 8/2014 | Leimbach |
| 2014/0239038 A1 | 8/2014 | Leimbach et al. |
| 2014/0239041 A1 | 8/2014 | Zerkle et al. |
| 2014/0239044 A1 | 8/2014 | Hoffman |
| 2014/0246474 A1 | 9/2014 | Hall et al. |
| 2014/0246475 A1 | 9/2014 | Hall et al. |
| 2014/0246478 A1 | 9/2014 | Baber et al. |
| 2014/0246479 A1 | 9/2014 | Baber et al. |
| 2014/0260746 A1 | 9/2014 | Sakaguchi et al. |
| 2014/0263537 A1 | 9/2014 | Leimbach et al. |
| 2014/0263539 A1 | 9/2014 | Leimbach et al. |
| 2014/0263541 A1 | 9/2014 | Leimbach et al. |
| 2014/0263542 A1 | 9/2014 | Leimbach et al. |
| 2014/0263543 A1 | 9/2014 | Leimbach et al. |
| 2014/0263545 A1 | 9/2014 | Williams et al. |
| 2014/0263546 A1 | 9/2014 | Aranyi |
| 2014/0263550 A1 | 9/2014 | Aranyi et al. |
| 2014/0263553 A1* | 9/2014 | Leimbach ............ A61B 17/072 227/176.1 |
| 2014/0263554 A1 | 9/2014 | Leimbach et al. |
| 2014/0263555 A1 | 9/2014 | Hufnagel et al. |
| 2014/0263559 A1 | 9/2014 | Williams et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263567 A1 | 9/2014 | Williams et al. |
| 2014/0263568 A1 | 9/2014 | Williams et al. |
| 2014/0263569 A1 | 9/2014 | Williams et al. |
| 2014/0263570 A1 | 9/2014 | Hopkins et al. |
| 2014/0263571 A1 | 9/2014 | Morgan et al. |
| 2014/0263572 A1 | 9/2014 | Shelton, IV et al. |
| 2014/0284372 A1 | 9/2014 | Kostrzewski |
| 2014/0291378 A1* | 10/2014 | Shelton, IV ...... A61B 17/07207 227/175.2 |
| 2014/0299649 A1 | 10/2014 | Shelton, IV et al. |
| 2014/0305986 A1 | 10/2014 | Hall et al. |
| 2014/0305988 A1 | 10/2014 | Boudreaux et al. |
| 2014/0305992 A1 | 10/2014 | Kimsey et al. |
| 2014/0305994 A1 | 10/2014 | Parihar et al. |
| 2014/0353359 A1 | 12/2014 | Hall et al. |
| 2015/0008248 A1 | 1/2015 | Giordano et al. |
| 2015/0034697 A1 | 2/2015 | Mastri et al. |
| 2015/0041518 A1 | 2/2015 | Shelton, IV et al. |
| 2015/0053738 A1 | 2/2015 | Morgan et al. |
| 2015/0053740 A1 | 2/2015 | Shelton, IV |
| 2015/0053741 A1 | 2/2015 | Shelton, IV et al. |
| 2015/0053742 A1 | 2/2015 | Shelton, IV et al. |
| 2015/0053743 A1 | 2/2015 | Yates et al. |
| 2015/0053744 A1 | 2/2015 | Swayze et al. |
| 2015/0053745 A1 | 2/2015 | Yates et al. |
| 2015/0053746 A1 | 2/2015 | Shelton, IV et al. |
| 2015/0053748 A1 | 2/2015 | Yates et al. |
| 2015/0053749 A1 | 2/2015 | Shelton, IV et al. |
| 2015/0054753 A1 | 2/2015 | Morgan et al. |
| 2015/0060516 A1 | 3/2015 | Collings et al. |
| 2015/0060517 A1 | 3/2015 | Williams |
| 2015/0060521 A1 | 3/2015 | Weisenburgh, II et al. |
| 2015/0076205 A1 | 3/2015 | Zergiebel |
| 2015/0076206 A1* | 3/2015 | Sapre ............... A61B 17/07207 227/175.2 |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0083781 A1 | 3/2015 | Giordano et al. |
| 2015/0083783 A1 | 3/2015 | Shelton, IV et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0090764 A1 | 4/2015 | Zemlok et al. |
| 2015/0108201 A1 | 4/2015 | Williams |
| 2015/0122872 A1 | 5/2015 | Olson et al. |
| 2015/0127046 A1 | 5/2015 | Peterson |
| 2015/0129631 A1 | 5/2015 | Beetel |
| 2015/0129634 A1 | 5/2015 | Shelton, IV et al. |
| 2015/0133995 A1 | 5/2015 | Shelton, IV et al. |
| 2015/0133996 A1 | 5/2015 | Shelton, IV et al. |
| 2015/0134076 A1 | 5/2015 | Shelton, IV et al. |
| 2015/0144678 A1 | 5/2015 | Hall et al. |
| 2015/0201935 A1 | 7/2015 | Weisenburgh, II et al. |
| 2015/0208902 A1 | 7/2015 | Okamoto |
| 2015/0245834 A1 | 9/2015 | Scirica et al. |
| 2015/0272576 A1 | 10/2015 | Cappola |
| 2015/0289873 A1 | 10/2015 | Shelton, IV et al. |
| 2015/0297221 A1 | 10/2015 | Kerr et al. |
| 2015/0297233 A1 | 10/2015 | Huitema et al. |
| 2016/0000439 A1 | 1/2016 | Weisenburgh, II et al. |
| 2016/0000440 A1 | 1/2016 | Weisenburgh, II et al. |
| 2016/0058447 A1 | 3/2016 | Posada et al. |
| 2016/0058492 A1 | 3/2016 | Yates et al. |
| 2016/0183948 A1 | 6/2016 | Shelton, IV et al. |
| 2016/0310204 A1 | 10/2016 | McHenry et al. |
| 2016/0338702 A1 | 11/2016 | Ehrenfels et al. |
| 2016/0374672 A1* | 12/2016 | Bear ..................... H02J 7/00 606/219 |
| 2016/0374675 A1 | 12/2016 | Shelton, IV et al. |
| 2017/0007241 A1 | 1/2017 | Shelton, IV et al. |
| 2017/0007242 A1 | 1/2017 | Shelton, IV et al. |
| 2017/0007243 A1 | 1/2017 | Shelton, IV et al. |
| 2017/0007249 A1 | 1/2017 | Shelton, IV et al. |
| 2017/0202570 A1* | 7/2017 | Shelton, IV ... A61B 17/320092 |
| 2017/0231633 A1 | 8/2017 | Marczyk et al. |
| 2017/0245856 A1 | 8/2017 | Baxter, III et al. |

(56) References Cited

U.S. PATENT DOCUMENTS

| | | | |
|---|---|---|---|
| 2017/0245858 | A1 | 8/2017 | Williams |
| 2017/0281161 | A1 | 10/2017 | Shelton, IV et al. |
| 2017/0281165 | A1 | 10/2017 | Harris et al. |
| 2017/0281168 | A1 | 10/2017 | Shelton, IV et al. |
| 2017/0290583 | A1* | 10/2017 | Reed ................ A61B 17/07207 |
| 2017/0290584 | A1* | 10/2017 | Jasemian ............. A61B 17/072 |
| 2017/0296213 | A1* | 10/2017 | Swensgard ...... A61B 17/07207 |
| 2017/0333073 | A1* | 11/2017 | Faller ..................... A61B 90/08 |
| 2018/0360454 | A1* | 12/2018 | Shelton, IV ......... A61B 17/105 |
| 2018/0360470 | A1* | 12/2018 | Parfett ............. A61B 17/07207 |
| 2019/0206565 | A1* | 7/2019 | Shelton, IV ........... A61B 90/37 |
| 2019/0261984 | A1 | 8/2019 | Nelson et al. |
| 2020/0268381 | A1 | 8/2020 | Roberts et al. |

FOREIGN PATENT DOCUMENTS

| | | |
|---|---|---|
| EP | 0 514 139 A2 | 11/1992 |
| EP | 0 536 903 A2 | 4/1993 |
| EP | 0 596 543 A1 | 5/1994 |
| EP | 1 523 944 A1 | 4/2005 |
| EP | 1 759 812 A1 | 3/2007 |
| EP | 1 915 953 A1 | 4/2008 |
| EP | 1 479 348 B1 | 7/2008 |
| EP | 2 044 893 A2 | 9/2008 |
| EP | 2 005 902 A2 | 12/2008 |
| EP | 2 090 241 A1 | 8/2009 |
| EP | 2 263 568 A2 | 12/2010 |
| EP | 2 361 562 A1 | 8/2011 |
| EP | 2 462 875 A2 | 6/2012 |
| EP | 2 486 859 A2 | 8/2012 |
| EP | 2 764 833 A2 | 8/2014 |
| EP | 2 772 192 A1 | 9/2014 |
| EP | 2 777 530 A1 | 9/2014 |
| EP | 2 923 661 A2 | 3/2015 |
| EP | 2 891 462 A1 | 7/2015 |
| EP | 2 926 742 A1 | 10/2015 |
| EP | 2 942 020 A2 | 11/2015 |
| EP | 3 135 225 A2 | 3/2017 |
| EP | 3 238 639 A2 | 3/2017 |
| EP | 3 338 653 A1 | 6/2018 |
| EP | 3 338 698 A1 | 6/2018 |
| EP | 3 338 702 A1 | 6/2018 |
| JP | 2001-087272 A | 4/2001 |
| RU | 2063710 | 7/1996 |
| WO | WO 83/02247 A1 | 7/1983 |
| WO | WO 94/24947 A1 | 11/1994 |
| WO | WO 02/30296 A2 | 4/2002 |
| WO | WO 02/096327 A2 | 12/2002 |
| WO | WO 2003/094747 A1 | 11/2003 |
| WO | WO 2004/032762 A1 | 4/2004 |
| WO | WO 2012/052729 A1 | 4/2012 |
| WO | WO 2014/139440 A1 | 9/2014 |
| WO | WO 2020/077531 A1 | 4/2020 |

OTHER PUBLICATIONS

European Patent Office, Extended European Search Report for European Application No. EP 21162419.2, entitled "Surgical Stapler Having Articulation Mechanism," dated Jun. 22, 2021, 10 pgs.

The International Bureau of WIPO, International Preliminary Report on Patentability, for International Application No. PCT/US2021/057231, entitled "Material Combinations and Processing Methods for a Surgical Instrument," dated May 11, 2023, 10 pgs.

The International Bureau of WIPO, International Preliminary Report on Patentability, for International Application No. PCT/US2021/057278, entitled "Actuation Shaft Retention Mechanism for Surgical Stapler," dated May 11, 2023, 10 pgs.

The International Bureau of WIPO, International Preliminary Report on Patentability, for International Application No. PCT/US2021/057365, entitled "Surgical Stapler Having a Powered Handle," dated May 11, 2023, 14 pgs.

The International Bureau of WIPO, International Preliminary Report on Patentability, for International Application No. PCT/US2020/025496 entitled "Reload Cover for Surgical System," dated Oct. 14, 2021, 12 pgs.

European Patent Office, Extended European Search Report for European Application No. EP 21173771.3, entitled "Reload Shaft Assembly for Surgical Stapler," dated Aug. 27, 2021, 10 pgs.

The International Bureau of WIPO, International Preliminary Report on Patentability, for International Application No. PCT/US2020/019938, entitled "Surgical Stapler Having a Two-Position Lockout Mechanism," dated Sep. 10, 2020, 10 pgs.

European Patent Office, European Search Report for European Application No. 07784007.2, entitled "Surgical Stapler," dated Jun. 15, 2012, 6 pgs.

Ethicon Endo Surgery, Inc., Contour Curved Cutter Stapler, 2014, 2 pgs.

Justright Surgical, JustRight Surgery, Dec. 31, 2014, 2 pgs.

European Patent Office, The International Search Report and the Written Opinion of the International Searching Authority for International Application No. PCT/US2014/028811, entitled "Surgical Stapler Having Actuation Mechanism with Rotatable Shaft," dated Aug. 5, 2014, 14 pgs.

European Patent Office, International Search Report and Written Opinion for International Application No. PCT/US2014/028211, entitled "Surgical Stapler with Partial Pockets," dated Sep. 8, 2014, 17 pgs.

International Searching Authority, U.S., The International Search Report and the Written Opinion of the International Searching authority for international application PCT/US2014/027768, titled "Surgical Stapler with Expandable Jaw", dated Jul. 25, 2014, 17 pgs.

The International Bureau of WIPO, International Preliminary Report on Patentability, for International Application No. PCT/US2014/028811, entitled "Surgical Stapler Having Actuation Mechanism with Rotatable Shaft," dated Sep. 15, 2015, 11 pgs.

International Searching Authority, U.S., The International Search Report and the Written Opinion of the International Searching authority for international application PCT/US2015/0035379, titled "Surgical Stapler with Circumferential Firing", dated Sep. 15, 2015, 22 pgs.

The International Bureau of WIPO, International Preliminary Report on Patentability, for International Application No. PCT/US2014/027768, entitled "Surgical Stapler with Expandable Jaw," dated Sep. 24, 2015, 9 pgs.

European Patent Office, International Search Report and Written Opinion for International Application No. PCT/US2015/050103 titled "Surgical Stapler with Self-Adjusting Staple Height" dated Feb. 17, 2016, 18 pgs.

The International Bureau of WIPO, International Preliminary Report on Patentability for International Application No. PCT/US2015/035379, entitled "Surgical Stapler with Circumferential Firing," dated Dec. 22, 2016, 14 pgs.

The International Bureau of WIPO, International Preliminary Report on Patentability for International Application No. PCT/US2015/050103, titled "Surgical Stapler With Self-Adjusting Staple Height," dated Mar. 30, 2017, 12 pgs.

European Patent Office, European Search Report for European Application No. EP 14764812.5, entitled "Surgical Stapler Having Actuation Mechanism with Rotatable Shaft," dated Apr. 6, 2017, 6 pgs.

International Searching Authority/ EPO, Invitation to Pay Additional Fees and Communication Relating to the Results of the Partial International Search for PCT/US2017/027269, entitled "Reload Shaft Assembly for Surgical Stapler," dated Jun. 28, 2017, 15 pgs.

International Searching Authority/ EPO, Invitation to Pay Additional Fees and Communication Relating to the Results of the Partial International Search for PCT/US2017/027213, entitled "Surgical Stapler Having a Powered Handle," dated Jul. 5, 2017, 11 pgs.

International Searching Authority/ EPO, Invitation to Pay Additional Fees and Communication Relating to the Results of the Partial International Search for PCT/US2017/027142, entitled "Surgical Stapler Having Articulation Mechanism," dated Jul. 10, 2017, 15 pgs.

(56) References Cited

OTHER PUBLICATIONS

European Patent Office, The International Search Report and the Written Opinion of the International Searching Authority for International Application No. PCT/US2017/027269, entitled "Reload Shaft Assembly for Surgical Stapler," dated Sep. 12, 2017, 22 pgs.
European Patent Office, The International Search Report and the Written Opinion of the International Searching Authority for International Application No. PCT/US2017/027213, entitled "Surgical Stapler Having a Powered Handle," dated Sep. 13, 2017, 17 pgs.
European Patent Office, The International Search Report and the Written Opinion of the International Searching Authority for International Application No. PCT/US2017/027142, entitled "Surgical Stapler Having Articulation Mechanism," dated Sep. 14, 2017, 21 pgs.
European Patent Office, The International Search Report and Written Opinion of the International Searching Authority for International Application No. PCT/US2016/045993 titled "Surgical Stapler Having Locking Articulation Joint", dated Jan. 24, 2017, 20 pgs.
European Patent Office, Partial European Search Report for European Application No. EP 14762896.0, entitled "Surgical Stapler with Expandable Jaw," dated Apr. 10, 2017, 6 pgs.
The International Bureau of WIPO, International Preliminary Report on Patentability, for International Application No. PCT/US2016/045993, entitled "Surgical Stapler Having Locking Articulation Joint," dated Feb. 15, 2018, 13 pgs.
European Patent Office, Extended European Search Report for European Application No. EP 18186558.5, entitled "Surgical Stapler with Partial Pockets," dated Oct. 10, 2018, 9 pgs.
The International Bureau of WIPO, International Preliminary Report on Patentability, for International Application No. PCT/US2017/027142, entitled "Surgical Stapler Having Articulation Mechanism," dated Oct. 25, 2018, 12 pgs.
The International Bureau of WIPO, International Preliminary Report on Patentability, for International Application No. PCT/US2017/027213, entitled "Surgical Stapler Having Powered Handle," dated Oct. 25, 2018, 9 pgs.
The International Bureau of WIPO, International Preliminary Report on Patentability, for International Application No. PCT/US2017/027269, entitled "Reload Shaft Assembly for Surgical Stapler," dated Oct. 25, 2018, 12 pgs.
European Patent Office, Extended European Search Report for European Application No. EP 18189960.0, entitled "Surgical Stapler with Expandable Jaw," dated Dec. 13, 2018, 6 pgs.
International Searching Authority/ EPO, Invitation to Pay Additional Fees and Communication Relating to the Results of the Partial International Search for PCT/US2019/019867, entitled "Surgical Stapler Having a Powered Handle," dated May 24, 2019, 19 pgs.
European Patent Office, The International Search Report and the Written Opinion of the International Searching Authority for International Application No. PCT/US2019/019867, entitled "Surgical Stapler Having a Powered Handle," dated Jul. 19, 2019, 24 pgs.
European Patent Office, Extended European Search Report for European Application No. EP 19150575.9, entitled "Surgical Stapler Having Actuation Mechanism with Rotatable Shaft," dated Aug. 21, 2019, 5 pgs.
European Patent Office, Extended European Search Report for European Application No. EP 19180055.6, entitled "Surgical Stapler with Circumferential Firing," dated Sep. 20, 2019, 8 pgs.
European Patent Office, The International Search Report and the Written Opinion of the International Searching Authority for International Application No. PCT/US2020/019938, entitled "Surgical Stapling Instrument Having a Two-Position Mechanism," dated Jun. 18, 2020, 16 pgs.
European Patent Office, Extended European Search Report for European Application No. EP 20157713.7, entitled "Surgical Stapler with Expandable Jaw," dated May 11, 2020, 6 pgs.
International Searching Authority/ EPO, Invitation to Pay Additional Fees for PCTUS2020/025496, entitled "Reload Cover for Surgical Stapling System," dated Jun. 18, 2019, 15 pgs.
European Patent Office, Extended European Search Report for European Application No. EP 20161294.2, entitled "Surgical Stapler with Self-Adjusting Staple Height," dated Jun. 22, 2020, 6 pgs.
European Patent Office, The International Search Report and the Written Opinion of the International Searching Authority for International Application No. PCT/US2020/025496, entitled "Reload Cover for Surgical Stapling System," dated Aug. 13, 2020, 20 pgs.
The International Bureau of WIPO, International Preliminary Report on Patentability, for International Application No. PCT/US2019/019867, entitled "Surgical Stapler Having a Powered Handle," dated Sep. 3, 2020, 16 pgs.
European Patent Office, Extended European Search Report for European Application No. EP 20197859.0, entitled "Surgical Stapler with Circumferential Firing," dated Jan. 28, 2021, 13 pgs.
European Patent Office, The International Search Report and the Written Opinion of the International Searching Authority for International Application No. PCT/US2021/057365, entitled "Surgical Stapler Having a Powered Handle" dated Apr. 13, 2022, 21 pgs.
European Patent Office, The International Search Report and the Written Opinion of the International Searching Authority for International Application No. PCT/US2022/012452, entitled "Surgical Stapler Having Shaft Recognition Mechanism" dated Apr. 13, 2022, 13 pgs.
European Patent Office, Extended European Search Report for European Application No. EP 21195788.1, entitled "Surgical Stapler with Self-Adjusting Staple Height," dated Dec. 13, 2021, 9 pgs.
International Searching Authority/ EPO, Invitation to Pay Additional Fees and Communication Relating to the Results of the Partial International Search for PCT/US2021/057365, entitled "Surgical Stapler Having a Powered Handle," dated Feb. 23, 2022, 14 pgs.
European Patent Office, The International Search Report and the Written Opinion of the International Searching Authority for International Application No. PCT/US2021/057278, entitled "Actuation Shaft Retention Mechanism for Surgical Stapler" dated Feb. 23, 2022, 15 pgs.
European Patent Office, The International Search Report and the Written Opinion of the International Searching Authority for International Application No. PCT/US2021/057231, entitled "Material Combinations and Processing Methods for a Surgical Instrument" dated Feb. 11, 2022, 15 pgs.
International Preliminary Examining Authority/US, International Preliminary Report on Patentability for International Application No. PCT/US2020/067540, titled "Electrosurgical System with Tissue and Maximum Current Identification," dated Jul. 14, 2022, 9 pgs.
European Patent Office, Extended European Search Report for European Application No. EP 22196603.9, entitled "Surgical Stapler with Expandable Jaw," dated Dec. 14, 2022, 6 pgs.
European Patent Office, Extended European Search Report for European Application No. EP 22203464.7, entitled "Surgical Stapler with Partial Pockets," dated Dec. 20, 2022, 9 pgs.
European Patent Office, Extended European Search Report for European Application No. EP 22203599.0, entitled "Surgical Stapler Having a Powered Handle," dated Feb. 7, 2023, 7 pgs.
The International Bureau of WIPO, International Preliminary Report on Patentability, for International Application No. PCT/US2022/012452, entitled "Surgical Stapler Having Shaft Recognition Mechanism," dated Jul. 27, 2023, 8 pgs.

* cited by examiner

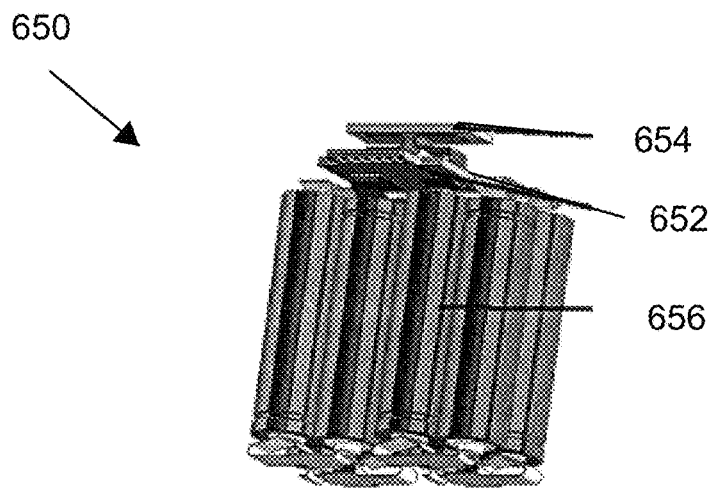
FIG. 63
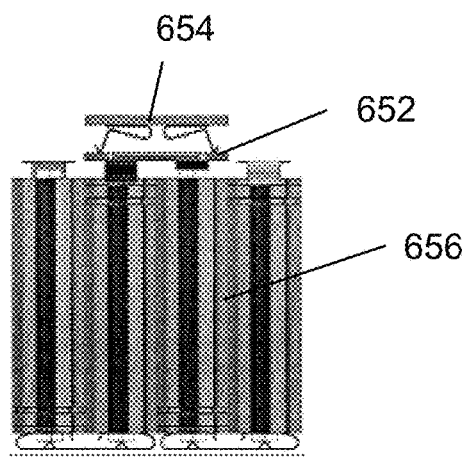 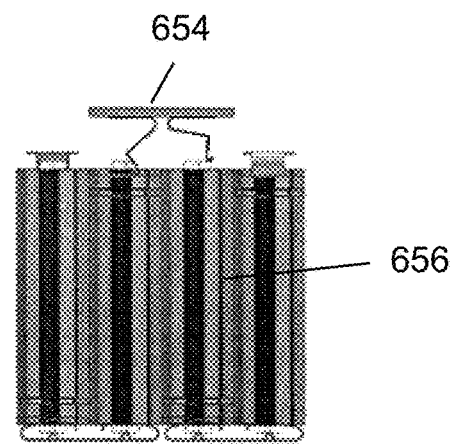
FIG. 64A  FIG. 64B

SURGICAL STAPLER HAVING A POWERED HANDLE

CROSS REFERENCE TO RELATED APPLICATIONS

This application is a continuation of U.S. patent application Ser. No. 16/287,748 entitled "Surgical Stapler Having a Powered Handle," filed Feb. 27, 2019, which claims the benefit of U.S. Provisional Patent Application Ser. No. 62/636,070, filed Feb. 27, 2018, entitled "Surgical Stapler Having a Powered Handle," and U.S. Provisional Patent Application Ser. No. 62/734,154, filed September 2018, entitled "Surgical Stapler Having a Powered Handle." Each of which is hereby incorporated herein by reference in its entirety.

BACKGROUND OF THE INVENTION

Field of the Invention

The present application relates generally to surgical occlusion instruments and, more particularly, to powered surgical staplers.

Description of the Related Art

Surgical staplers are used to approximate or clamp tissue and to staple the clamped tissue together. As such, surgical staplers have mechanisms to clamp tissue and to drive staples through the tissue. As a result, this has produced, for example, multiple triggers and handles in conjunction with complex mechanisms to provide proper stapling of the clamped tissue. With these complex mechanisms, surgical staplers can have increased manufacturing burdens, as well as potential sources for device failure and confusion for the user. Thus, reliable stapling of clamped tissue without complex mechanisms is desired.

SUMMARY OF THE INVENTION

In certain embodiments, a powered handle for a surgical stapling system is provided herein. The powered handle can comprise a drive system powered by a power supply to selectively actuate an actuation adapter. The powered handle can comprise a manual articulation mechanism to selectively actuate an articulation adapter. The powered handle can further comprise a coupler having a bayonet coupling to simultaneously couple the articulation adapter and the actuation adapter to an articulation member and a drive member in a reload shaft.

In certain embodiments, the powered handle of the surgical stapling system comprises a control system to actuate the drive system responsive to user input from a movable trigger and a fire/return button on the powered handle. The control system can further vary an actuation profile of the drive system responsive to various operating parameters including the drive system operating torque, a longitudinal position of the actuation adapter, and identification of a jaw assembly length or configuration.

In certain embodiments, the powered handle of the surgical stapling system comprises a manual articulation system including a ball screw mechanism. The ball screw mechanism can allow continuous articulation of a jaw assembly of the stapling system within a predetermined articulation range. The ball screw mechanism can be biased to a longitudinally centered position and be rapidly centered through the use of a release mechanism.

In certain embodiments, a handle assembly for a surgical stapler is provided. The handle assembly comprises a handle body, an electric motor, an actuation shaft and a mechanical return mechanism. The handle body comprises a stationary handle and a trigger pivotably coupled to the handle body. The electric motor is disposed within the handle body. The actuation shaft is slidable within the handle body along a longitudinal axis and rotatable within the handle body about the longitudinal axis. The actuation shaft comprises a rack formed thereon. The actuation shaft is rotatable from a first position wherein the rack is operationally engaged with the electric motor to longitudinally slide the actuation shaft to a second position wherein the rack is disengaged from the electric motor and engaged with the manual return mechanism. The manual return mechanism comprises a return lock mechanism slidable within the handle body, a shaft rotation mechanism, and a shaft retraction mechanism.

In certain embodiments, a handle assembly for a surgical stapler is provided. The handle assembly comprises a handle body, an electric motor, an actuation shaft, a motor gear, an auxiliary gear. The handle body comprising a stationary handle and a trigger pivotably coupled to the handle body. The electric motor is disposed within the handle body. The motor comprises an output shaft. The actuation shaft is slidable within the handle body along a longitudinal axis. The motor gear is coupled to the output shaft of the motor. The auxiliary gear is in driven engagement with the motor gear. The auxiliary gear is operatively engaged with the rack. The auxiliary gear comprises a first gear segment rotationally coupled to a second gear segment and a central region extending between the first gear segment and the second gear segment. The first gear segment is in driven engagement with the motor gear and the second gear segment is operatively engaged with the rack.

In certain embodiments, a handle assembly for a surgical stapler having a removably coupled instrument shaft is provided. The handle assembly comprises a handle body, a power system, an actuation shaft, an articulation mechanism, and an articulation lockout mechanism. The handle body comprises a stationary handle and a trigger pivotably coupled to the handle body. The power system is within the handle body. The actuation shaft is operatively coupled to the power system. The actuation shaft is slidable within the handle body along a longitudinal axis. The articulation mechanism comprises a manually actuated articulation knob and an articulation adapter. The manually actuated articulation knob is positioned at a proximal end of the handle body and rotatable about the longitudinal axis. The articulation adapter is positioned at the distal end of the handle body. The articulation adapter is operatively coupled to the articulation knob such that rotation of the articulation knob about the longitudinal axis longitudinally slides the articulation adapter. The articulation lockout mechanism disengages the articulation knob from the articulation adapter when no instrument shaft is coupled to the surgical stapler.

In certain embodiments a handle assembly for a surgical stapler is provided. The handle assembly comprises a handle body, a power system, an actuation shaft, a position sensor, and a control system. Thea handle body comprises a stationary handle and a trigger movably coupled to the handle body. The power system is within the handle body. The power system comprises a motor and a power source positionable within the handle body. The actuation shaft is operatively coupled to the power system. The actuation shaft is longitudinally slidable within the handle body. The position sensor is configured to determine the longitudinal position of the actuation shaft. The control system is electrically coupled to the power system, the trigger, and the position sensor. The control system is configured to define a motor drive logic profile to define at least one operational parameter for the motor at a position of the actuation shaft corresponding to a grasper zone, a lockout zone, and a firing zone.

In certain embodiments a handle assembly for a surgical stapler having a removably coupled instrument shaft having a lockout mechanism is provided. The handle assembly comprises a handle body, a power system, an actuation shaft, a position sensor, and a control system. The handle body comprises a stationary handle and a trigger pivotably coupled to the handle body. The power system is within the handle body. The power system comprises a motor and a power source positionable within the handle body. The actuation shaft is operatively coupled to the power system. The actuation shaft is longitudinally slidable within the handle body. The position sensor is configured to determine the longitudinal position of the actuation shaft. The control system is electrically coupled to the power system, the trigger, and the position sensor. The control system comprises a lockout module configured to monitor a current draw of the motor and the longitudinal position of the actuation shaft and calculate a slope of a current draw profile of the motor and detect engagement of the lockout mechanism using the monitored slope. The lockout module is configured to depower operation of the motor upon detection of engagement of the lockout mechanism.

BRIEF DESCRIPTION OF THE DRAWINGS

FIG. 63 is a perspective view of one embodiment of removable memory module for a powered handle assembly;

FIG. 64A is a side view of removal of the removable memory module of FIG. 63;

FIG. 64B is a side view of removal of the removable memory module of FIG. 63;

DETAILED DESCRIPTION OF THE INVENTION

Figure 1:
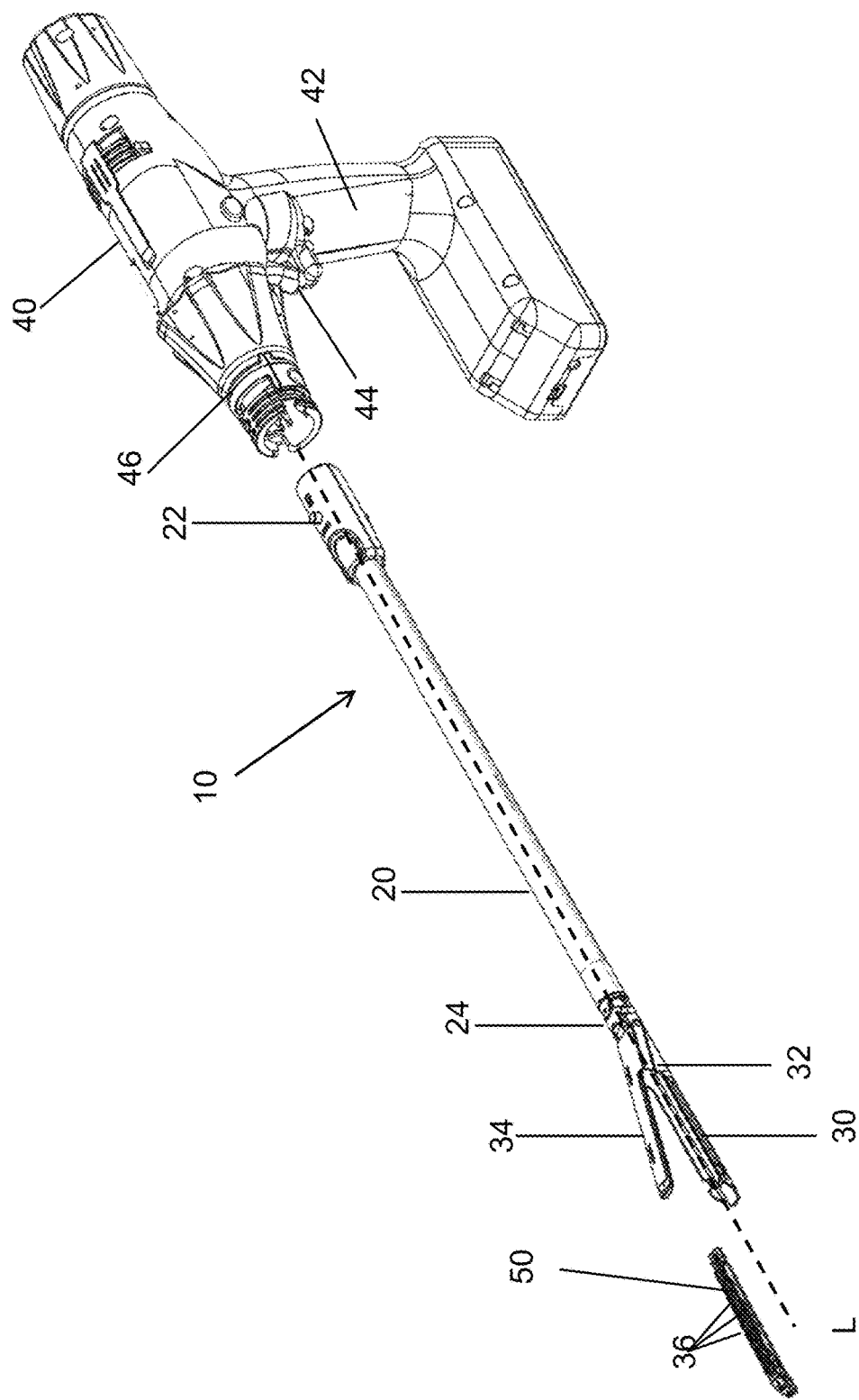
FIG. 1 is a perspective view of an embodiment of surgical stapling system having an embodiment of powered handle.
Figure 2:
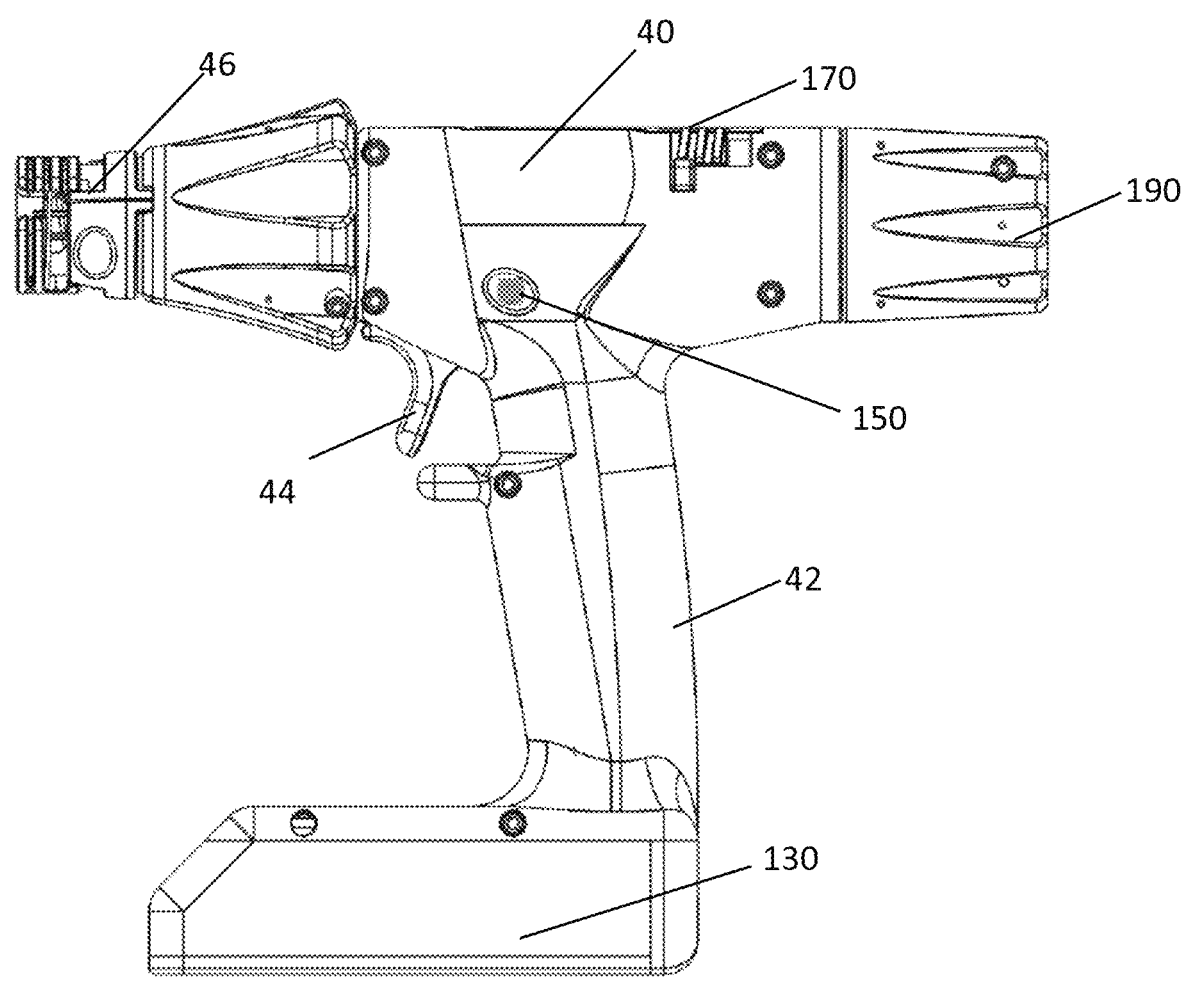
FIG. 2 is a side view the powered handle of the surgical stapling system of FIG. 1.

With reference to FIGS. 1-2, an embodiment of surgical stapling system is illustrated. The illustrated embodiment of surgical stapler 10 comprises an elongate shaft 20, a jaw assembly 30, and a handle assembly 40. FIG. 1 illustrates the surgical stapler 10 with the jaw assembly 30 in an open configuration with an embodiment of powered handle having powered staple firing and manual jaw assembly articulation. FIG. 2 illustrates the powered handle 40 of the surgical stapler system 10 with the elongate shaft removed. The powered handle 40 of FIG. 2 has powered staple firing and manual jaw assembly articulation. In the illustrated embodiments, the shaft 20 and jaw assembly 30 can be freely rotated about a longitudinal axis defined by the shaft 20 by rotation of a rotation knob on the handle 40. In other embodiments, the stapling system can be configured to allow rotation of the jaw assembly about the longitudinal axis within a predefined range or a rotationally fixed jaw assembly.

With continued reference to FIG. 1, the illustrated embodiment of surgical stapler 10 can be sized and configured for use in laparoscopic surgical procedures. For example, the elongate shaft 20 and jaw assembly 30 can be sized and configured to be introduced into a surgical field through an access port or trocar cannula. In some embodiments, the elongate shaft 20 and jaw assembly 30 can be sized and configured to be inserted through a trocar cannula having a relatively small working channel diameter, such as, for example, less than 8 mm. In other embodiments, elongate shaft 20 and jaw assembly 30 can be sized and configured to be inserted through a trocar cannula having a larger working channel diameter, such as, for example, 10 mm, 11 mm, 12 mm, or 15 mm. In other embodiments, it is contemplated that certain aspects of the surgical staplers described herein can be incorporated into a surgical stapling device for use in open surgical procedures.

With continued reference to FIG. 1, as illustrated, the elongate shaft 20 comprises a generally tubular member. The elongate shaft 20 extends from a proximal end to a distal end. The elongate shaft 20 defines a central longitudinal axis, L, of the surgical stapler 10 extending between the proximal end 22 and the distal end 24.

With continued reference to FIG. 1, in the illustrated embodiment, the jaw assembly 30 is coupled to the elongate shaft 20 at the distal end of the elongate shaft 20. The jaw assembly 30 comprises a first jaw 32 and a second jaw 34 pivotally coupled to the first jaw 32. In the illustrated embodiment, the first jaw 32 is fixed to the distal end 24 of elongate shaft 20 such that it extends distally along the central longitudinal axis, L and is articulable with respect to the elongate shaft 20 responsive to an articulation mechanism in the handle 40. In an initial configuration, the first jaw 32 includes a plurality of staples 36 disposed therein within a reload 50. In other embodiments, the reload 50 can be integrated with the jaw assembly 30 such that the entire shaft assembly 20 and jaw assembly 30 with loaded staples define a single reload assembly. In some embodiments, staples can be initially positioned in the second jaw 34.

With continued reference to FIG. 1, in the illustrated embodiment, the jaw assembly 30 can be actuated from an open configuration (FIG. 1) to a closed configuration to a stapling configuration by a drive member or beam that is longitudinally slidable within the elongate shaft. In an initial position, the beam can be positioned at the distal end 24 of the elongate shaft 20. With the beam in the initial position, the second jaw 34 is pivoted away from the first jaw 32 such that the jaw assembly 30 is in the open configuration. The actuation beam engages the second jaw 34 upon translation of the actuation member or beam distally along the longitudinal axis L. Translation of the actuation beam distally from the initial position a first distance can actuate the jaw assembly from the open configuration to the closed configuration. With the jaw assembly 30 in the closed configuration, the actuation beam can be returned proximally the first distance to return the jaw assembly 30 to the open configuration. A distal end of the actuation beam can advance a staple slider configured to deploy staples from the first jaw 32 such that further translation of the actuation beam distally past the first distance deploys the plurality of staples 36 from the reload 50 in the first jaw 32.

With continued reference to FIG. 1, in the illustrated embodiment, the handle assembly is configured to be coupled to the elongate shaft 20 at the proximal end of the elongate shaft 20. As illustrated, the handle assembly 40 has a pistol grip configuration with a housing defining a stationary handle 42 and a movable handle 44 or trigger pivotably coupled to the stationary handle 42. It is contemplated that in other embodiments, surgical stapler devices including aspects described herein can have handle assemblies with other configurations such as, for example, scissors-grip configurations, or in-line configurations. As further described in greater detail below, the handle assembly 40 houses a powered actuation mechanism configured to selectively advance an actuation shaft responsive to movement of the movable handle 44.

In the illustrated embodiment, the surgical stapler 10 can include the plurality of staples 36 positioned in a disposable cartridge reload 50 while the jaw assembly 30 is configured to be reused with multiple staple cartridge reloads 50 in a single procedure. In the some embodiments, the elongate shaft 20 and jaw assembly 30 define a disposable reload shaft that is removably couplable to the handle assembly 40. Accordingly, in the illustrated embodiment the handle assembly 40 includes a coupler 46 at the distal end thereof. The coupler 46 is adapted to engage the elongate shaft 20 of the surgical stapler 10. The coupler 46 can have a bayonet connection having an outer connector that can removably couple the handle assembly 42 to the elongate shaft 20, a first inner connector that can removably couple the actuation shaft of the handle assembly 42 to the drive member of the elongate shaft 20, and a second inner connector that can removably couple an articulation coupler of the handle assembly 42 to an articulation link of the elongate shaft 20. These three removable couplings occur simultaneously when an elongate shaft 20 is coupled to the handle assembly 42. Accordingly, the surgical stapler 10 can be configured such that the handle assembly 40 can be reused with multiple reload shafts 20 during a surgical procedure. It is contemplated that in other embodiments, the handle assembly and some portion of the elongate shaft can be reusable while a remainder of the elongate shaft in the jaw assembly define a disposable cartridge. In certain other embodiments, the handle assembly and the elongate shaft can be reusable while the jaw assembly defines a disposable cartridge. In still other embodiments, a jaw insert housing a plurality of staples can define a disposable cartridge while the remainder of the surgical stapler is reusable.

With reference to FIG. 2, an embodiment of powered handle for a surgical stapling system is illustrated. The powered handle can be used with various shaft reloads and cartridges such that the shaft configuration, jaw assembly configuration, and staple configuration can be selected for a particular procedure. The illustrated embodiment of handle provides powered (motor-driven) clamping and opening of the jaws and firing of the staple line. Articulation of the jaw assembly can be manually controlled by an articulation knob that the operator rotates. The motor is controlled by an embedded control system that dictates functionality of the handle during different stages of use.

With continued reference to FIG. 2, the powered handle 40 comprises a pistol-grip configuration with a stationary handle 42 and a movable handle 44 or trigger pivotably coupled thereto. A power supply 130 or battery can be positioned on a lower surface of the stationary handle. The powered handle 40 can further comprise a user control such as a fire or fire/reverse button 150 to allow a user to selectively control a stapling sequence. The powered handle 40 can further comprise a redundant, manual override return system 170 to allow a user to manually return the stapling system to an open configuration in the event of a powered system failure, control system failure, power supply failure, "lockjaw," or other mechanical binding. The powered handle can further comprise a manual articulation mechanism including a rotatable articulation knob 190. In the illustrated embodiment, the articulation knob 190 is positioned on the proximal end of the powered handle and is rotatable about an axis generally corresponding to the longitudinal axis of the stapling system. In some embodiments, the powered handle can further include an illuminated user display, such as an annular light ring to display desired status indicia to a user.

Various embodiments of powered handle assemblies and associated actuation mechanisms are disclosed in U.S. patent application Ser. No. 15/486,227, filed Apr. 12, 2017, entitled "Reload Shaft Assembly for Surgical Stapler" and U.S. patent application Ser. No. 15/486,008, filed Apr. 12, 2017, entitled "Surgical Stapler Having a Powered Handle," both of which are incorporated by reference herein in their entireties.

Powered Drive System

Figure 3:
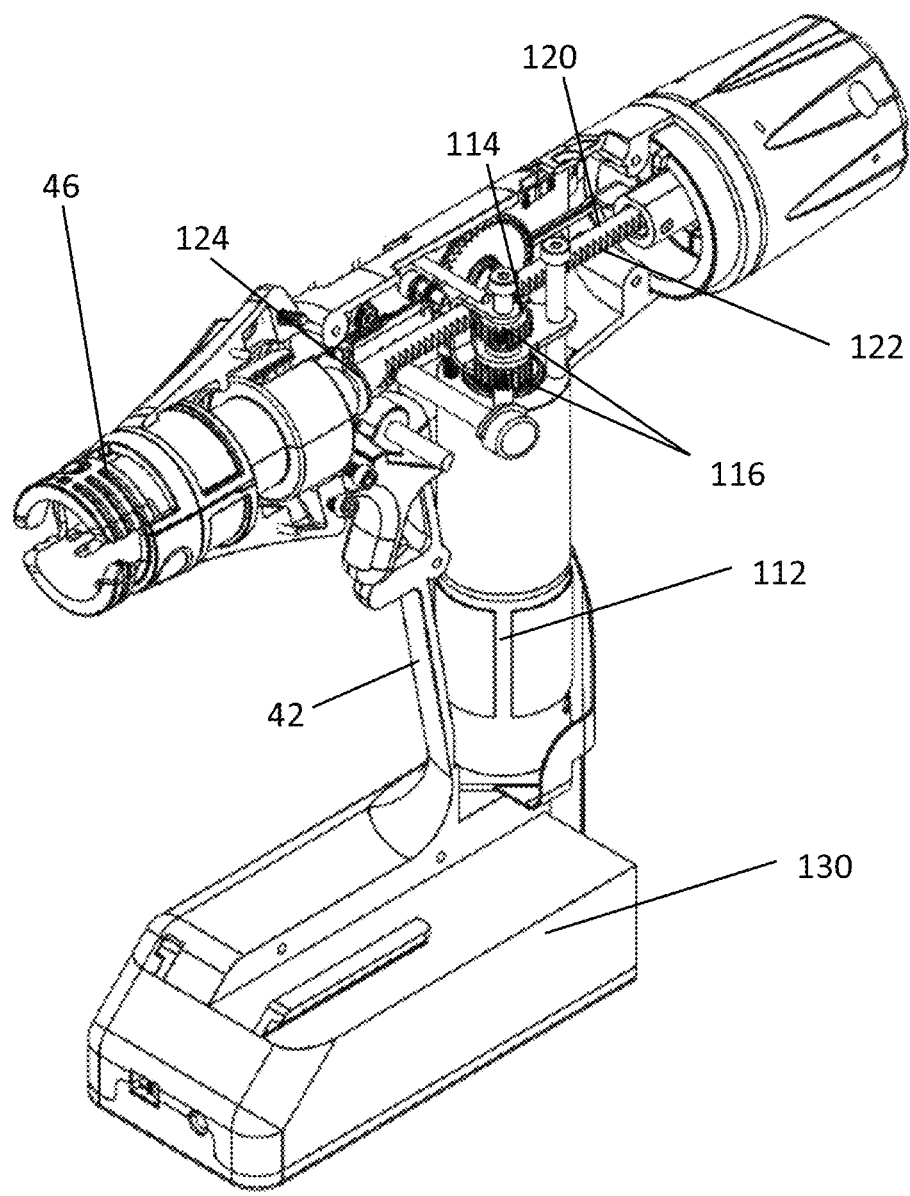
FIG. 3 is a partial cutaway perspective view of the powered handle of FIG. 2 with components removed to illustrate a drive system thereof.

With reference to FIG. 3, a partial cut-away view of the powered handle is illustrated. In the illustrated cut-away view, several components of the powered handle have been removed to clearly depict a drive system of the powered handle. In the illustrated embodiment, the drive system comprises a motor 112 positioned within the stationary handle 42, a motor gear 114 positioned on an output shaft of the motor 112, and an auxiliary gear 116 in driven engagement with the motor gear 114. In some embodiments, the motor 112 is a brushed DC gearmotor. Advantageously, transmitting power through the auxiliary gear 116 can allow the motor 112 to be laterally centered within the stationary handle to enhance handle balance and user ergonomics. Furthermore, in some embodiments, the motor gear 114 and auxiliary gear 116 can be configured to provide a desired operational torque at the rack 122. In some embodiments, the motor 112 can include a multigear transmission operationally coupled between the motor 112 and the motor gear 114 coupled to the auxiliary gear 116 to provide the desired operational torque. The motor 112 can be electrically coupled to the power supply 130 via a control system. The control system within the handle interfaces with the drive system to measure the position of the actuation shaft 120 and therefore the actuation of the jaw assembly.

The drive system is mounted to hardware that provides information to a control system including a microcontroller within the handle. This embedded system can control the speed and torque of the motor. It can also control functionality of the device based on user inputs (movement of the trigger and pressing of the FIRE/REVERSE button) and position of the drive system. The control system can also measure feedback from the motor to determine whether loads are too high to continue firing staples, or whether a reload cartridge lockout has been activated. It will also measure battery life and can limit the number of firings of the device. While the drive system is configured primarily for powered operation, in certain embodiments it can be desirable to provide a manual return mechanism to override powered operation as further described herein.

Figure 4:
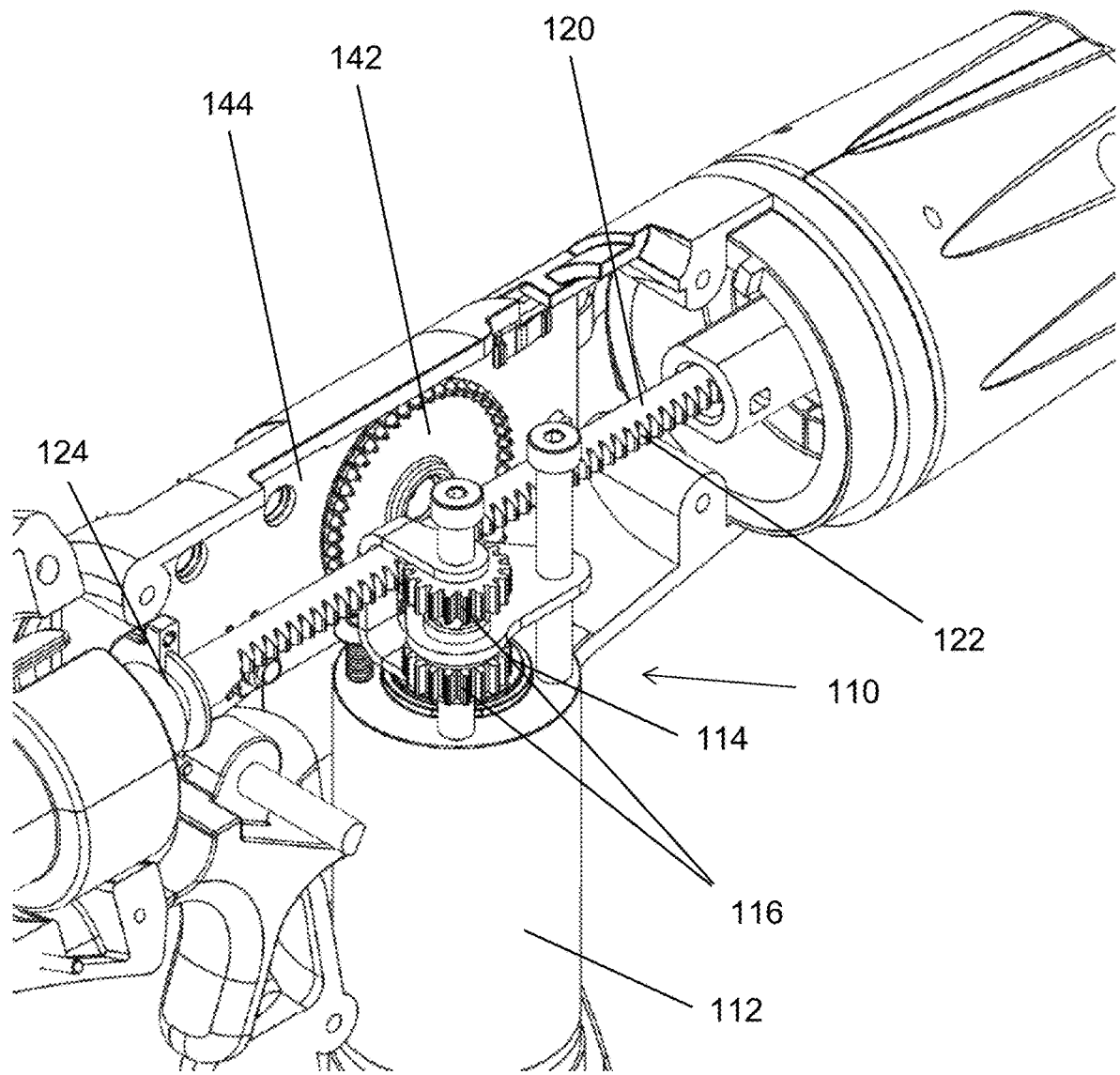
FIG. 4 is a perspective view of an embodiment of drive system for the powered handle of FIG. 2.
Figure 5:
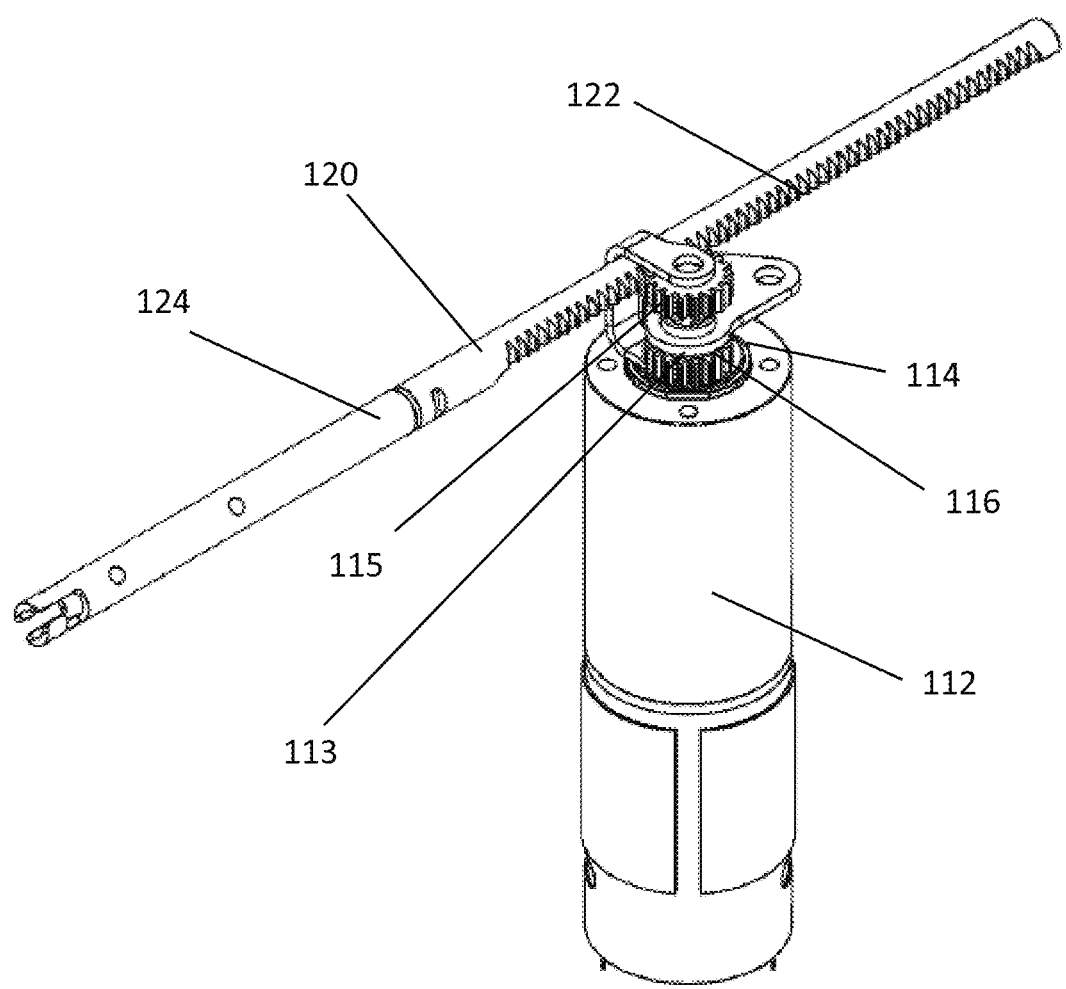
FIG. 5 is a perspective view of the drive system of FIG. 4.
Figure 6:
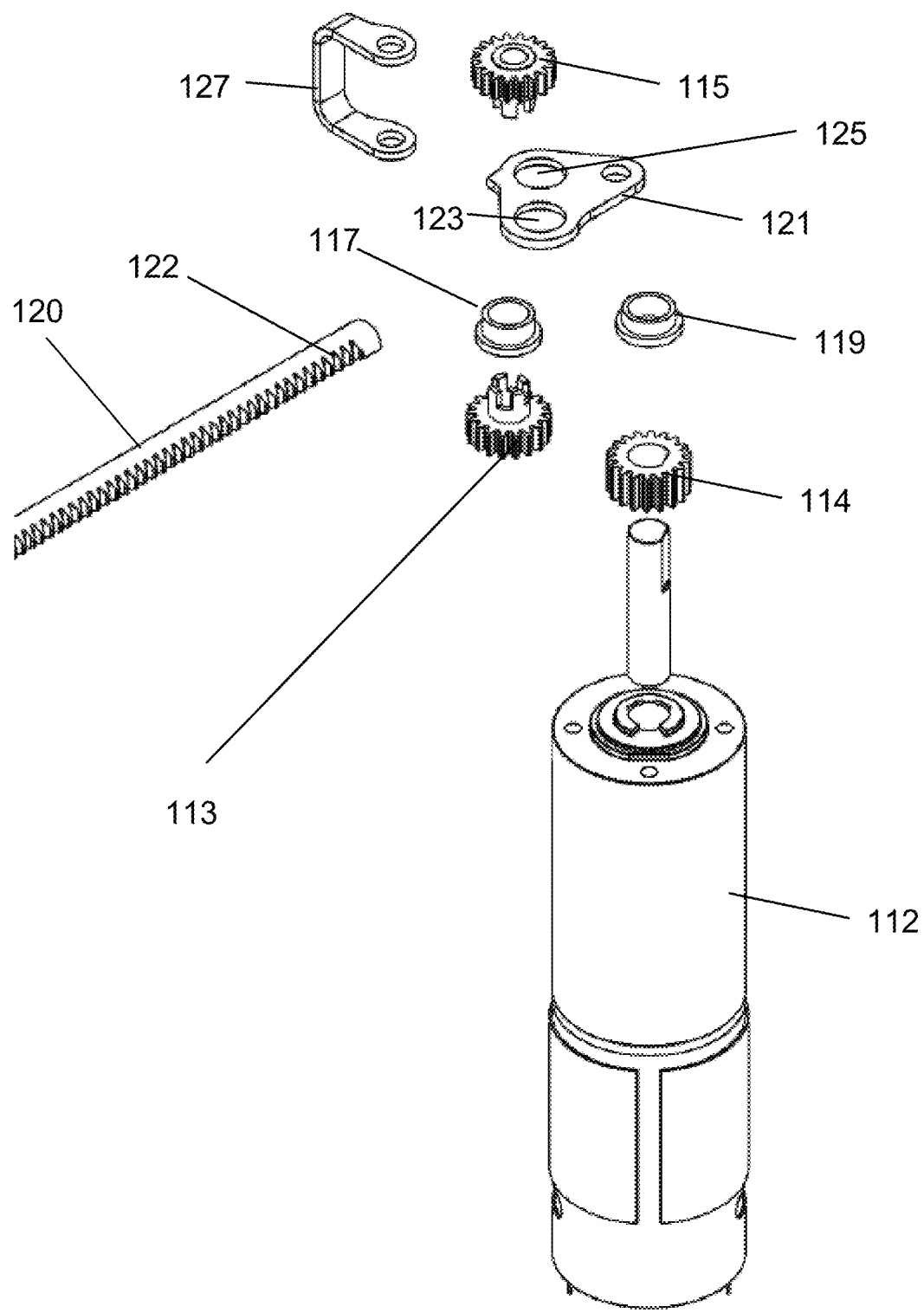
FIG. 6 is an exploded perspective view of the drive system of FIG. 4.

With reference to FIGS. 4-6, detail views of the drive system of the powered handle are illustrated. In the illustrated embodiment, the drive system comprises a bifurcated auxiliary gear 116 that is supported between its endpoints by a support plate 121. Advantageously, this supported arrangement for the auxiliary gear 116 provides a robust mechanism that can significantly reduce a tendency of the motor gear 114 from separating from the auxiliary gear 116 in heavy loading conditions.

With reference to FIGS. 5-6, the bifurcated auxiliary gear 116 comprises a first gear segment 113 rotationally coupled to a second gear segment 115. The first gear segment 113 can comprise a first engagement surface, and the second gear segment 115 can comprise a second engagement surface such that the first engagement surface and the second engagement surface can be coupled to rotationally couple the first gear segment 113 to the second gear segment 115. In the illustrated embodiment, the first gear segment 113 comprises an axially extending boss defining the first engagement surface, and the second gear segment 115 comprises an axially extending boss defining the second engagement surface. The axially extending bosses of the first gear segment and the second gear segment each comprise a square toothed or 'castle' profile that allows rotational coupling of the first gear segment 113 and the second gear segment 115. In some embodiments, when the first and second gear segments 113, 115 are rotationally coupled, the axially extending bosses are engaged to form a central region having an outer diameter that is less than an outer diameter of either of the first gear segment 113 and the second gear segment 115.

With reference to FIG. 6, an exploded view of the drive system having a bifurcated auxiliary gear 116 is illustrated. As illustrated, the drive system further comprises a support plate 121 positioned between a first end and a second end of the auxiliary gear 116. The support plate 121 can be a rigid plate having an auxiliary gear bore 123 and a motor gear bore 125 formed therein. In some embodiments, the support plate 121 can comprise a metallic material. The drive system can further comprise an auxiliary gear bushing 117 positioned in the auxiliary gear bore 123 and a motor gear bushing 119 positioned in the motor gear bore 125. The bushings 117, 119 can comprise material having a relatively low coefficient of friction such as a DELRIN® material. An actuation shaft bracket or guide member 127 can facilitate engagement of the rack 122 of the actuation shaft 120 with the second gear segment 115 of the auxiliary gear 116.

With reference to FIGS. 5-6, the first gear segment 113 of the auxiliary gear 116 and the second gear segment 115 of the auxiliary gear can be assembled about the support plate 121 such that the central region of the auxiliary gear 116 extends through the auxiliary gear bore 123 and auxiliary gear bushing 117 and the auxiliary gear 116 is supported between the first end and the second end. In the illustrated embodiment, the first gear segment 113 of the auxiliary gear 116 is in geared engagement with the motor gear 114. The second gear segment 115 of the auxiliary gear 116 is in geared engagement with the rack surface 122 of the actuation shaft 120. The support plate 121 can be encapsulated by walls of the handle assembly housing and bosses formed thereon to provide support to the drive system.

Figure 7:
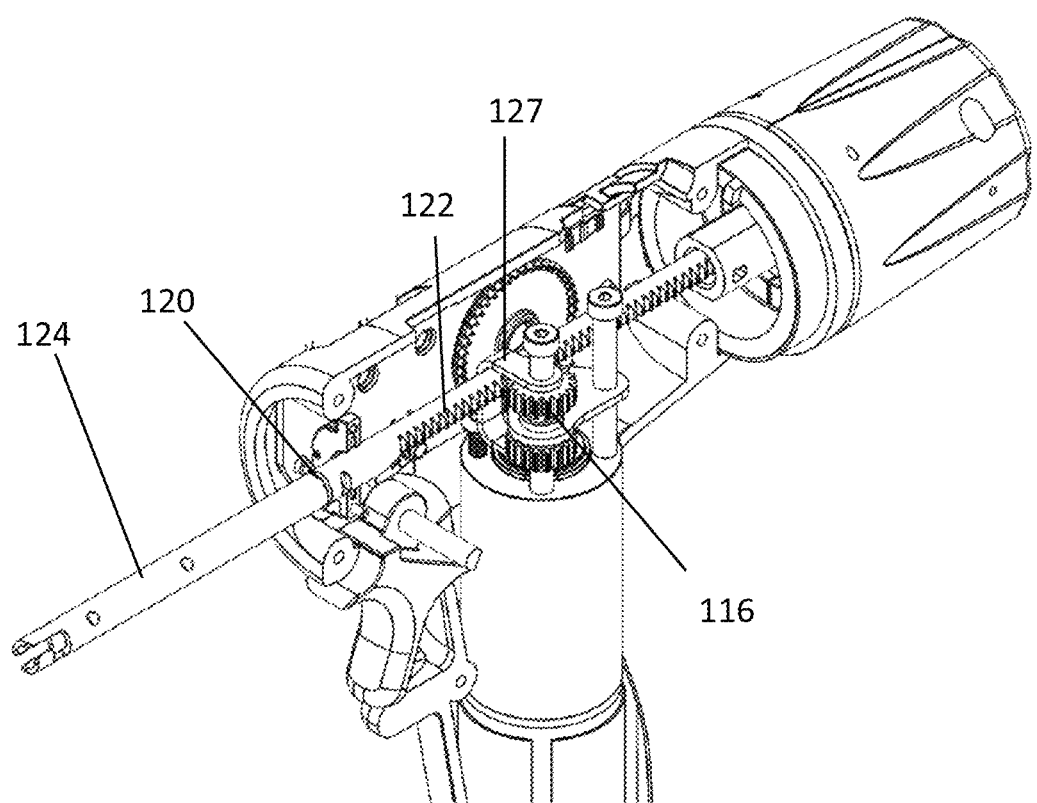
FIG. 7 is a perspective view of the drive system of FIG. 4.

With reference to FIG. 7, during powered operation, the auxiliary gear 116 is in meshed engagement with the rack 122 on an actuation shaft 120 extending longitudinally within the handle body. In the illustrated embodiment, the auxiliary gear is supported in a guide member through which the actuation shaft 120 slides. The guide member 127 assists in maintaining meshed contact between the auxiliary gear 116 and the rack 122. A distal end of the actuation shaft 120 is freely rotatably coupled to an actuation adapter 124 that extends longitudinally into the coupler 46 (FIG. 1) at the distal end of the powered handle.

With the shaft 20 coupled to the coupler 46 of the powered handle 40, the actuation adapter 124 connects to a drive member in the shaft 20 via a bayonet connection. Therefore, when the shaft 20 is attached to the handle 40, the motor 112 and rack 122 will drive a drive member extending within the instrument shaft 20 and coupled to the jaw assembly. Thus, the drive system within the handle comprises a "rack and pinion" design. Operation of the motor 112 responsive to a user's input will drive the actuation shaft 120 longitudinally forward and reverse to selectively actuate the stapler in closing, firing, or opening operations.

Figure 8:
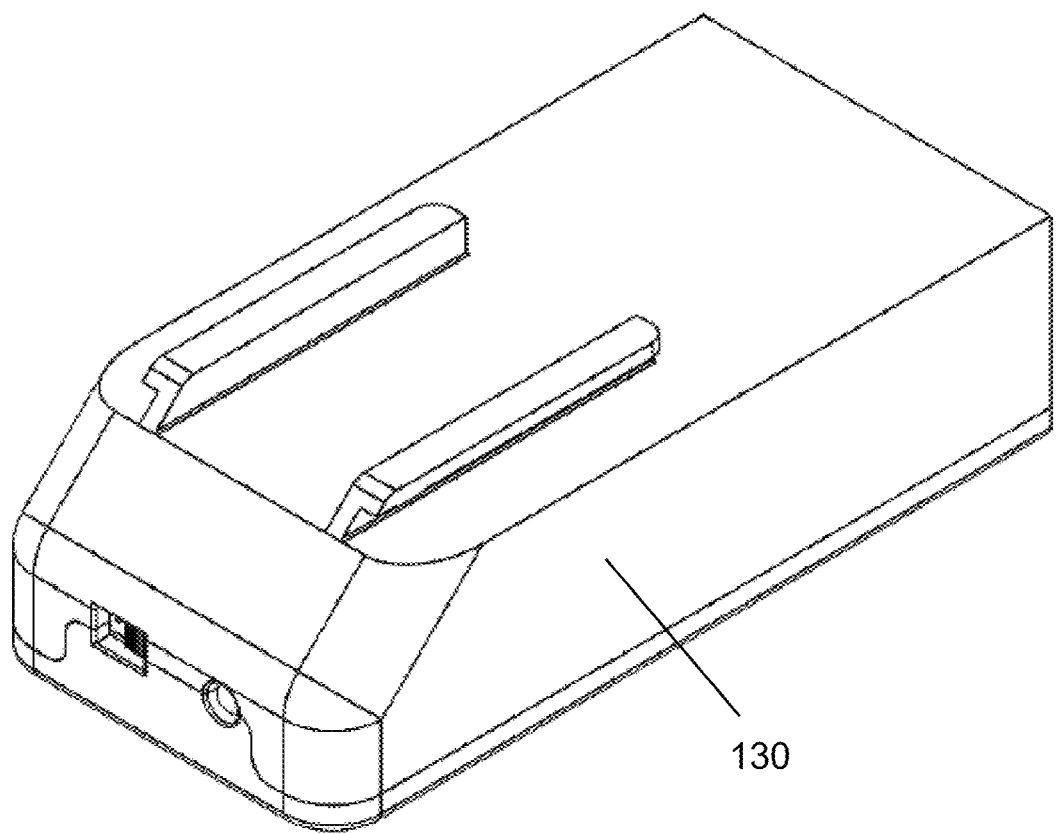
FIG. 8 is a perspective view of an embodiment of power supply for the powered handle of FIG. 2.
Figure 9:
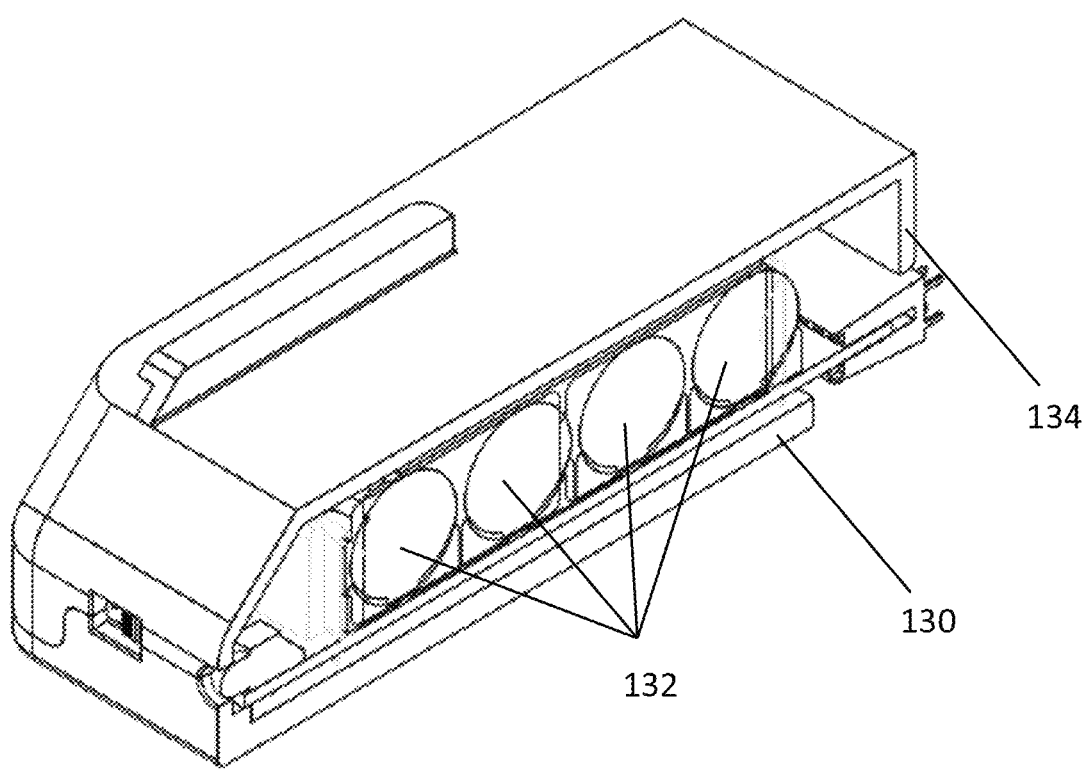
FIG. 9 is a cross-sectional perspective view of an embodiment of power supply of FIG. 8.

With reference to FIGS. 8 and 9, an embodiment of power supply 130 for the powered handle 40 is illustrated. The power supply 130 can be configured to deliver direct current to the powered handle motor and control system. In the illustrated embodiment, the stapler can operate at 12 V. The illustrated power supply can comprise four 3V lithium-ion batteries 132 connected in series to produce a 12V power supply. As illustrated, the batteries 132 are stacked in a 4 by 1 configuration in a plastic housing 134 to form the battery pack. In other embodiments, other numbers and configurations of individual battery cells can be used to form the battery pack. For example, in certain embodiments, the battery pack can be comprised of AA, AAA, or another standard or purpose-built single use or rechargeable chemistry battery. In the illustrated embodiment of powered handle 40, the battery pack is located at the bottom of the stationary handle. Desirably, this positioning provides a stable surface to set the handle 40 on a flat surface. It is contemplated that in other embodiments, the power supply can be positioned elsewhere in the handle, such as at a proximal end thereof. The power supply 130 can comprise a main power switch and indicator light, such as a light emitting diode. Through the use of lighting colors, flashing sequences, or solid illumination, the indicator light can be configured to display the power on/off status of the power supply, a low power condition, or other power supply status information, such as a recharging status.

With continued reference to FIGS. 8 and 9, in some embodiments, the power supply 130 can be packaged with the handle 40 but will not be installed before use. At the time of use, the user can install the battery pack by engaging the power supply 130 with the bottom of the handle 40. Advantageously, shipping the battery pack uninstalled can reduce an incidence of accidental battery discharge before use. Moreover, a removable battery pack can allow the stapler system be easily upgraded with a new battery as new battery technology becomes available. In other embodiments, the power supply can be packaged installed in the handle with a removable strip blocking electrical connection of the battery pack. In still other embodiments, the handle can be supplied with a power cable configured to be plugged into an AC or DC power source such as a wall socket, a USB connector, or another standard electrical connection.

In some embodiments, the power source further comprises a memory module such as a non-volatile memory that can store a digital record of the usage of the stapler. For example, the memory module can be configured to record details of each firing of the stapler including a periodic sampling of the battery voltage and motor current during firing, the sequence of states of the software state machine, any unexpected events that may have occurred, the shaft types that were used, the number of firings, the intervals between firings, and the model and serial number of the stapler handle. It can also record if the battery pack itself has been used so that users cannot reuse the battery pack. In other embodiments, a memory module can be disposed in the handle assembly separated from the power source, such as, for example positioned on or electrically coupled to a circuit board 144 (FIG. 4), or positioned to be easily removable from an electrical port on the handle assembly, such that the memory module is not integrated with the power source.

In some embodiments, the powered handle 40 and associated power supply 130 can be configured for use in a single procedure and disposal following the procedure. The power supply 130 can include a power drain to reduce an opportunity for reuse. Following use in a surgical procedure, a user can remove the battery pack from the handle 40. Removing the battery pack from the handle 40 can initiate draining the batteries. For example, after the battery pack has been used once, a mechanical feature that can short circuit the battery by connecting the terminals to a low value resistor or an electrical feature can accomplish the same task with a circuit. Additionally, if the battery pack is left in the handle 40 after the surgical procedure is complete, in some embodiments, the control system of the handle is programmed to disable functionality and drain the battery pack after a maximum time limit. For example, in embodiments of power source including a memory module, the microcontroller can include a firing management module that can modify a memory location such as a firing count memory location, on the memory module after a predetermined number of firing strokes. The microcontroller can be configured to evaluate the firing count memory location in a startup operational sequence. If this memory location indicates that the battery has been used, in some embodiments, the microcontroller can be configured to disable the stapler and activate a discharge circuit in the power source. The microcontroller can also be configured to activate the discharge circuit in other predetermined operational conditions, such as when the handle assembly has been powered on for a predetermined period, such as, in one embodiment, longer than 12 hours, has been fired more than a predetermined number of times such as, in one embodiment 12 times, had deployed a manual override return mechanism, or has experienced a non-recoverable failure.

Figure 10:
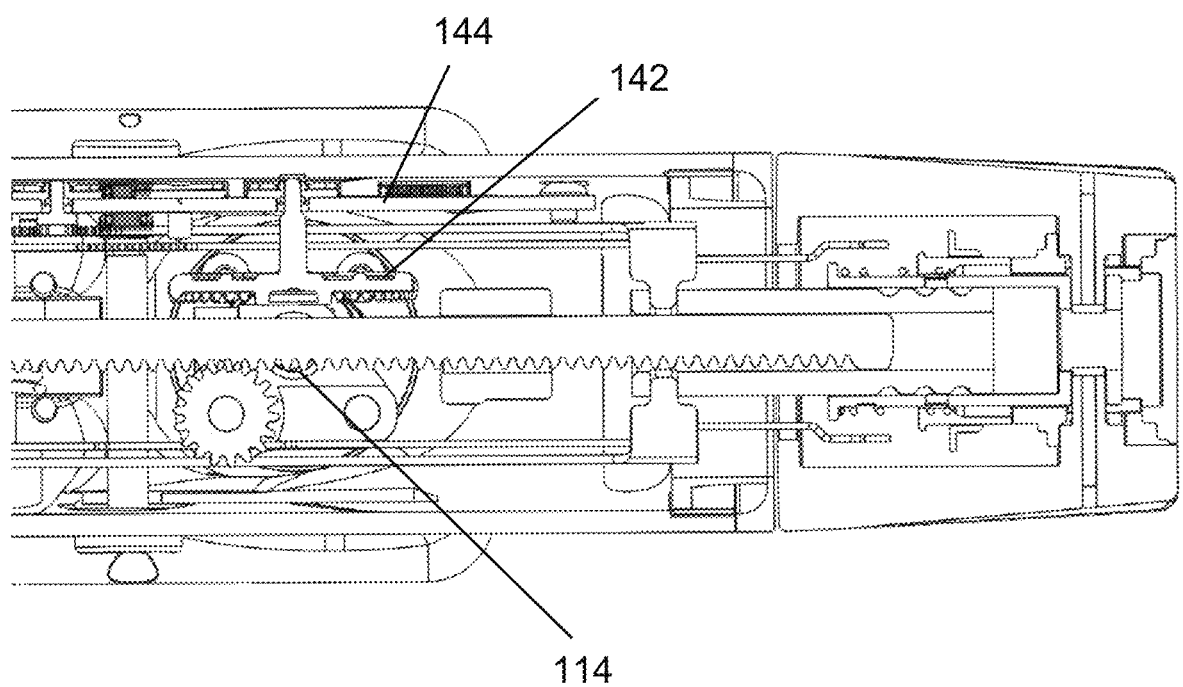
FIG. 10 is a cut-away top view of the powered handle of FIG. 2.

With reference to FIGS. 4 and 10, an embodiment of position sensor mechanism for use in the powered handle is illustrated. In operation, rotation of the motor gear 114 correspondingly rotates a crown gear 142 mounted in the handle 40. The crown gear 142 is coupled to a potentiometer such that the position of the motor gear 114 and thus the actual position of the actuation rack can be determined based on the measuring changes in resistance at the potentiometer. In some embodiments, the potentiometer can be mounted on a circuit board 144 on which the control system can be positioned. While the illustrated embodiment includes a potentiometer-based position sensor mechanism, it is contemplated that in other embodiments, other position sensing mechanisms can be used, including, for example, use of a magnetic encoder with hall effect sensors, use of limit switches that activate when the actuation shaft has traveled a predetermined distance, use of optical systems such as photodiodes to measure travel of a pattern along the actuation shaft, an optical encoder positioned on a shaft of the motor, or other position sensing systems.

Articulation Mechanism

With reference to FIGS. 11-17, an embodiment of articulation mechanism for the powered handle 40 is illustrated. In the illustrated embodiment, the handle can articulate the jaw assembly at the distal end of the shaft up to 45° in a fully articulated position in either direction relative to a longitudinally centered position. In some embodiments, the powered handle uses a manual articulation mechanism including a series of components coupled to the manually actuated articulation knob 190 at the proximal end of the handle. In other embodiments, the manually actuated articulation knob and certain associated elements of the articulation mechanism can be positioned in other locations on the handle such as adjacent a distal end of the handle.

Figure 11:
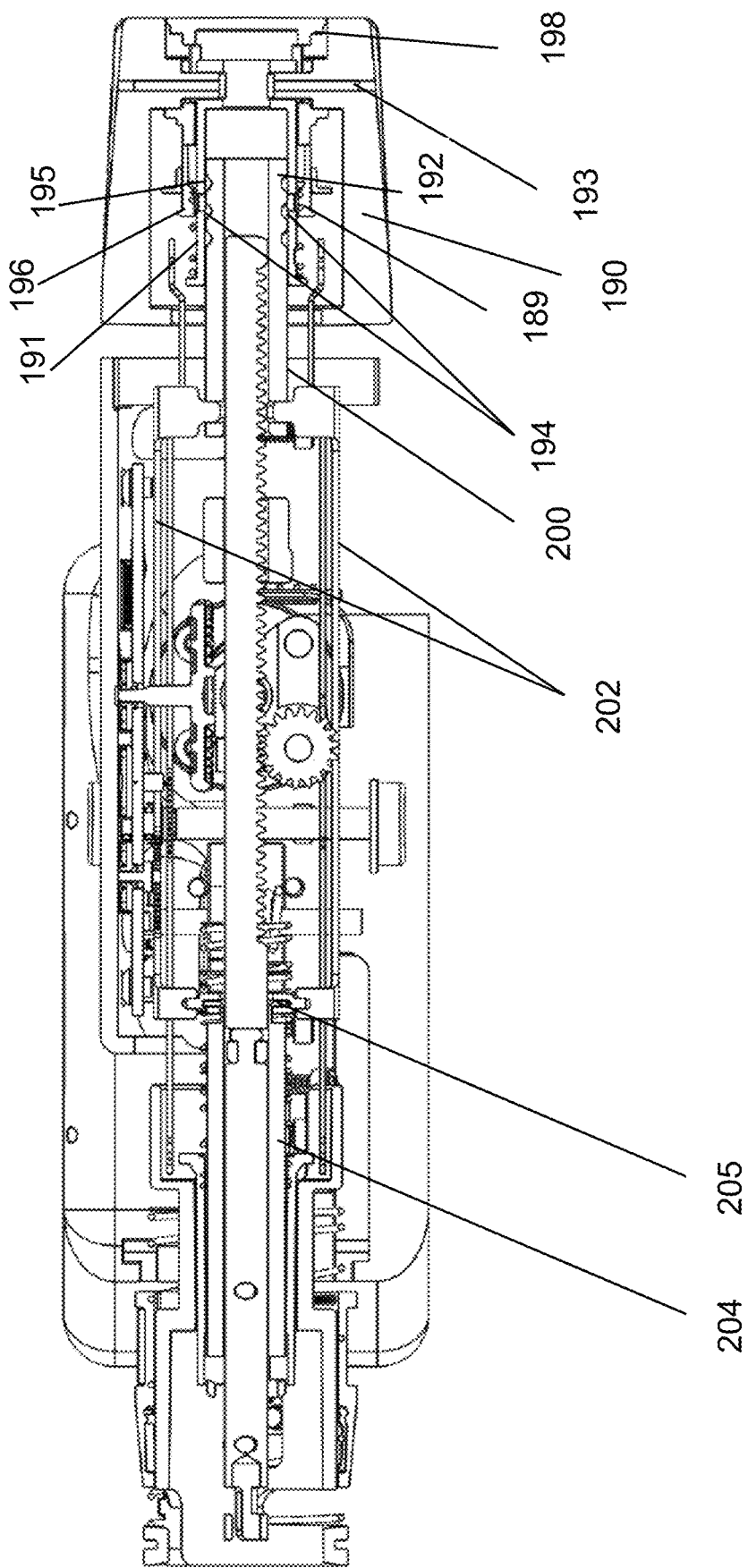
FIG. 11 is a cut-away top view of an embodiment of articulation mechanism of the powered handle of FIG. 2.
Figure 12:
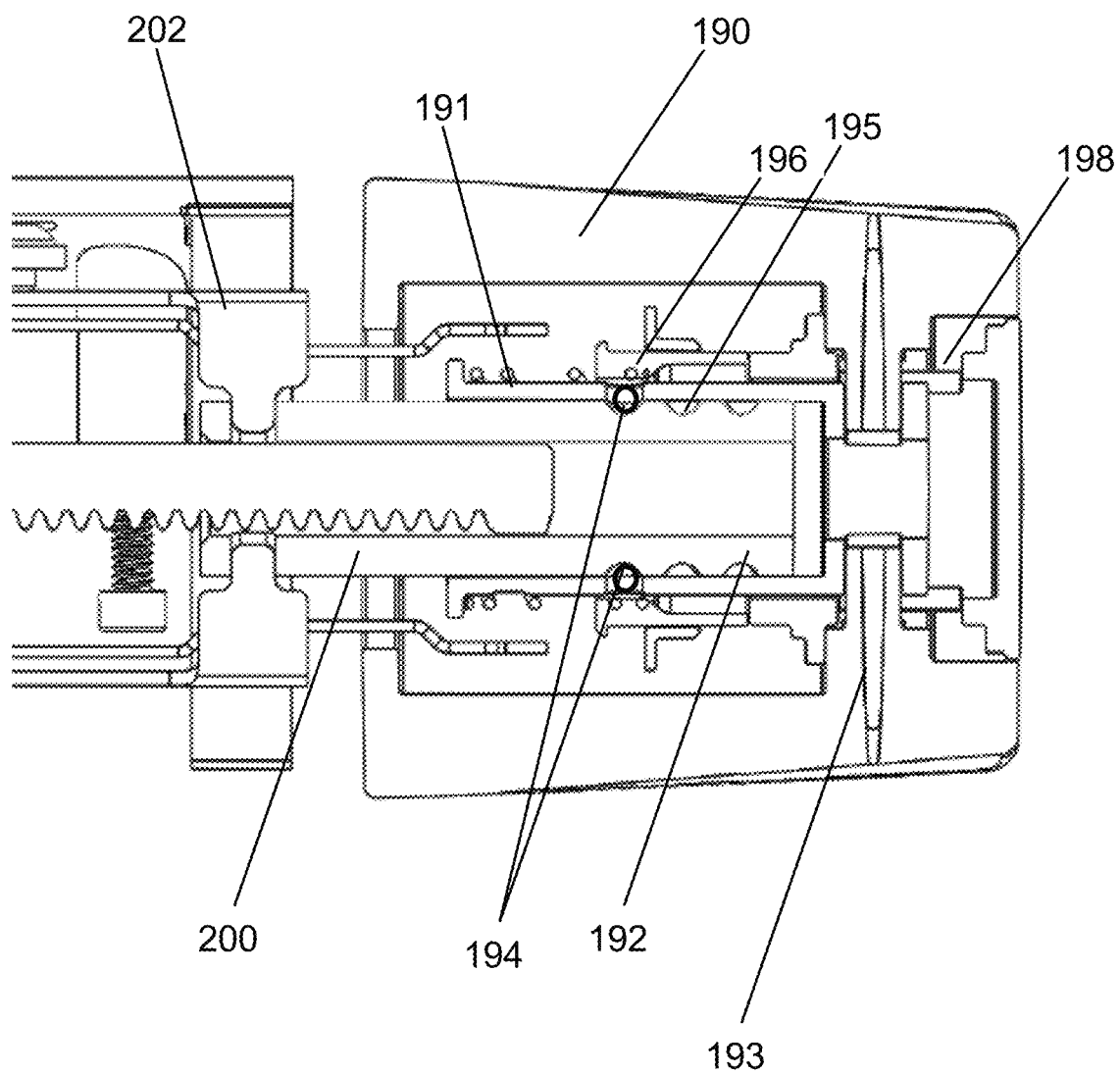
FIG. 12 is a cut-away top view of the articulation mechanism of FIG. 10 in an articulated position.

With reference to FIGS. 11 and 12, the articulation mechanism is coupled to an articulation member extending longitudinally within the reload shaft when the reload shaft is coupled to the handle. Actuation of the articulation mechanism longitudinally translates the articulation member proximally or distally relative to the shaft to articulate the jaw assembly at the distal end of the shaft.

With reference to FIG. 11, the articulation mechanism comprises a ball screw 192 having at least one helical groove or thread 195 in which one or more ball bearing 194 can ride. In the illustrated embodiment, the articulation mechanism comprises two ball bearings 194 that are engageable in two threads 195. The ball bearings 194 are positioned in ball bearing apertures 189 in a ball sleeve 191 positioned radially outwardly of the ball screw 192. The ball bearings 194 are maintained in the threads 195 by a release sleeve 196 positioned radially outward of the ball bearings 194. Rotation of the articulation knob 190, which is coupled to the ball sleeve 191 such as by connecting pins 193, rotates the ball sleeve 191 about an axis of rotation, causing the ball bearings 194 to travel within the threads 195 and correspondingly longitudinally translate the ball screw 192. Articulation of the jaw assembly is accomplished by rotating the articulation knob 190 to correspondingly rotate the ball sleeve 191 and the ball bearings 194 about the axis of rotation while their longitudinal position is fixed along the axis of rotation. The ball bearings 194, which are engaged in the threads 195 of the ball screw 192 will then translate the ball screw 192 forward and reverse along the axis of rotation. In the illustrated embodiment, the ball sleeve 191 is generally tubular, having a cavity formed therein, and a portion of the ball screw 192 is positioned within the cavity and translates longitudinally within the cavity. While the illustrated embodiment of articulation mechanism includes two ball bearings engageable threads in a ball screw, it is contemplated that in other embodiments, the articulation mechanism can have fewer or more than two ball bearings such as, for example, a single ball bearing positioned in a single helical screw or three or more ball bearings in a corresponding number of helical threads.

With reference to FIGS. 11 and 12, the ball screw 192 extends to a distal end 200 coupled to a pair of articulation links 202. The articulation links 202 are spaced apart from one another, which desirably allows them to be positioned radially outwardly of the drive system and actuation shaft within the handle. The distal ends of the articulation links 202 can be rotatably coupled to the articulation adapter 204, which can be positioned coaxially radially outwardly of the actuation adapter at the distal end of the handle. This rotational coupling can include an articulation bearing 205 having relatively low friction properties. This articulation bearing 205 can facilitate rotation of a coupled reload shaft relative to the handle assembly and longitudinal movement of the articulation adapter 204 during operation of the articulation mechanism. While the illustrated embodiment of articulation mechanism includes two articulation links laterally offset from the actuation mechanism within the handle, it is contemplated that in other embodiments, the articulation mechanism can have fewer or more than two articulation links such as, for example, an articulation link or three or more articulation links.

Figure 13:
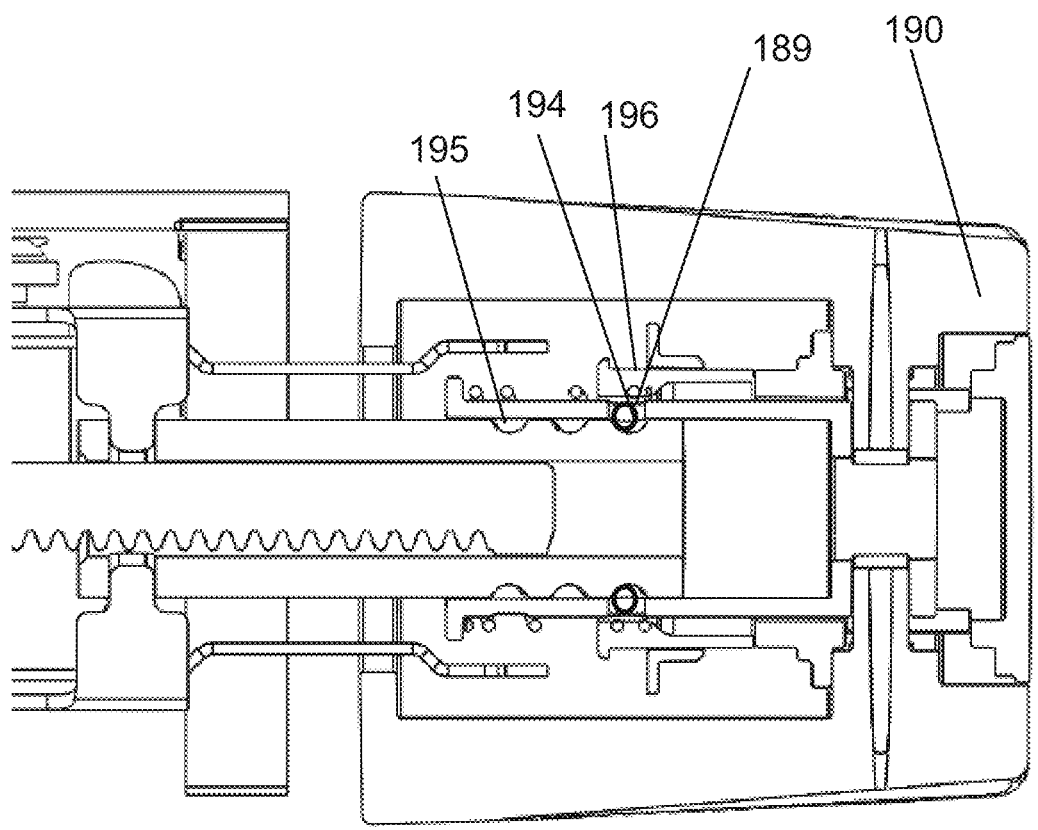
FIG. 13 is a cut-away top view of the articulation mechanism of FIG. 10 in another articulated position.

With continued reference to FIGS. 11-13, the articulation adapter 204 can be connected to the articulation member in the shaft by a bayonet connection when the shaft is coupled to the handle. The threads 195 can be configured such that moving the ball screw proximally will articulate the jaw assembly to the left when viewed from the handle relative to a longitudinally centered position and moving the ball screw 192 distally will articulate the jaw assembly to the right when viewed from the handle relative to the centered position. FIGS. 12 and 13 illustrate the articulation mechanism positioned at the fully articulated configurations defining the ends of an operational range.

Advantageously, since the helical threads 195 of the ball screw 192 are continuous, the articulation mechanism can allow the jaw assembly to be articulated to virtually infinite angular positions between a desired operational range. In some embodiments, the articulation mechanism can be configured to provide an articulation operational range from −45° to +45° of the jaw assembly relative to a longitudinally centered position defined by the longitudinal axis of the shaft. In other embodiments, the articulation mechanism can be configured to provide other operative articulation ranges including ranges providing more than +/−45° of articulation or those providing less than +/−45° of articulation. In some embodiments, the articulation mechanism can be configured to provide articulation in a single direction relative to a longitudinally centered position.

In some embodiments, the pitch of the threads 195 on the ball screw 192 is variable. For example, the threads 195 can include a relatively low pitch towards an end of the threads to advantageously provide a larger mechanical advantage when the jaw assembly can require more force to articulate. The threads 195 can include a relatively higher pitch towards a center of the threads to allow rapid movement with a relatively lower mechanical advantage where the jaw assembly can require a lower force to articulate. In other embodiments, the threads 195 include a constant pitch such that rotation of the articulation knob results in a proportional amount of articulation of a jaw assembly of the stapler that does not vary over the articulation range of the articulation mechanism. Desirably, such a constant pitch thread ball screw can result in an easily predictable response during operation of the actuation mechanism.

Figure 14:
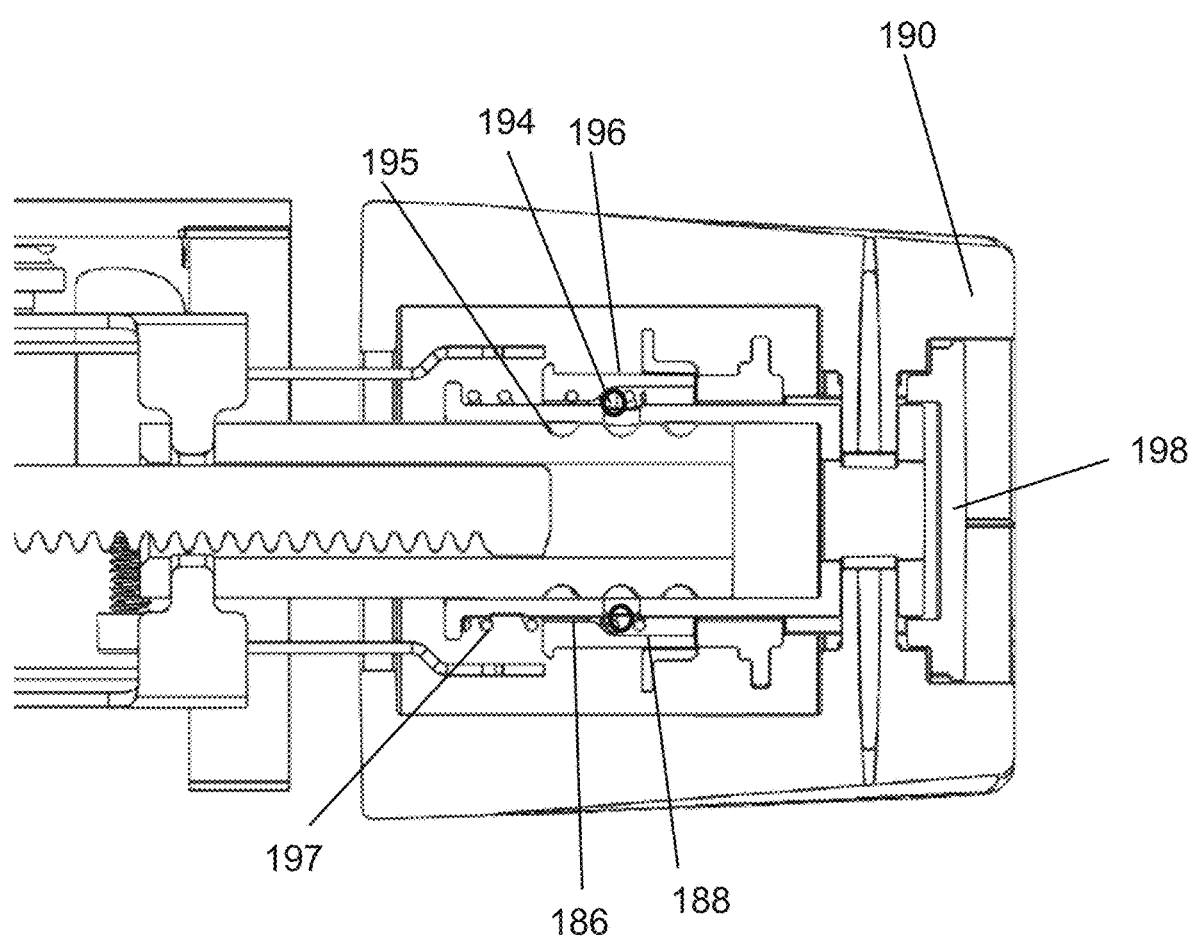
FIG. 14 is a cut-away top view of the articulation mechanism of FIG. 10 in a centered position with a release button actuated.
Figure 15:
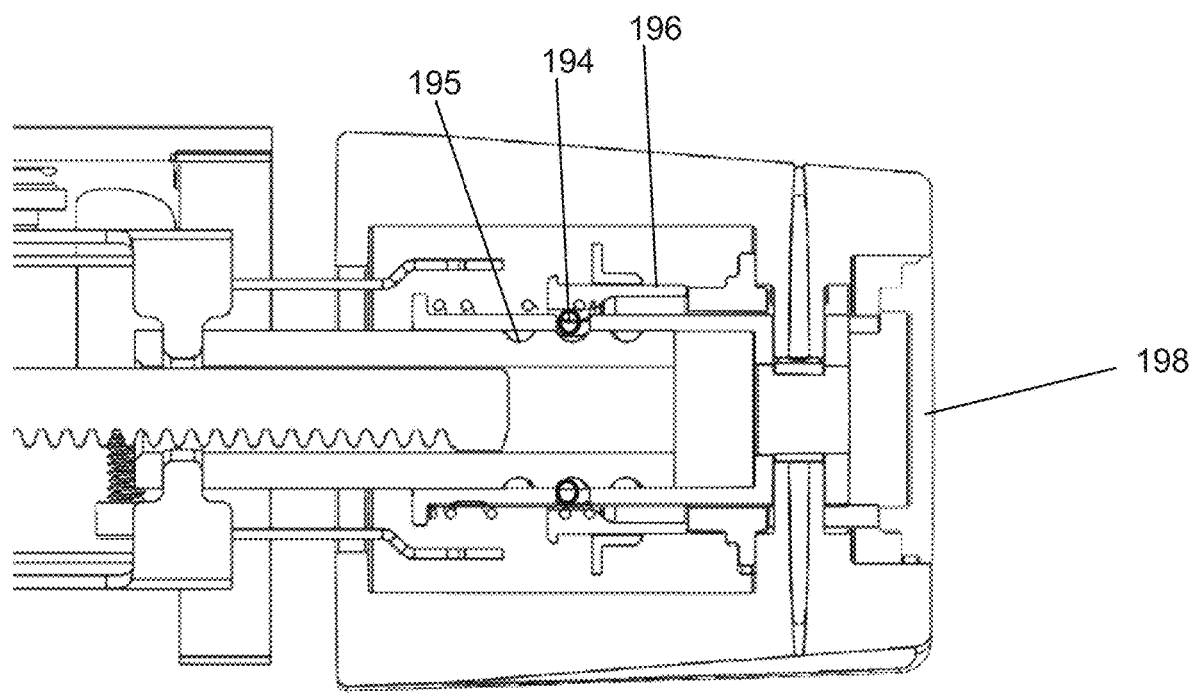
FIG. 15 is a cut-away top view of the articulation mechanism of FIG. 10 in a centered position with a release button actuated.

With reference to FIGS. 14-15, the articulation mechanism can comprise a release mechanism that allows the articulation mechanism to advantageously be reset to the longitudinally centered position from any articulated position. The release mechanism is operated by user pressing a release button 198. In the illustrated embodiment, the release button 198 is positioned radially nested within the articulation knob 190.

With reference to FIG. 14, operation of the release button 198 will distally advance the release sleeve 196. A radially inner surface of the release sleeve 196 is stepped to include an engagement surface 186 having a relatively small inner diameter and a release surface 188 having a relatively larger inner diameter with a smooth ramp between the engagement surface and the release surface. In operation, the engagement surface of the release sleeve maintains the ball bearings 194 in the threads 195 of the ball screw 192. Once the release button 198 is pushed, the engagement surface is distally advanced, allowing the ball bearings 194 to disengage from the threads 195 and advance radially outward through the ball bearing apertures 189 in the ball sleeve against the release surface.

With continued reference to FIG. 14, with the ball bearings 194 disengaged from the threads 195, the articulation mechanism can be biased to a centered position. In some embodiments, the ball screw 192 is biased to a centered position by a biasing member such as two springs and spring force from the shaft. The ball bearings 194 positioned in the centered position along the threads 195 corresponds to a longitudinally centered position of the jaw assembly.

With reference to FIG. 15, once the release button 198 is allowed to return to an undisturbed configuration, release sleeve 196 is retracted proximally by a spring. Proximal movement of the release sleeve 196 forces the ball bearings 194 into engagement with the threads 195 of the ball screw. Thus, the articulation mechanism can then be used to articulate the jaw assembly from the longitudinally centered position, or the stapler can be used with the jaw assembly in the longitudinally centered position.

Figure 16:
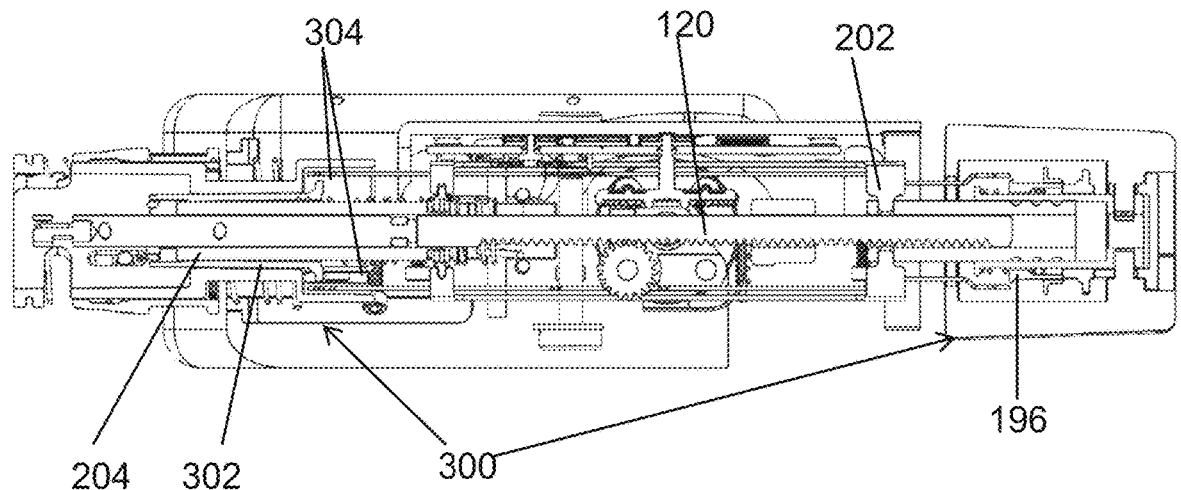
FIG. 16 is a cut-away top view of the powered handle of FIG. 2 with the articulation mechanism in a locked out configuration.
Figure 17:
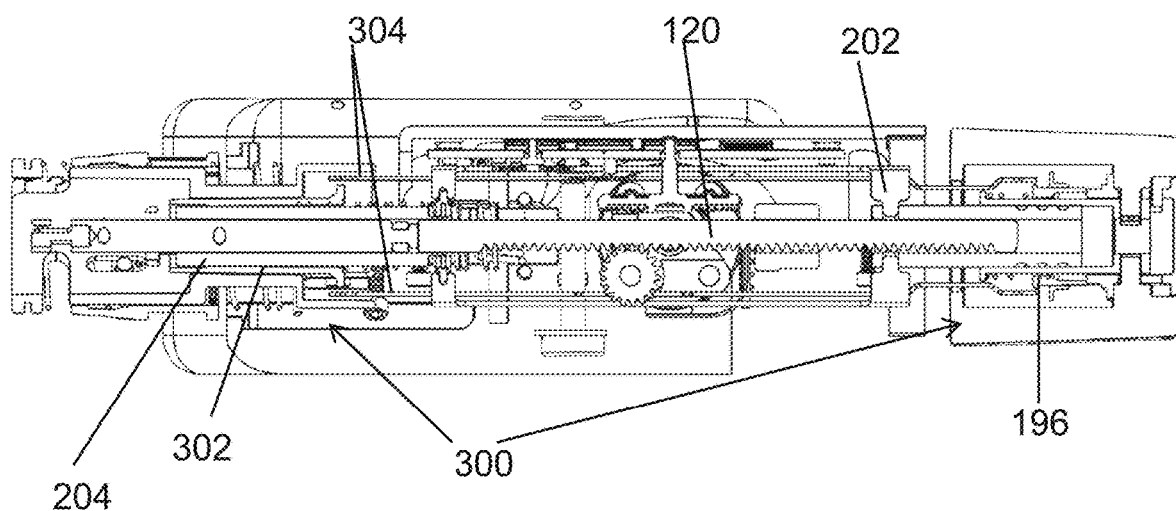
FIG. 17 is a cut-away top view of the powered handle of FIG. 2 with the articulation mechanism in an unlocked configuration.

With reference to FIGS. 16-17, a shaft recognition and articulation lockout mechanism 300 of certain embodiments of articulation mechanism is illustrated. The articulation mechanism can include an articulation lockout mechanism that maintains the articulation mechanism in a centered position if no instrument shaft is coupled to the handle assembly. Thus, a centered position of the articulation adapter 204 is maintained to facilitate the bayonet coupling of instrument shaft and handle assembly previously discussed above. If the articulation mechanism were maintained in an engaged configuration even when no instrument shaft were coupled to the handle assembly, it could be difficult to align the articulation member within the instrument shaft with the articulation adapter 204 in an attempt to couple the instrument shaft with the handle assembly. In the illustrated embodiment of handle assembly, the articulation lockout mechanism can be coupled with a shaft recognition mechanism.

With continued reference to FIGS. 16-17, the shaft recognition and articulation lockout mechanism comprises a lockout sleeve 302 at the distal end of the handle assembly and at least one lockout arm 304 coupled to the lockout sleeve. In the illustrated embodiment, the lockout sleeve 302 can be positioned radially outwardly of the articulation adapter 204. As illustrated, the articulation lockout mechanism comprises two lockout arms 304 extending longitudinally within the handle assembly from a proximal end coupled to the release sleeve 196 to a distal end coupled to the lockout sleeve 302. The lockout arms can be positioned laterally outwardly of the articulation links 202 and the actuation shaft 120 and other drive mechanism components. In other embodiments, one or more than two lockout arms 304 can couple the lockout sleeve 302 to the release sleeve 196, and the lockout arms 304 can be disposed in a different lateral position than in the illustrated embodiment.

In operation, when an instrument shaft is coupled to the handle assembly, the lockout sleeve 302 contacts a boss, tab, collar, or other element at the proximal end of the instrument shaft. This contact translates the lockout sleeve proximally a predetermined amount as the bayonet coupling is engaged. With no instrument shaft coupled to the handle assembly (FIG. 16), the articulation lockout mechanism and release sleeve 196 are configured such that the release sleeve 196 is positioned with the ball bearings against the release surface thereof. Thus, the articulation mechanism is in a locked out configuration. Accordingly, with no instrument shaft coupled to the handle assembly, the articulation knob may be rotated without actuating the articulation mechanism because the ball bearings are disengaged from the threads of the ball screw.

With reference to FIG. 17, once an instrument shaft is coupled to the handle assembly, the articulation lockout mechanism is moved to the engaged configuration. Engagement of the instrument shaft with the lockout sleeve proximally translates the lockout sleeve 302 and lockout arms 304 coupled thereto. The proximal ends of the lockout arms 304 are coupled to the release sleeve 196 of the articulation mechanism such that the proximal movement of the lockout arms 304 advances the release sleeve 196 proximally to engage the ball bearings with the threads of the ball screw. Thus, with an instrument shaft attached, rotation of the articulation knob results in translation of the articulation adapter to articulate an end effector coupled to the instrument shaft.

Figure 18:
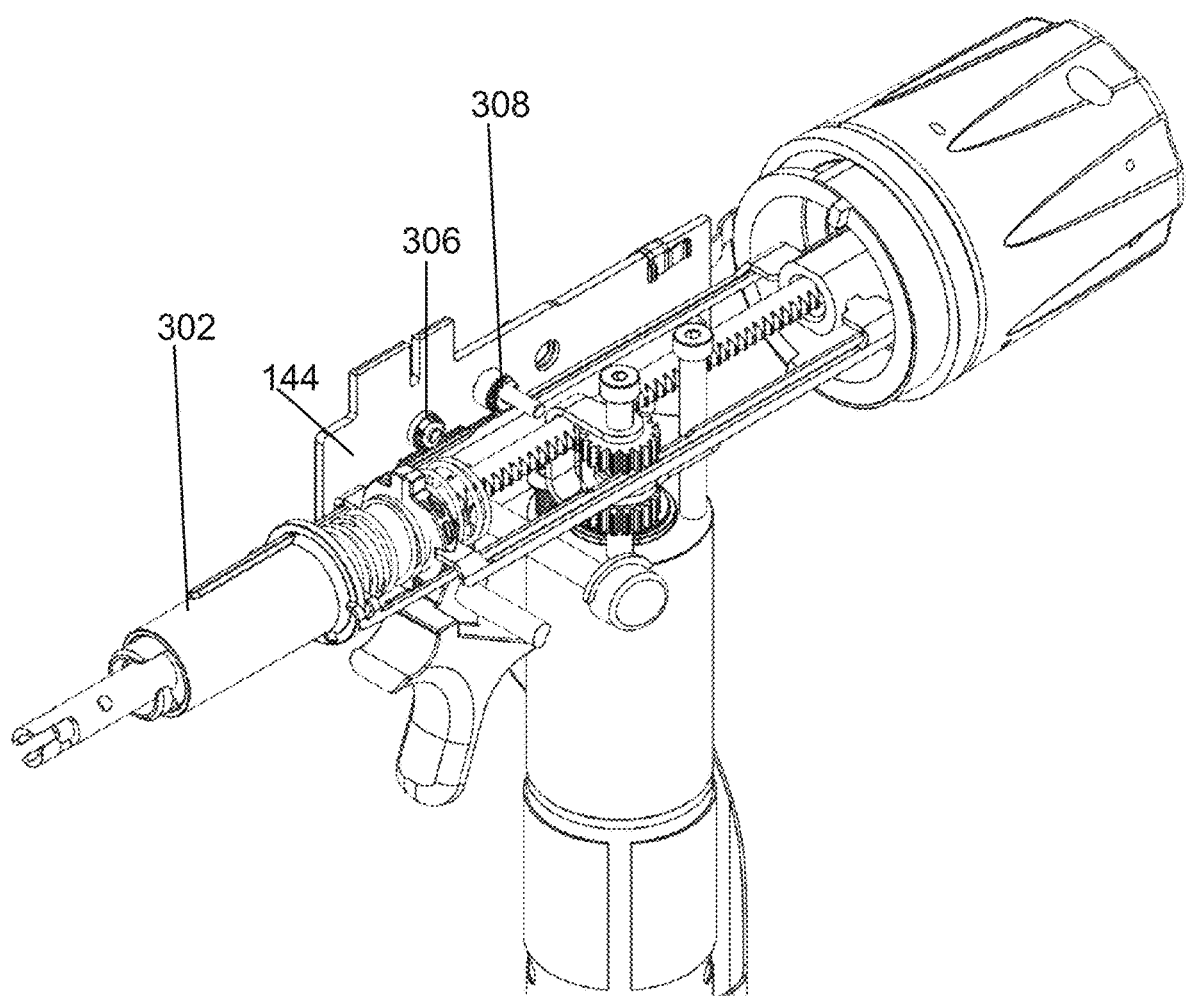
FIG. 18 is a perspective view of the drive system and articulation mechanism of the powered handle of FIG. 2.
Figure 19:
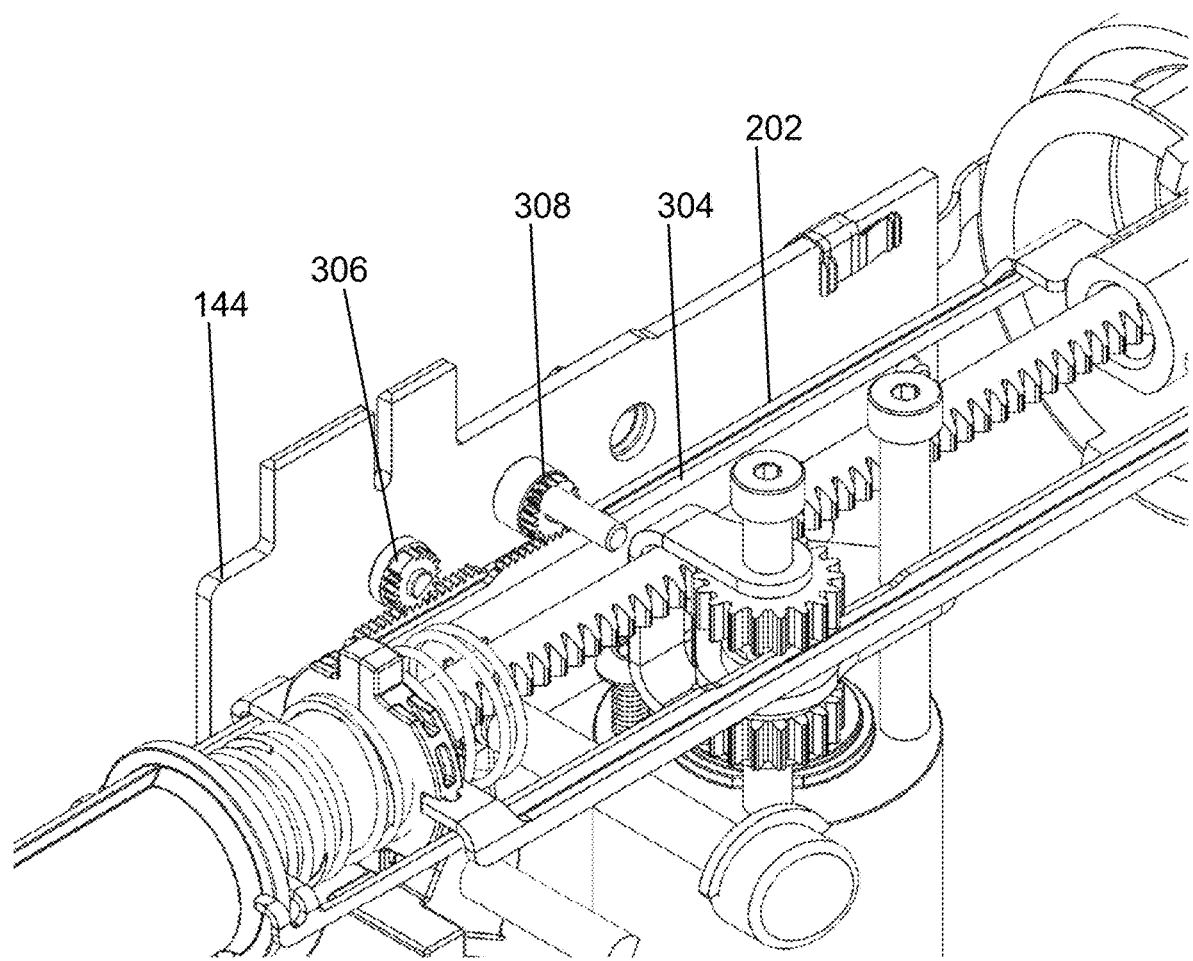
FIG. 19 is a perspective view of the articulation links and lockout links of the articulation mechanism of the powered handle of FIG. 2.

With reference to FIGS. 18 and 19, the articulation mechanism and shaft recognition/articulation lockout mechanism can each comprise a sensor 306, 308 to identify a position of the respective mechanism. In the illustrated embodiment, the sensor of the articulation mechanism comprises a potentiometer in geared engagement with a toothed rack formed on one articulation link 202, and the sensor of the shaft recognition/articulation lockout mechanism can comprise a potentiometer in geared engagement with one lockout arm 304. In some embodiments, the sensors of the articulation mechanism and shaft recognition/articulation latch mechanism can each be mounted on the circuit board 144 on which the control system can be positioned. Thus, one or both of the articulation position and shaft recognition position data can be incorporated by the control system to revise a motor drive profile during an open/close, firing, and return operation of the powered handle. For example, the articulation position can be incorporated by the control system to apply a correction value to a measured actuator rack and actuator position such that certain operational states of the motor can be controlled based on a corrected position of the actuator accounting for a given measured articulation. While the illustrated embodiment includes a potentiometer-based position sensor mechanism, it is contemplated that in other embodiments, other position sensing mechanisms can be used.

Manual Override Return System

With reference to FIGS. 20-27 an embodiment of manual return mechanism for the powered handle is illustrated. A manual return mechanism can advantageously provide a redundant return mechanism in the event of a power supply failure, other powered component failure, or mechanical failure or binding.

Figure 20:
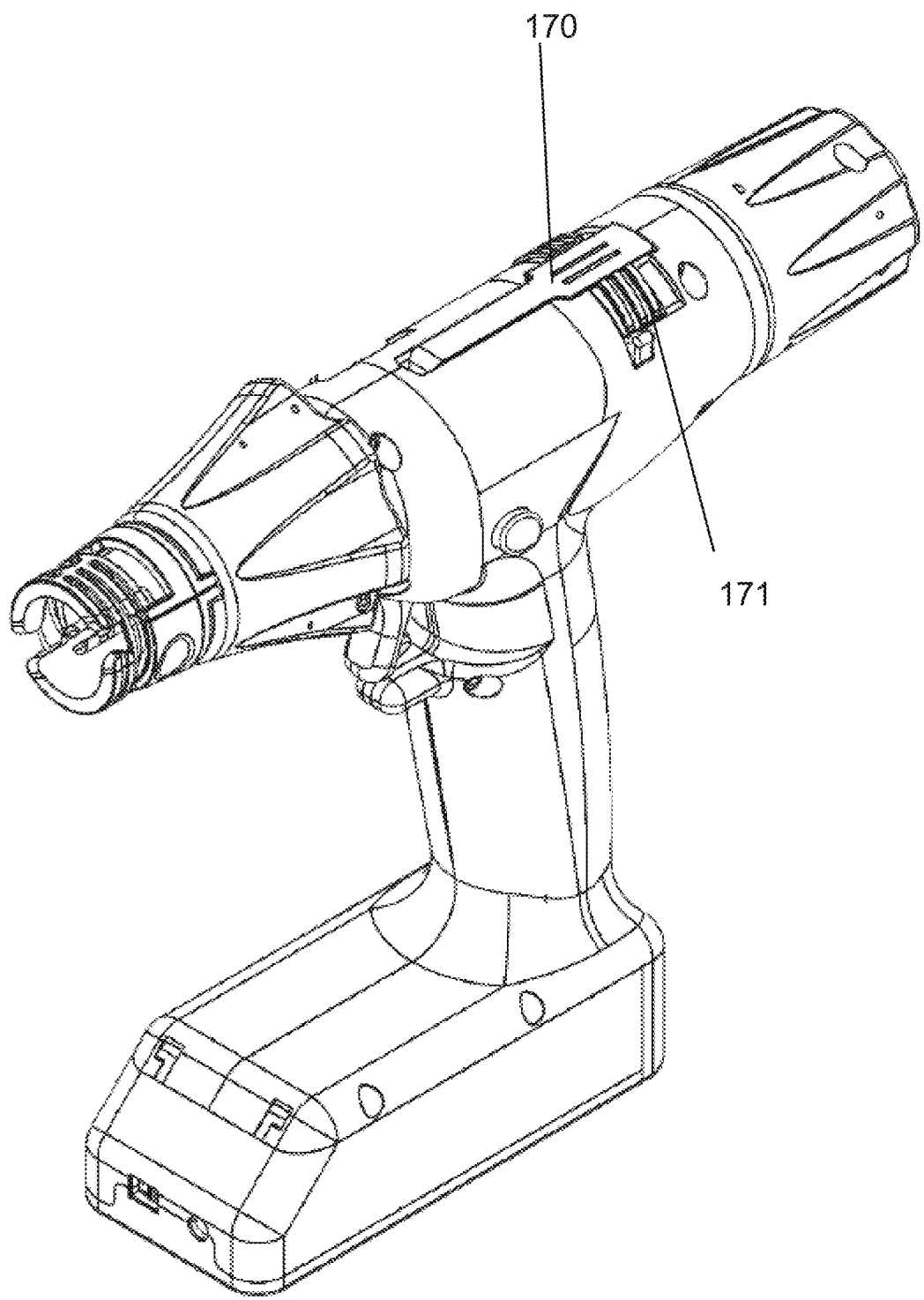
FIG. 20 is a perspective view of the powered handle of FIG. 2 with an override return mechanism in a disengaged configuration.

With reference to FIGS. 20-25, the manual return mechanism includes three separate, independently operable sub-assemblies that are operated in sequence to return the actuation shaft 120 to a proximal-most position within the handle, which corresponds to the open configuration of the jaw assembly. As illustrated, the manual return mechanism 170 comprises a return lock mechanism, a shaft rotation mechanism, and a shaft retraction mechanism. FIG. 20 illustrates the powered handle in a powered operation mode, with the return lock mechanism in a locked configuration. In operation, when it is desirable to manually return the stapler to the open configuration, the return lock mechanism is initially actuated to unlock the manual return mechanism.

Figure 21:
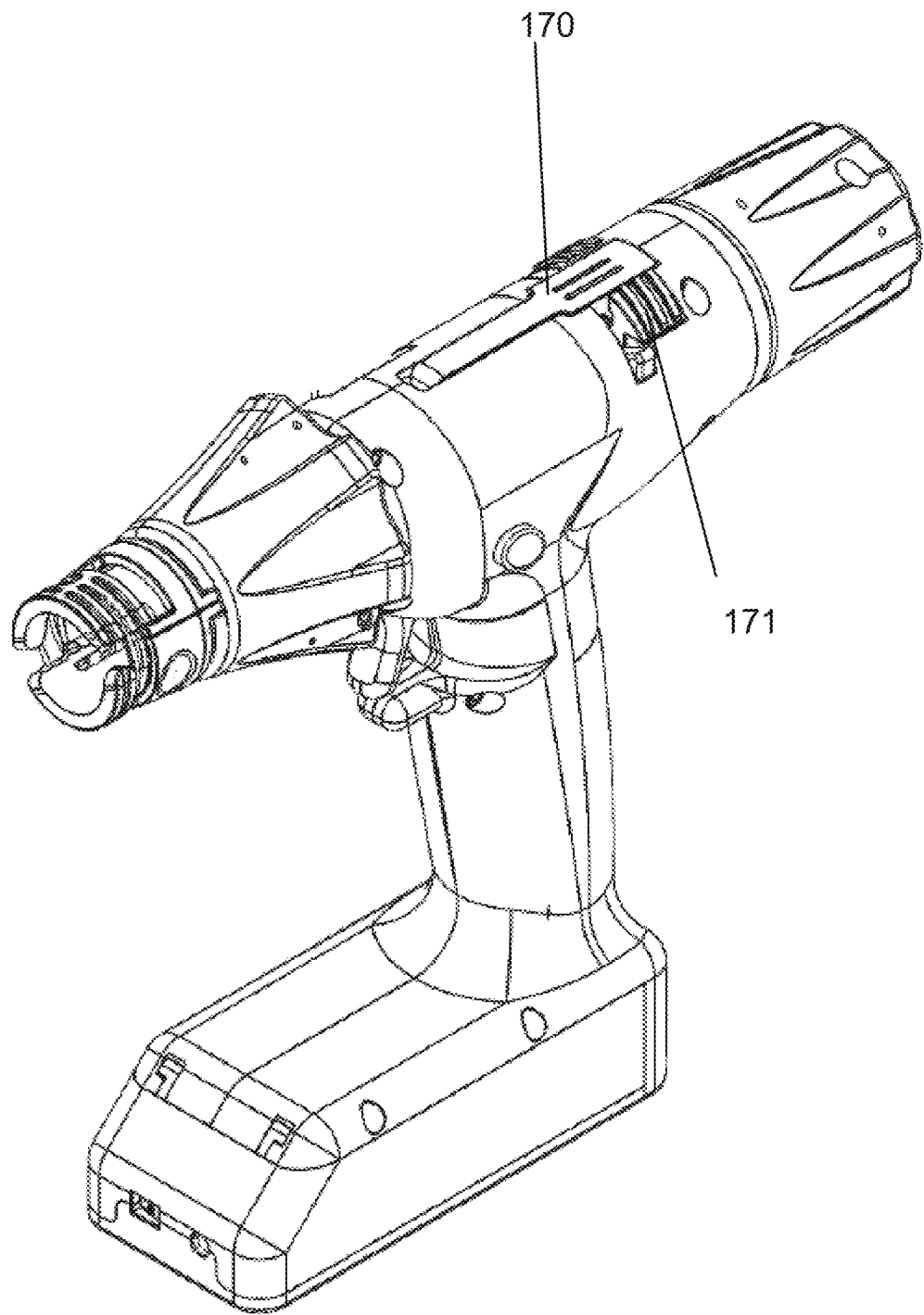
FIG. 21 is a perspective view of the powered handle of FIG. 2 with the override return mechanism unlocked for movement to a return configuration.
Figure 22:
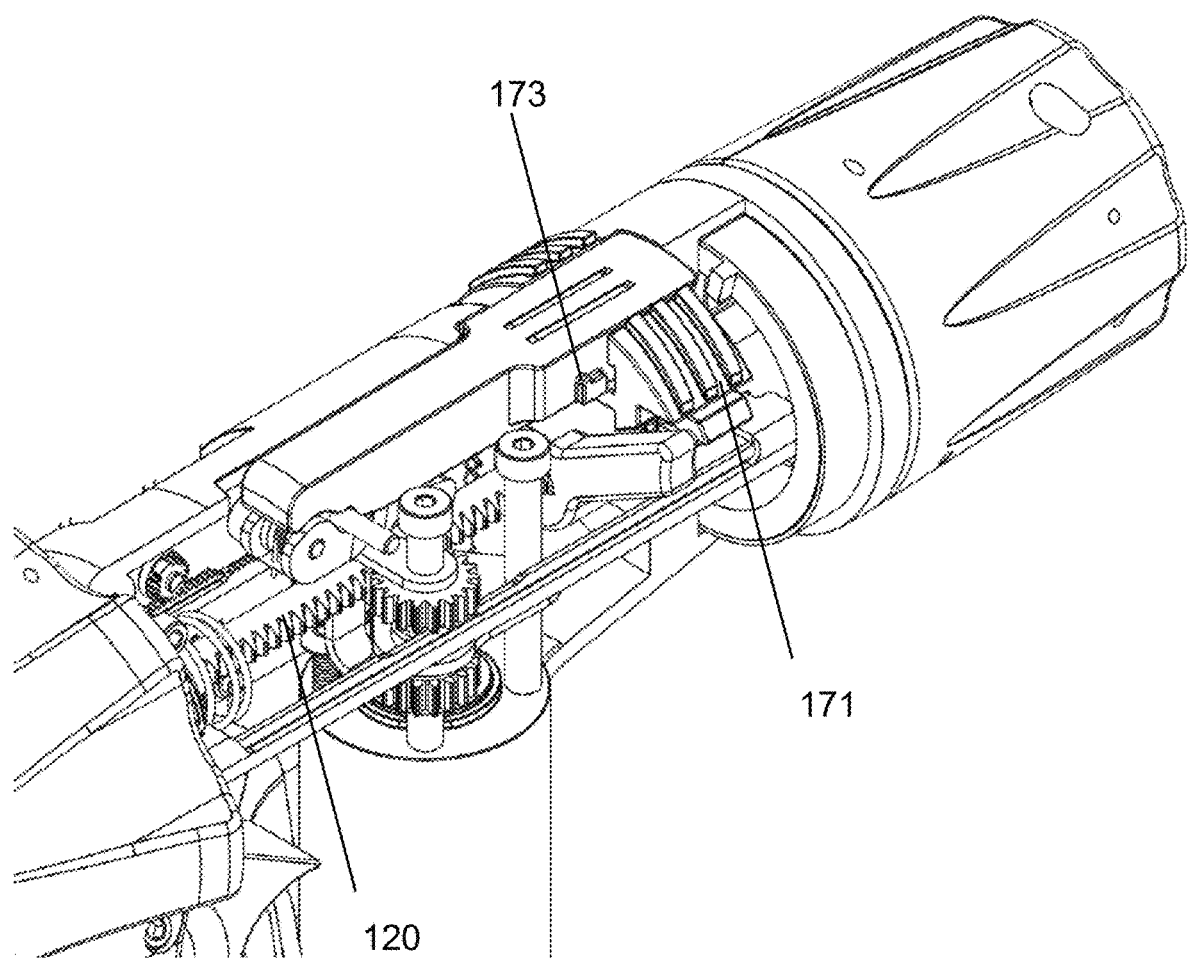
FIG. 22 is a perspective partial cut-away view of the powered handle of FIG. 2 with the override return mechanism unlocked for movement to a return configuration.

As illustrated in FIGS. 21-22, to actuate the return lock mechanism, a return lock 171 is initially slid proximally with respect to the housing of the handle assembly. This movement of the return lock 171 unlocks the shaft rotation mechanism and the shaft retraction mechanism. In the illustrated embodiment, the return lock 171 is moved off of a position in which it interfered with movement of the shaft rotation mechanism, exposing the shaft rotation mechanism for use. Simultaneously, the return lock 171 is disengaged from lock protrusions 173 or tabs on the shaft retraction mechanism allowing the shaft retraction mechanism to pivot away from the handle assembly. A lever of the shaft retraction mechanism can be biased away from the handle assembly, causing it to pivot away from the handle assembly when the return lock is slid proximally.

Figure 23:
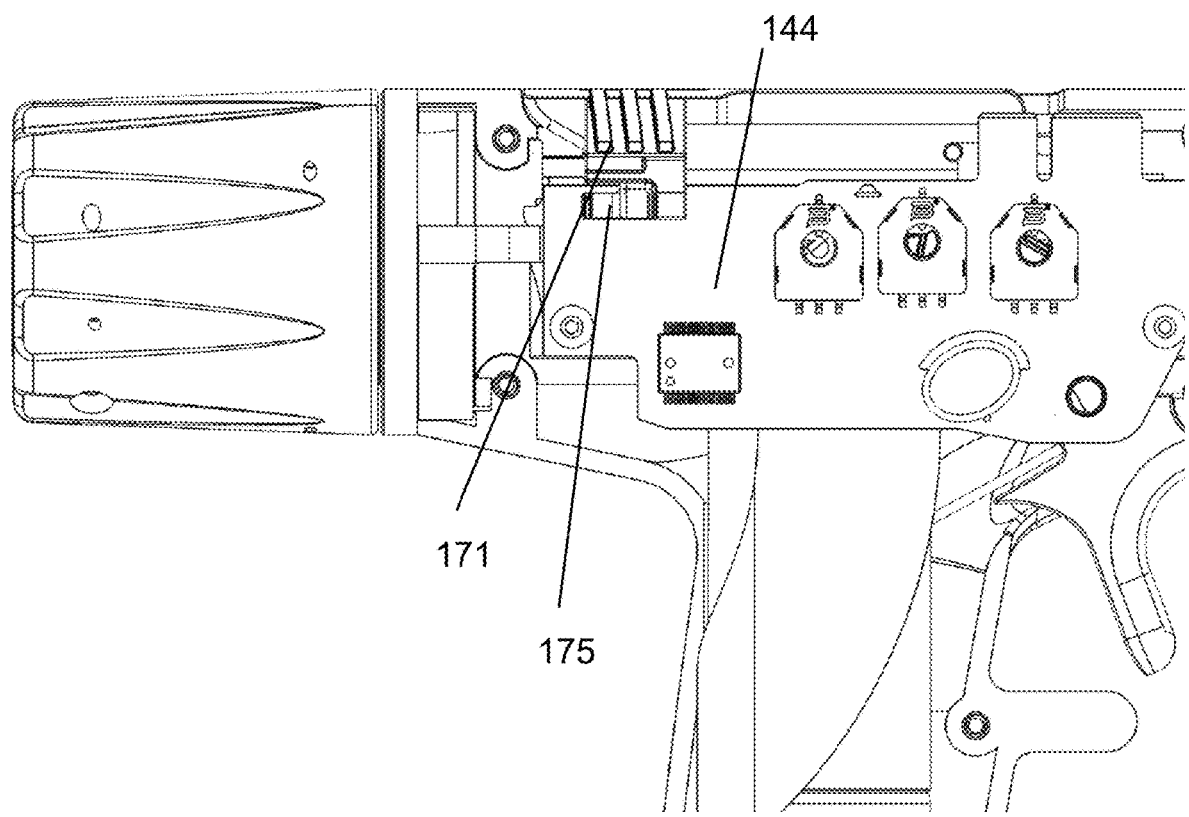
FIG. 23 is a partial cut-away side view of the powered handle of FIG. 2 with the override return mechanism in a disengaged configuration.
Figure 24:
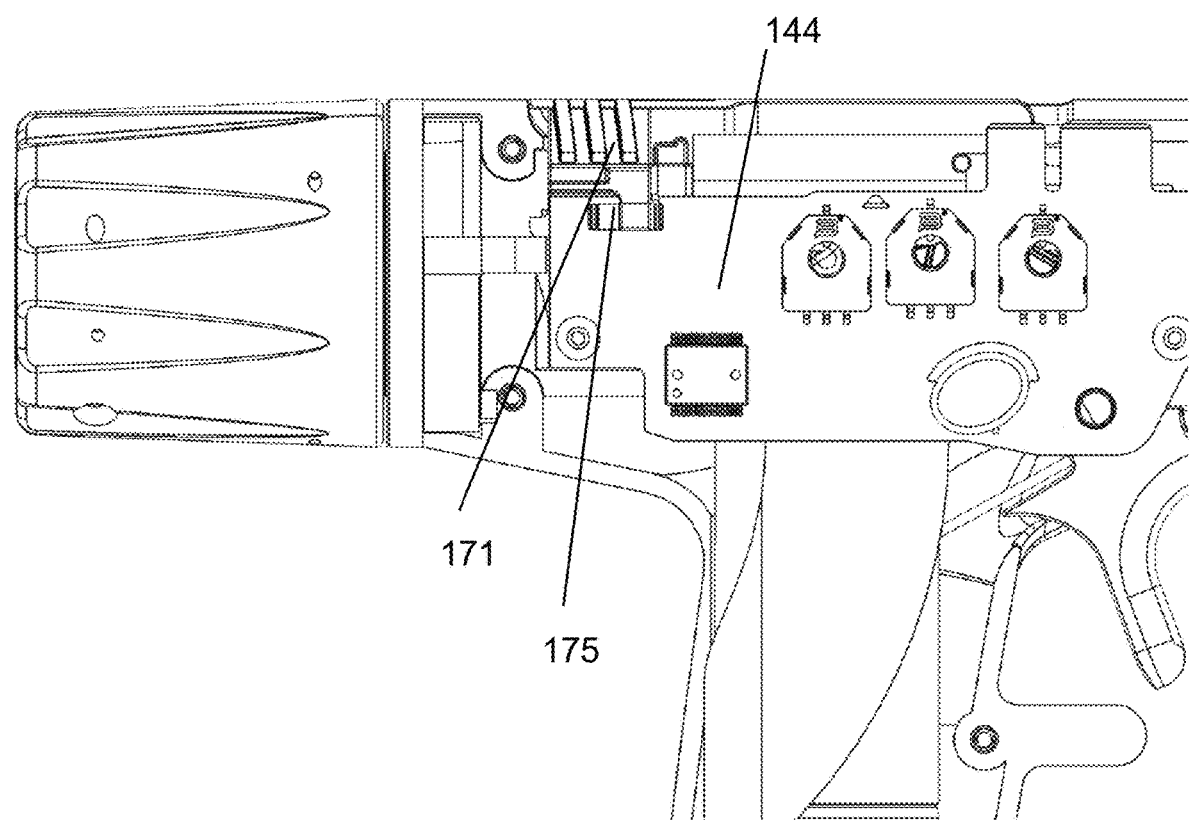
FIG. 24 is a partial cut-away side view of the powered handle of FIG. 2 with the override return mechanism unlocked for movement to a return configuration.

With reference to FIGS. 23 and 24, when the return lock is slid proximally to unlock the return mechanism, the return lock 171 can be electrically coupled to the control unit of the handle assembly to depower the handle assembly. Thus, once the return lock mechanism has been operated, the handle can be disabled from further use even if a user attempts to manually reposition the manual return mechanism and the drive system for repeat use. In the illustrated embodiment, when the handle assembly is configured for powered operation (FIG. 23), the return lock is electrically disengaged from the circuit board 144 having the control unit. When the return lock is slid proximally to unlock the return mechanism, the return lock proximally moves a stamped spring component 175 that electrically engages a circuit on the circuit board 144 to depower the handle assembly. The spring component 175 is configured for proximal movement only, and does not return distally even if the return lock is returned distally to its initial position. Thus, unlocking the return mechanism by sliding the return lock 171 permanently disables the powered functionality of the handle assembly.

Figure 25:
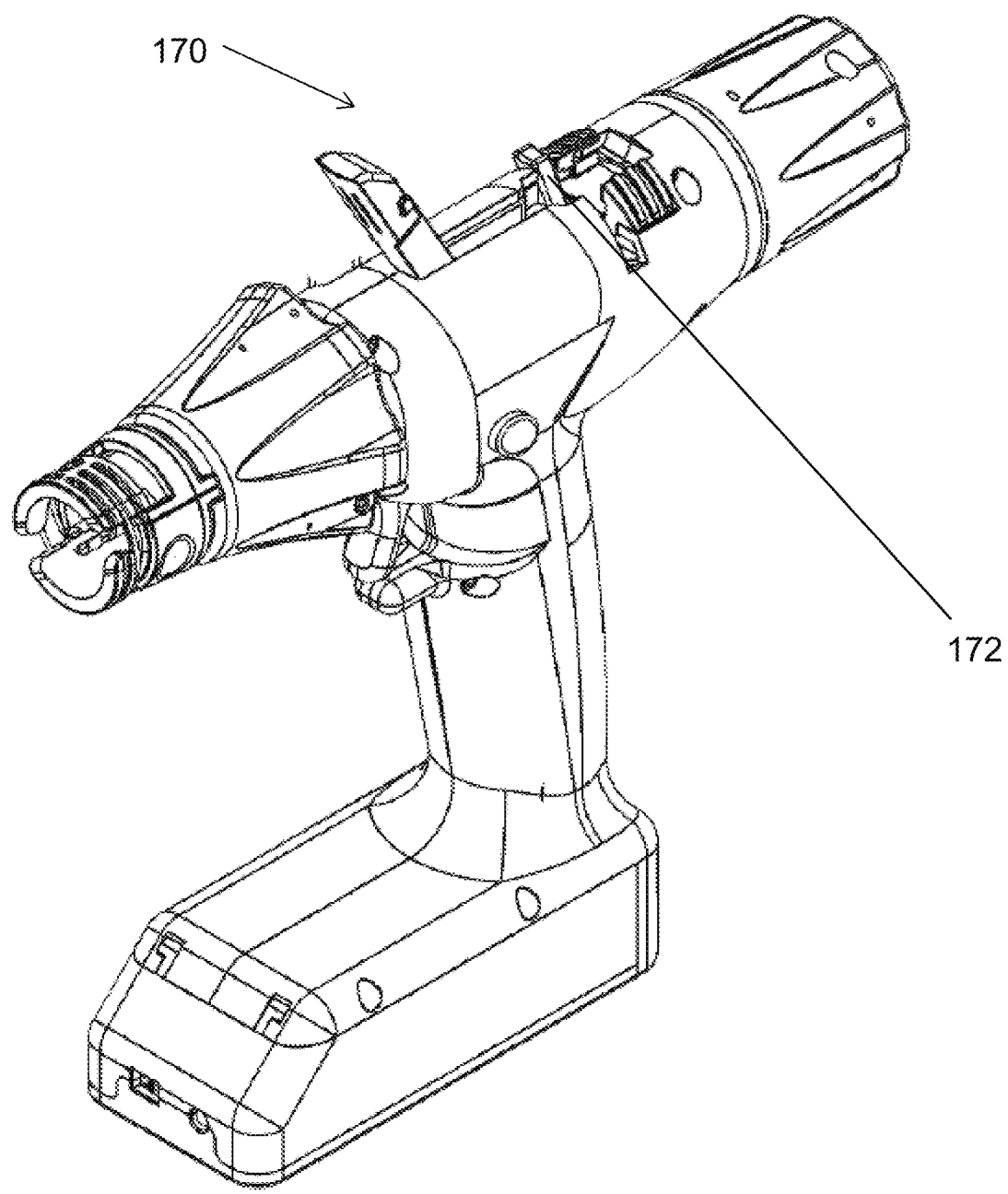
FIG. 25 is a perspective view of the powered handle of FIG. 2 with the override return mechanism in a return configuration.
Figure 26:
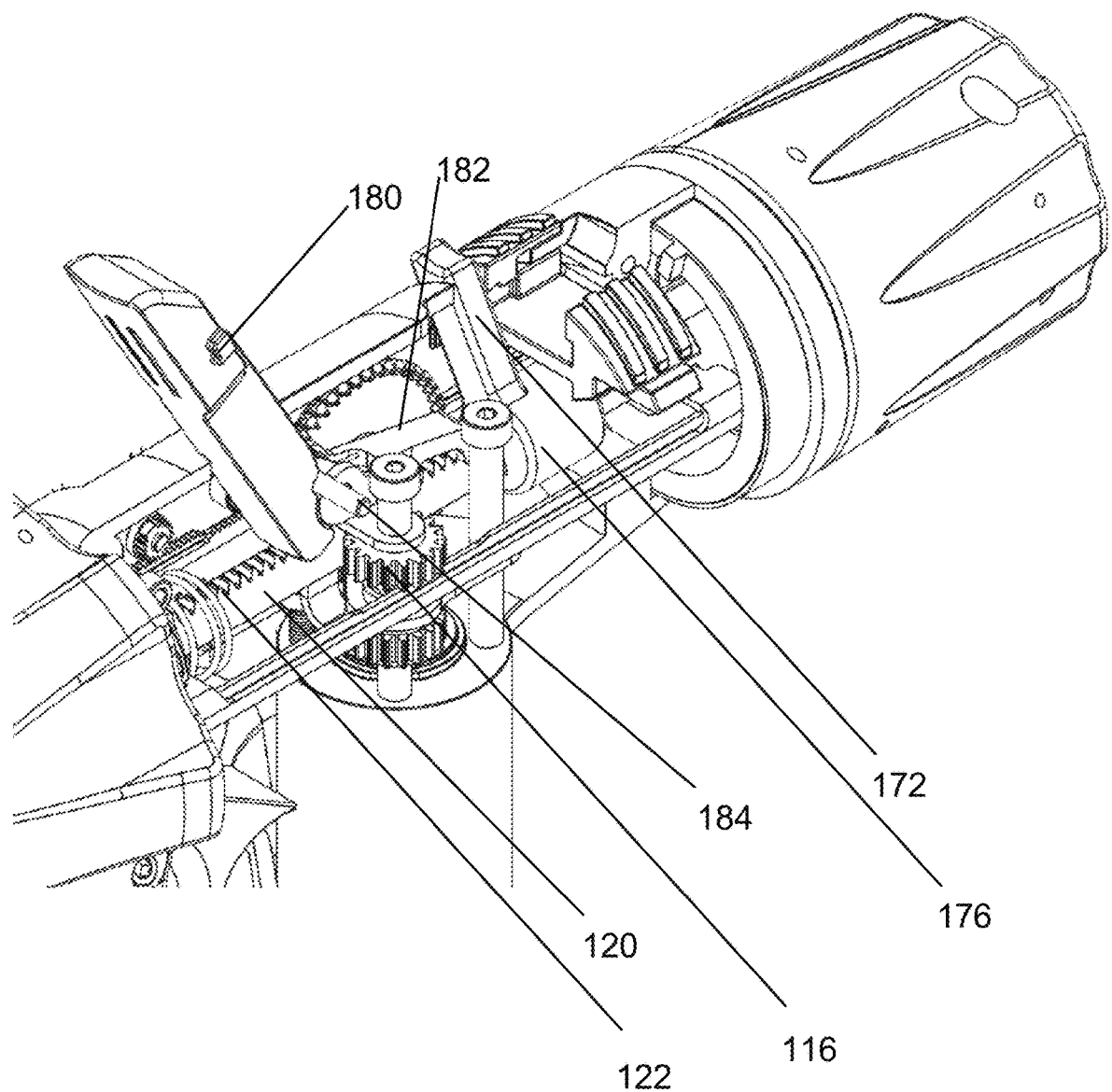
FIG. 26 is a perspective partial cut-away view of the powered handle of FIG. 2 with the override return mechanism in a return configuration.

With reference to FIGS. 25 and 26, to operate the shaft rotation mechanism of the manual return mechanism 170, a user rotates a rotation lever 172 extending to on an outer surface of the handle, now unblocked by movement of the return lock. The rotation lever 172 is coupled to a shaft rotation collar rotationally coupled to the actuation shaft. In the illustrated embodiment, the actuation shaft 120 extends through the shaft rotation collar 176 and is slideable therethrough. Thus, rotating the shaft rotation collar 176 rotates the actuation shaft 120 approximately 90 degrees about the longitudinal axis thereof. This rotation positions the rack 122 of the actuation shaft out of engagement with the auxiliary gear 116 of the drive system. This rotation can be accomplished without affecting the actuation adapter since the actuation shaft 120 is rotatably coupled to the actuation adapter (FIG. 5).

While the illustrated embodiment includes a shaft rotation mechanism having a rotation lever 172 rotated by a user, in other embodiments, the shaft rotation mechanism can be configured to self-deploy upon proximal movement of the return lock. For example, a self-deploying shaft rotation mechanism can include a shaft rotation collar having a torsional bias. In certain embodiments, the shaft rotation collar is coupled to the handle assembly by a torsion spring. When the return lock is slid proximally, the torsional bias of the shaft rotation tends to rotate the actuation rack to disengage the actuation rack from the auxiliary gear and to engage the actuation rack with the shaft retraction mechanism.

Figure 27:
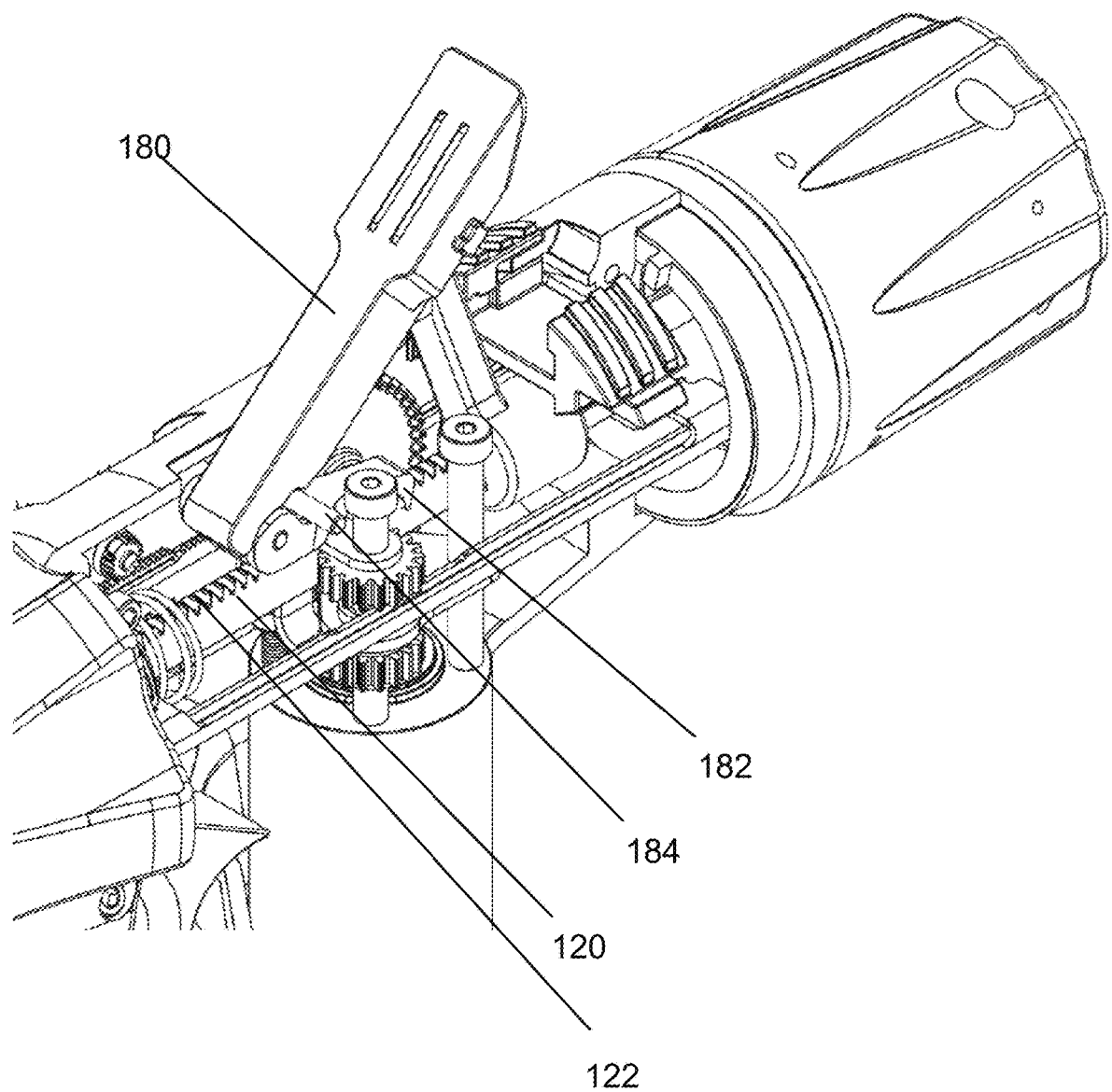
FIG. 27 is a perspective partial cut-away view of the powered handle of FIG. 2 with the override return mechanism in a return configuration and a manual return cycle initiated.

With reference to FIGS. 26 and 27, once the shaft rotation mechanism has been operated, the shaft retraction mechanism can be operated to return the actuation shaft proximally within the handle. Sliding the return lock proximally within the handle assembly unlocks a return lever 180 on the powered handle. The return lever 180 is pivotably coupled to a return pawl 182 at a pivot joint 184. When the rack 122 of the actuation shaft 120 was rotated out of engagement with the drive system, it was rotated into engagement with the shaft retraction mechanism. The return lever 180 can be rotated through one or a series of return cycles (FIGS. 26, 27) to engage the return pawl 182 with the rack 122 on the actuation shaft 120 and retract the actuation shaft 120 proximally within the handle in a ratchet-type operation.

Figure 27A:
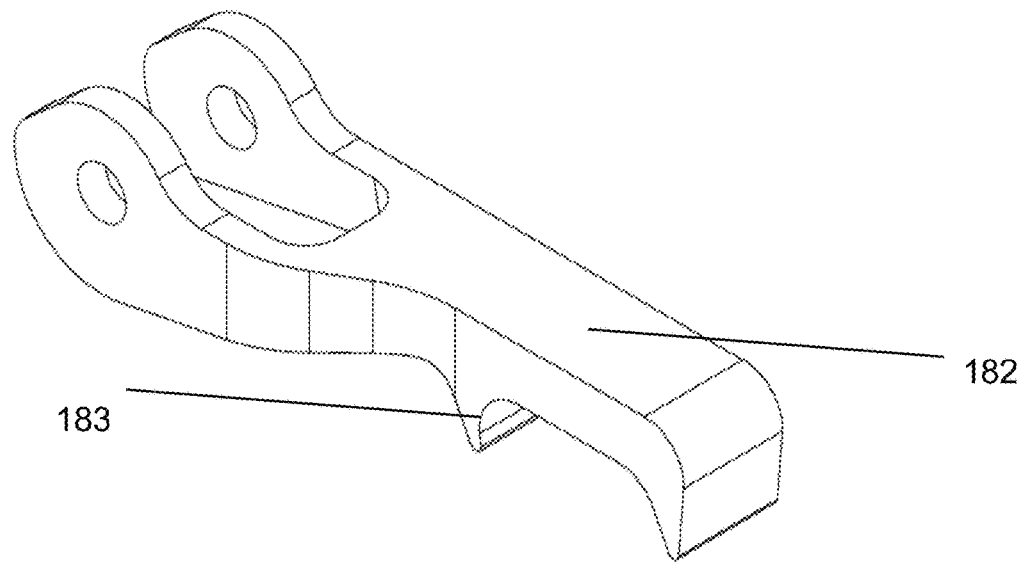
FIG. 27A is a perspective view of a return pawl of the override return mechanism of the powered handle of FIG. 2.
Figure 27B:
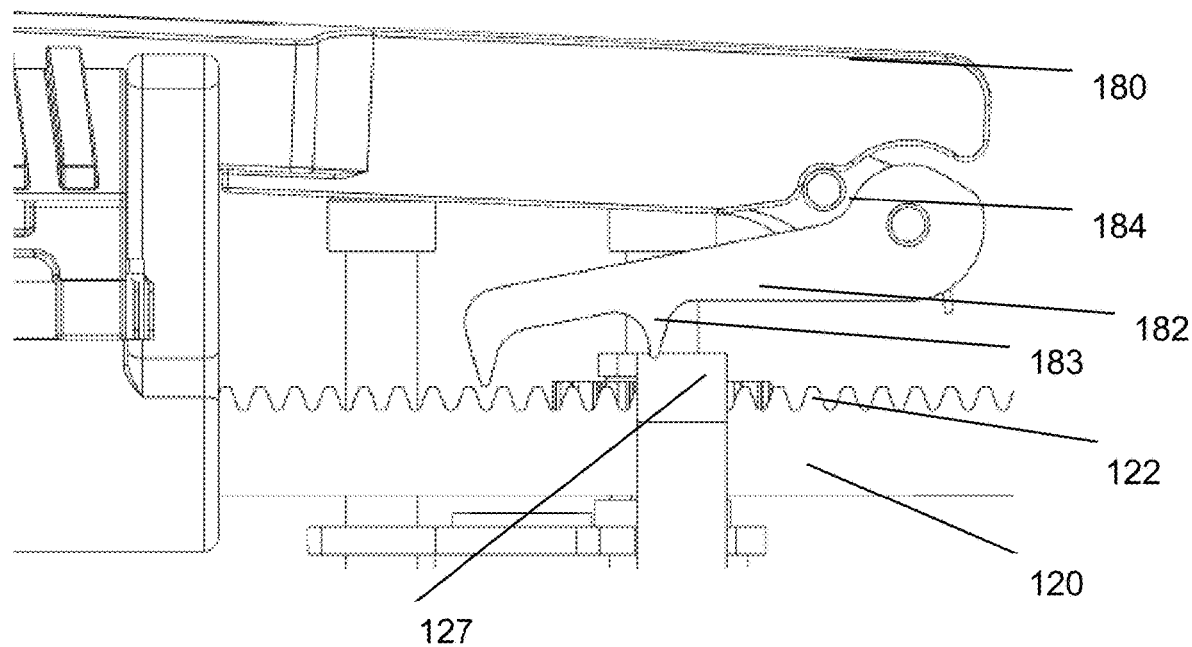
FIG. 27B is a side view of the override return mechanism of the powered handle of FIG. 2.
Figure 27C:
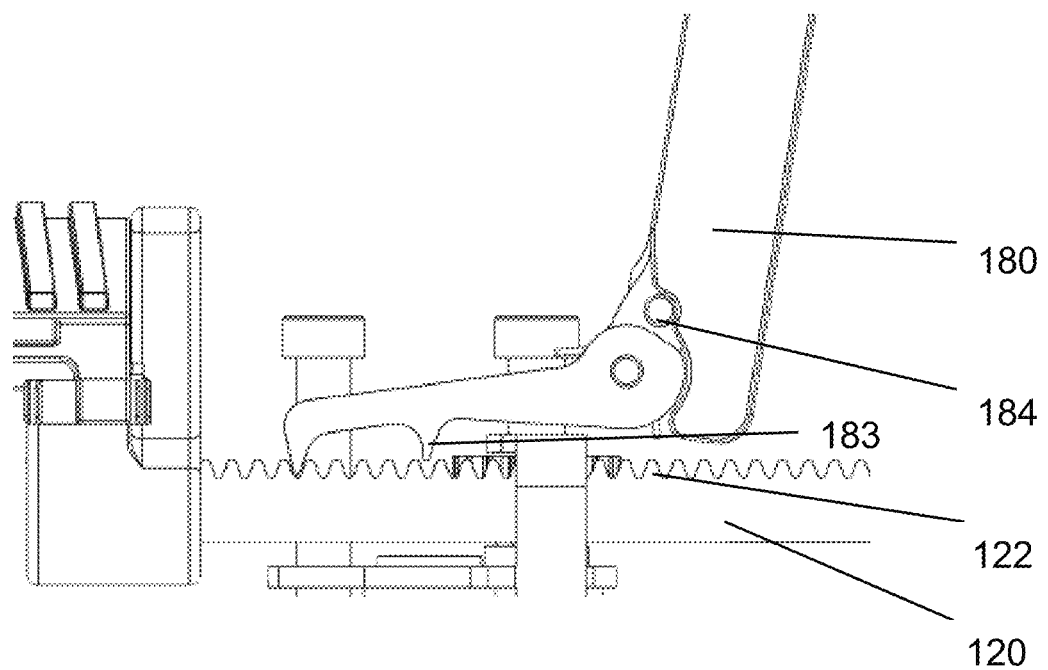
FIG. 27C is a side view of the override return mechanism of the powered handle of FIG. 2.
Figure 28:
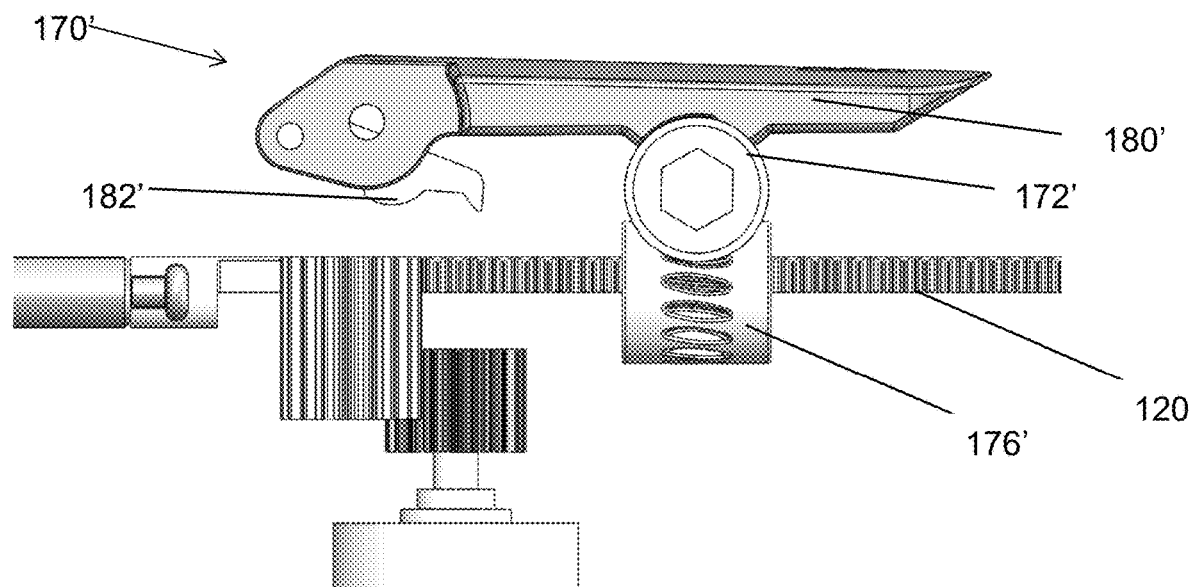
FIG. 28 is a side view of another embodiment of override return mechanism for a surgical stapler.
Figure 29:
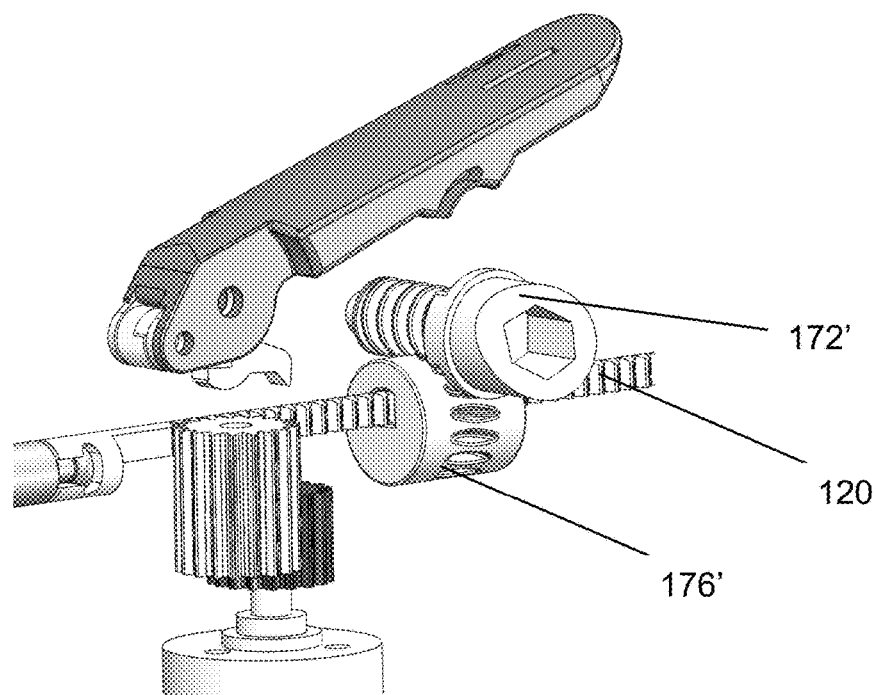
FIG. 29 is a perspective view of the override return mechanism of FIG. 28.
Figure 30:
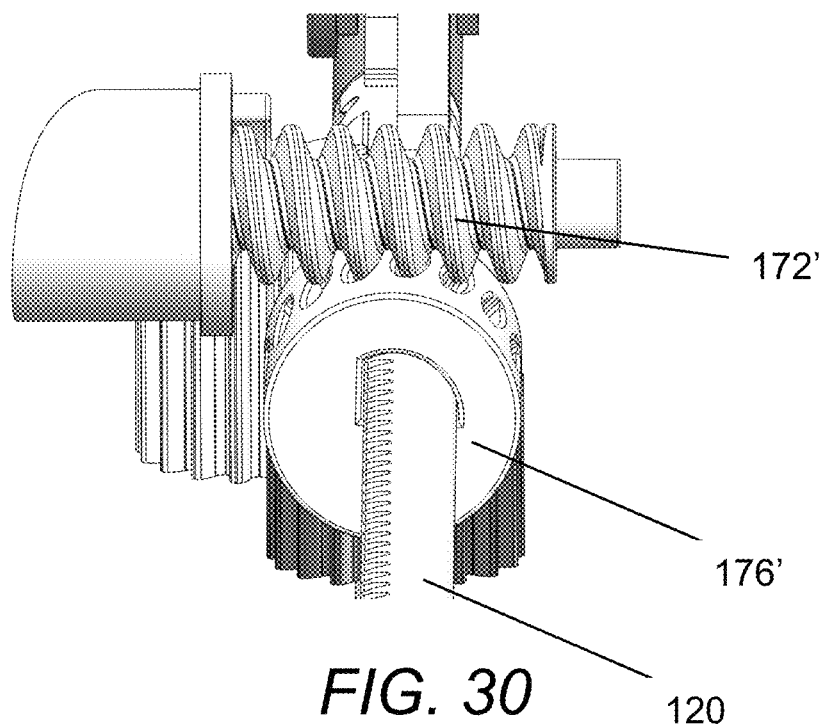
FIG. 30 is a perspective view of the override return mechanism of FIG. 28.

With reference to FIGS. 27A-27C, the return pawl 182 can be configured to facilitate actuation shaft retraction. In the illustrated embodiment, the return pawl 182 comprises a protruding boss or second pawl tooth 183 that is positioned to interact with the guide member 127 of the motor mount during a portion of the return cycle. When the second pawl tooth 183 contacts the guide member 127, the return pawl 182 is limited from engaging the rack 122 of the actuation shaft 120 (FIG. 27B). Desirably, the second pawl tooth 183 can be positioned to limit engagement of the return pawl 182 with the rack 122 during a portion of the return cycle where a user would otherwise have relatively low mechanical advantage. As illustrated, the second pawl tooth 183 prevents the return pawl 182 from engaging the rack 122 until the return lever 180 is positioned at a predetermined angle relative to a longitudinal axis of the actuation shaft 120 to provide a desired mechanical advantage (FIG. 27C).

Figure 31:
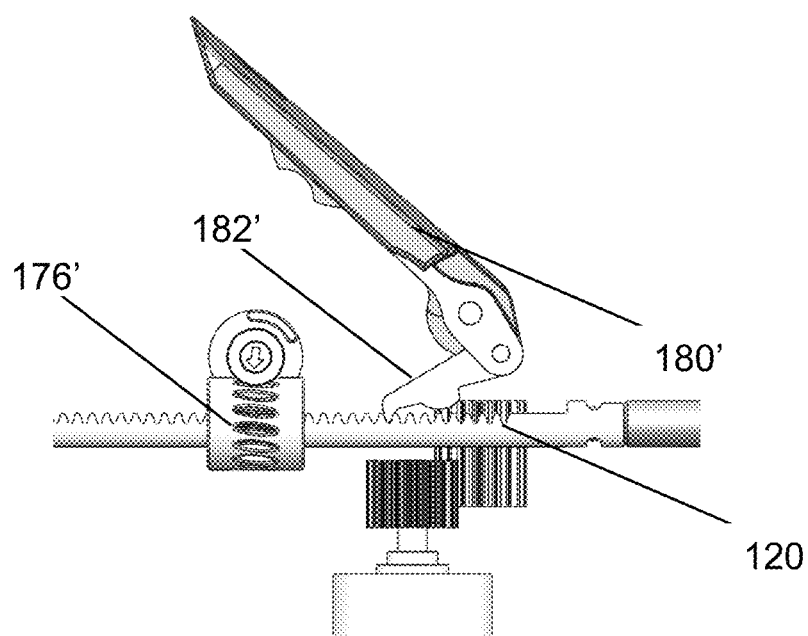
FIG. 31 is a side view of the override return mechanism of FIG. 28.

With reference to FIGS. 28-31, another embodiment of manual return mechanism for the powered handle is illustrated. The components and operation of the manual return mechanism 170' are similar to that described above with respect to the manual return mechanism 170 of FIGS. 20-27. However, in use of the manual return mechanism 170', the return lock and shaft rotation mechanism functionality can be provided by a worm gear-driven a shaft rotation collar 176'. Thus, a user can initially rotate the actuation shaft 120 away from the powered drive system by rotating a worm gear drive such as, for example, with a hexagonal key. Through rotation of the worm gear, the shaft rotation mechanism releases a shaft retraction mechanism, disengages the actuation rack from the powered drive, and positions the actuation rack into engagement with the shaft retraction mechanism (FIG. 31). The shaft retraction mechanism of the manual return mechanism 170' includes similar ratchet-type operation with a return lever 180' pivotably coupled to a return pawl 182' as that discussed above with respect to the manual return mechanism 170.

Two-Position Lockout Mechanism

Figure 32:
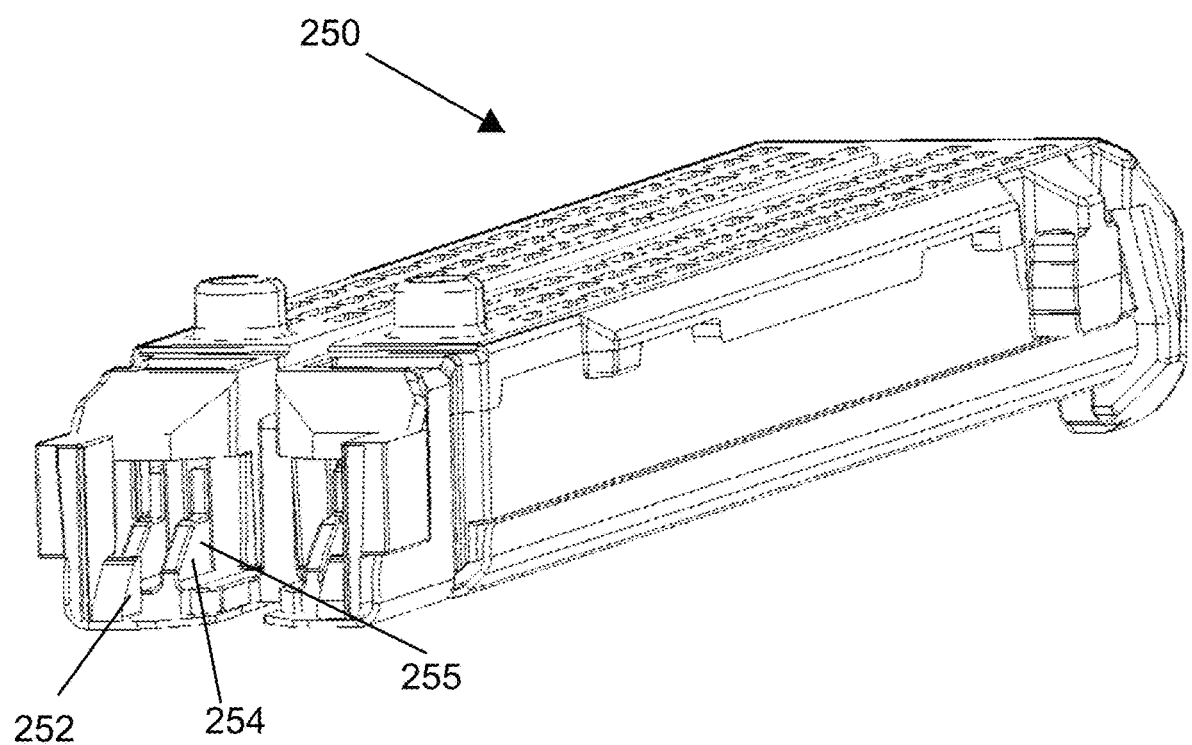
FIG. 32 is a perspective view of a reload cartridge for use in certain embodiments of surgical stapling device.

With reference to FIG. 32, a reload cartridge 250 for use with an elongate shaft of a surgical stapler device having separate empty jaw assembly and fired reload lockout mechanisms is illustrated. As further described below, if no reload cartridge 250 is present in the jaw assembly and a user attempts to grasp the jaw assembly in an open-close stroke, a two-position lockout lever will move to a first, locked position. As illustrated, the reload cartridge includes a first lockout actuator sized and positioned to position a two-position lockout lever in a second position to defeat the empty jaw assembly lockout mechanism when a reload is positioned in the reload support of the jaw assembly. The first lockout actuator can comprise a ramped boss 252 extending laterally inwardly from a side wall of a body of the cartridge.

With continued reference to FIG. 32, in the illustrated embodiment the reload cartridge 250 includes a second lockout actuator sized and configured to position a two-position lockout lever in an unlocked position to defeat the fired reload lockout mechanism when an unfired reload is positioned in the jaw assembly. Thus, in addition to the two lockout positions, the two-position lockout lever is pivotable to an unlocked position. In certain embodiments, the second lockout actuator comprises a tail 254 extending proximally from a slider 255 of the reload cartridge 250. When the reload cartridge 250 is in an unfired state, the slider 255 is in a proximal position such that the slider tail 254 extends proximally to engage the lockout lever. As the firing member is advanced distally in a firing stroke, it abuts the slider within the reload cartridge and advances the slider distally. Thus, once the reload cartridge 250 is in a partially fired (or fully fired) state, the proximally-extending slider tail 254 is not in position to defeat the fired reload lockout mechanism.

Figure 33:
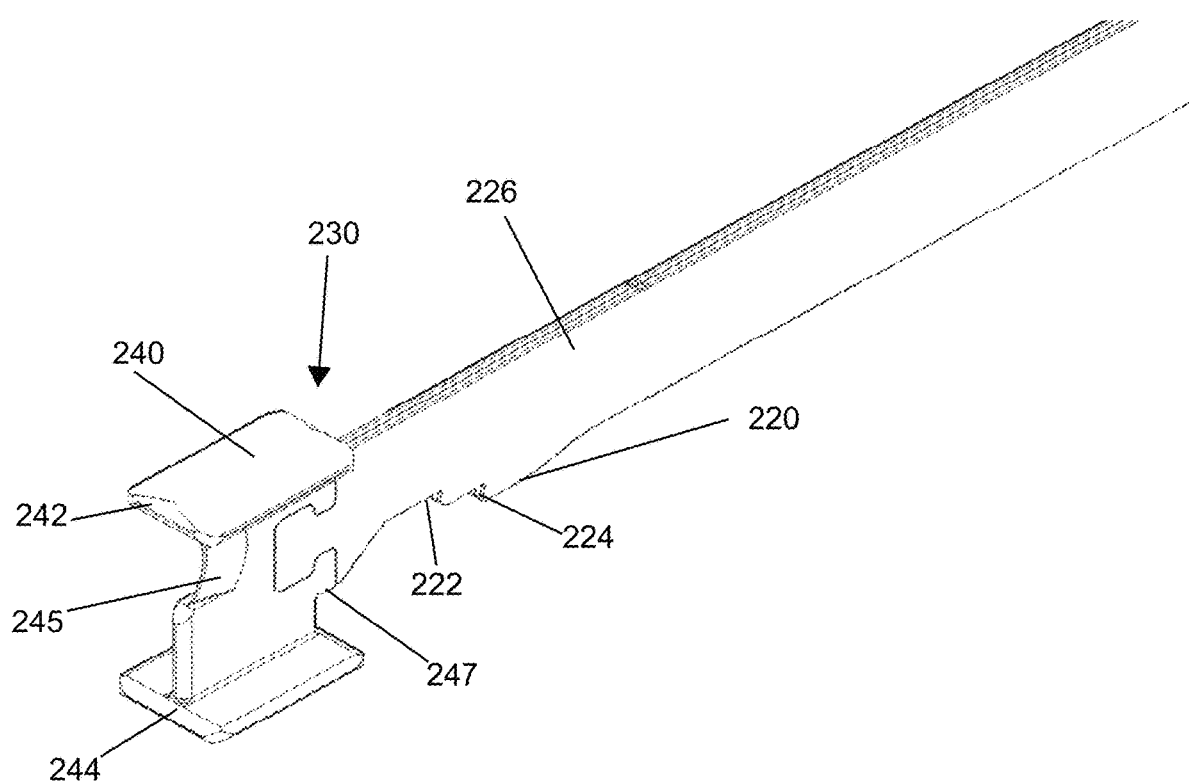
FIG. 33 is a perspective view of a firing beam and firing member for use in certain embodiments of elongate shaft assembly of a surgical stapling device.

With reference to FIG. 33, a firing beam 226 for use with an elongate shaft assembly of a surgical stapler device having separate empty jaw assembly and fired reload lockout mechanisms is illustrated. The firing beam 226 extends from a proximal end to a distal end 230. A firing member 240 having a generally I-beam configuration is disposed at the distal end 230 of the firing beam 226. Upper and lower horizontal flanges 242, 244 of the I-beam firing member 240 ride in channels in the first and second jaws of the jaw assembly to approximate the jaws, then maintain spacing of the jaws during staple firing. A cutting blade 245 is positioned on the vertical portion of the I-beam profile to transect tissue between rows of staples. The I-beam firing member 240 can be attached to the distal end of the firing beam 226 by an interlock fit, welding, another joining technique, or some combination thereof. A proximal edge of the I-beam firing member 240 can have a proximally-extending projection or tail 247 that can rest on a proximal portion of a lockout lever with the firing beam 226 in a fully retracted position corresponding to an open jaw assembly.

With continued reference to FIG. 33, the firing beam can include a first lockout notch 222 for use in conjunction with the empty jaw assembly lockout mechanism and a second lockout notch 224 for use in conjunction with the fired reload lockout mechanism. In the illustrated embodiment, the first lockout notch 222 extends a first height from an adjacent lower edge 220 of the firing beam 226. As further described below, the first height is selected to correspond to a height of the proximal end of the lockout lever when the empty jaw assembly lockout has been actuated by an attempt to approximate a jaw assembly without a reload cartridge present.

With continued reference to FIG. 33, in the illustrated embodiment, the second lockout notch 224 is positioned on the firing beam proximal of the first lockout notch 222. The second lockout notch 224 extends a second height from the adjacent lower edge 220 of the firing beam 226. As further described below, the second height is selected to correspond to a height of the proximal end of the lockout lever when the fired reload lockout mechanism has been actuated by an attempt to fire a previously fired or partially fired reload.

The illustrated embodiment of firing beam 226 has a first lockout notch 222 and a second lockout notch 224 that are substantially contiguous such that the adjacent lower edge 220 of the firing beam is relieved over a longitudinal span corresponding to the first lockout notch 222 and the second lockout notch 224. It is contemplated that in other embodiments, the first lockout notch and the second lockout notch can be spaced from one another by an unrelieved segment of the lower edge of the firing beam. As further described herein, the heights and longitudinal positions of the first lockout notch and the second lockout notch can be configured to achieve desired operational characteristics of a stapler handle assembly.

Figure 34:
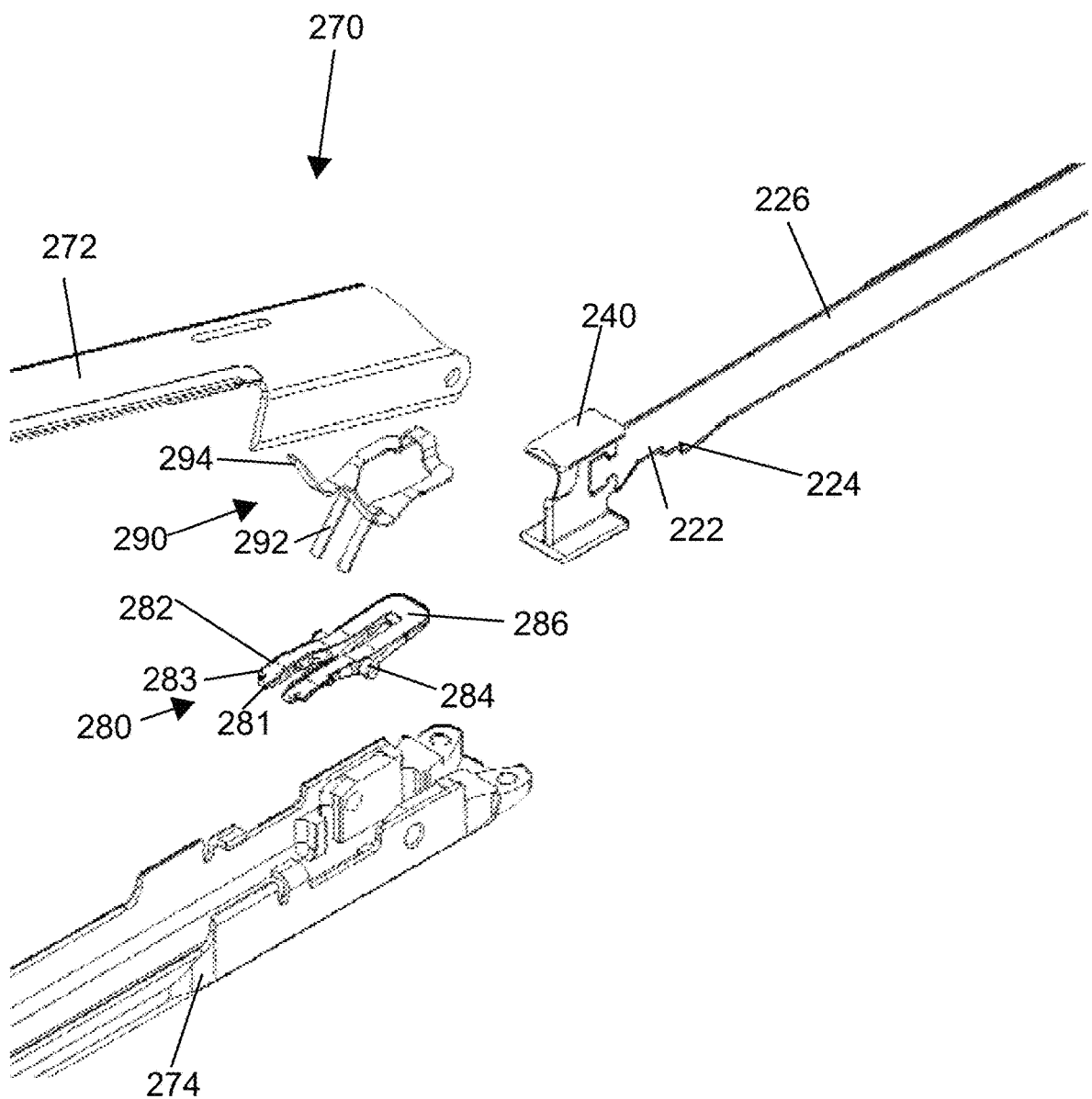
FIG. 34 is a partially exploded perspective view of a proximal end of a jaw assembly of certain embodiments of elongate shaft assembly of a surgical stapling device.
Figure 35:
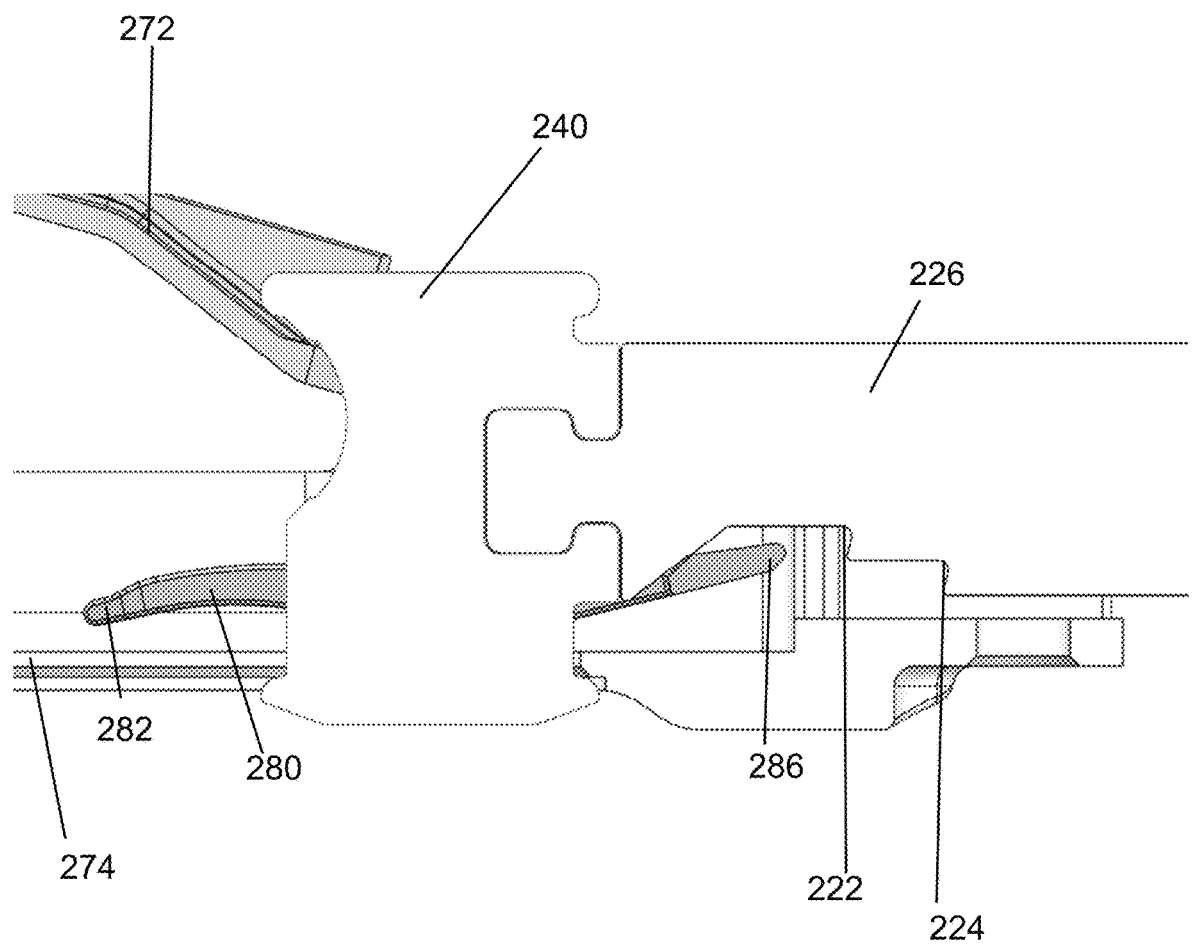
FIG. 35 is a cut away side view of a proximal end of a jaw assembly of certain embodiments of elongate shaft assembly of a surgical stapling device.

With reference to FIGS. 34 and 35, a portion of the jaw assembly 270 is illustrated in partially exploded (FIG. 34) and cut away side views (FIG. 35), with various components hidden for illustration of the empty jaw assembly lockout mechanism and the fired reload lockout mechanism. In certain embodiments, the lockout mechanisms comprise a two-position lockout lever 280, a biasing spring 290, a first lockout notch 222, and a second lockout notch 224. The three position lockout lever 280 has a distal end 282 configured to engage a first lockout actuator and a second lockout actuator on a reload cartridge, a pivot 284 proximal the distal end, and a proximal end 286 configured to engage either the first lockout notch, the second lockout notch, or neither. The biasing spring 290 has at least one lower spring arm 292 biasing the end of the lockout lever 280 distal the pivot 284 in a downward direction towards the reload support of the second jaw 274. In the illustrated embodiment, the biasing spring has two lower spring arms 292 with a gap therebetween allowing passage of the firing member 240 and the firing beam 226. The biasing spring 290 can have at least one upper spring arm 294 that biases the first jaw 272 towards an open configuration. The biasing spring 290 can be configured to sit astride the firing beam 226 and can have a central saddle member from which the at least one lower spring arm 292 and the at least one upper spring arm 294 extend.

Figure 38:
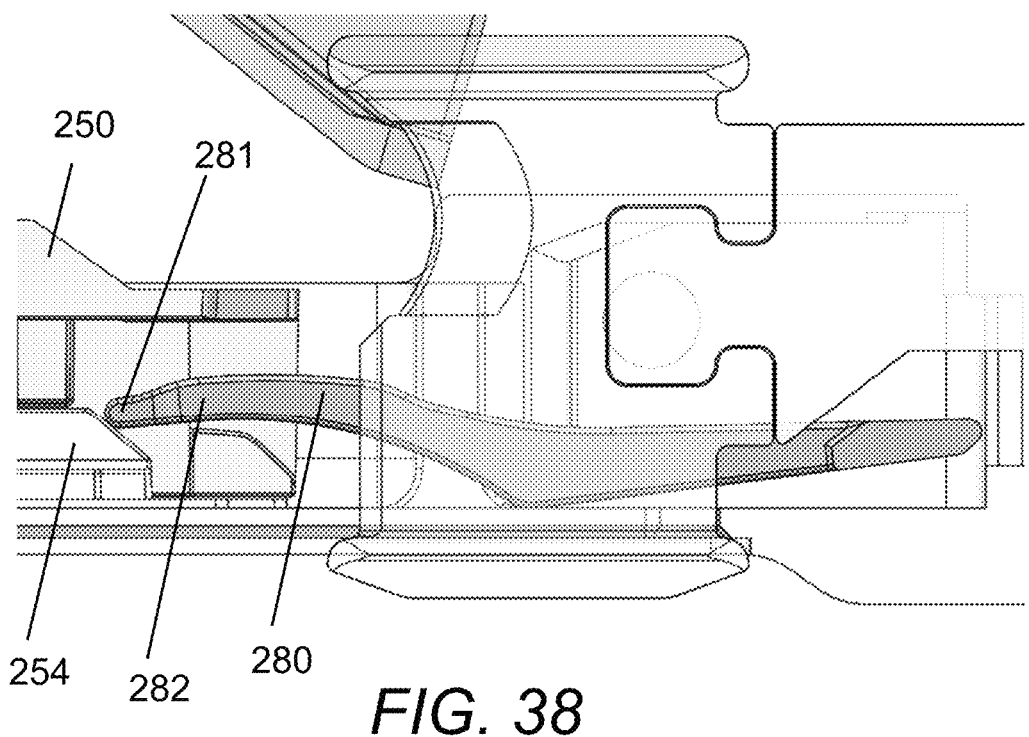
FIG. 38 is a cut away side view of the proximal end of the jaw assembly of FIG. 35 with an unfired reload partially inserted.
Figure 39:
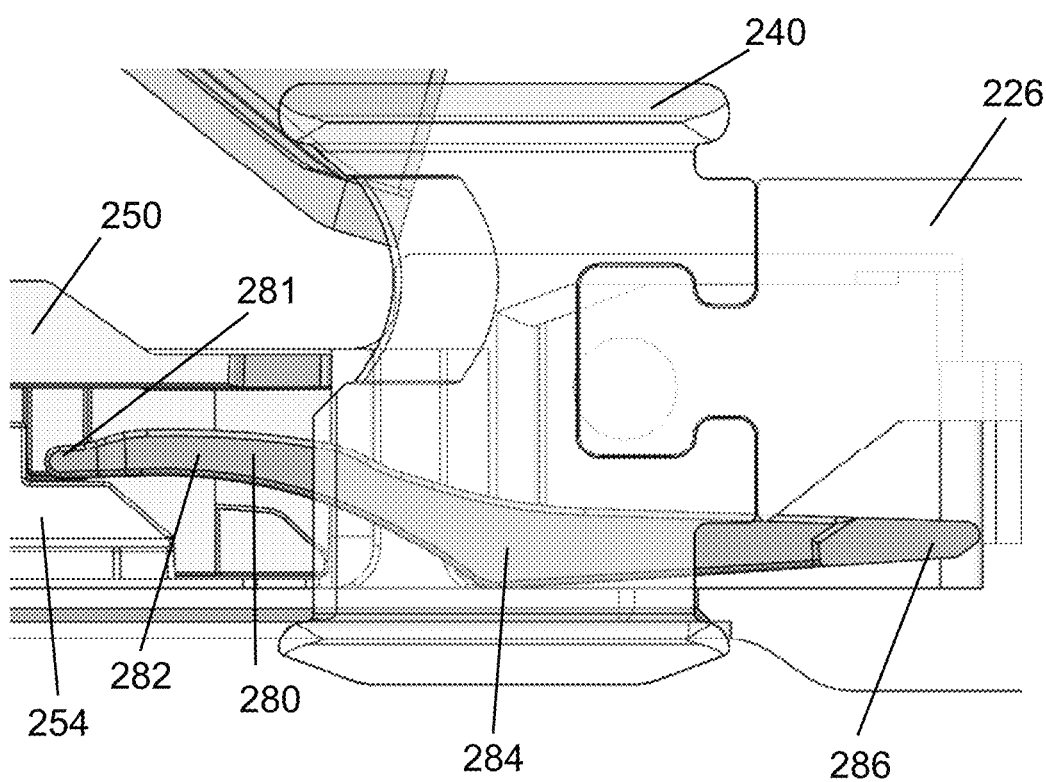
FIG. 39 is a cut away side view of the proximal end of the jaw assembly of FIG. 35 with an unfired reload inserted.
Figure 40:
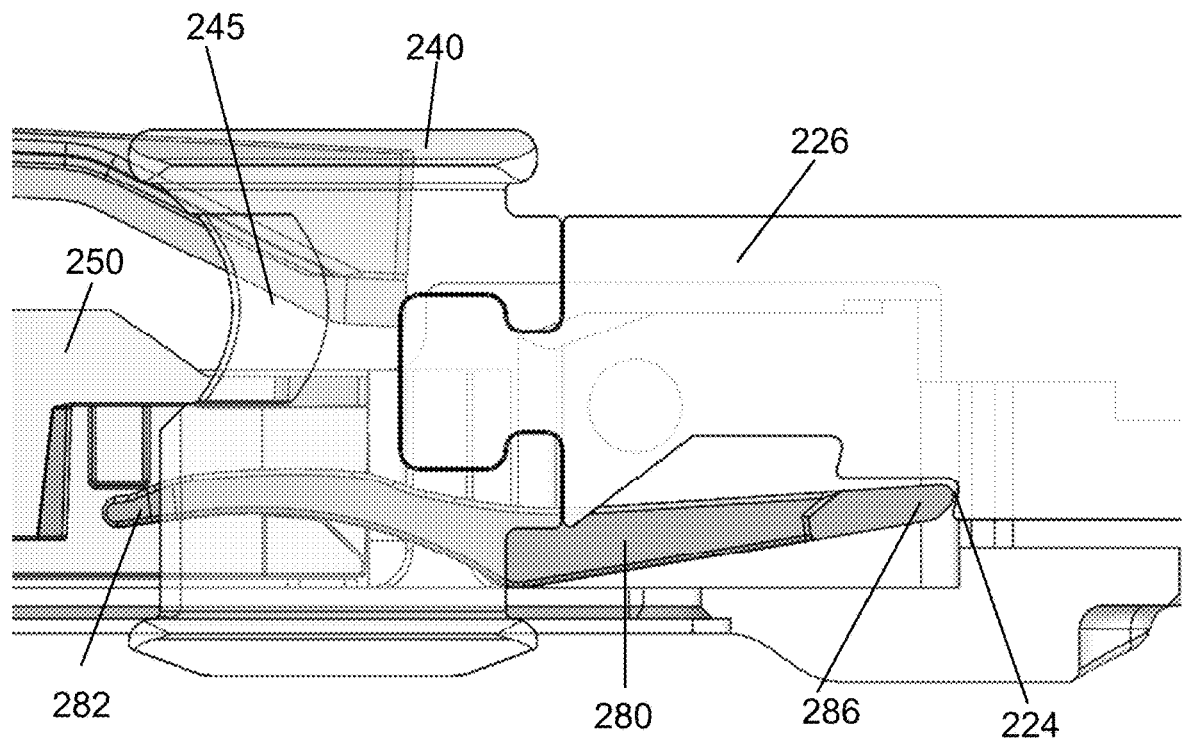
FIG. 40 is a cut away side view of the proximal end of the jaw assembly of FIG. 35 with an at least partially fired reload inserted.
Figure 41:
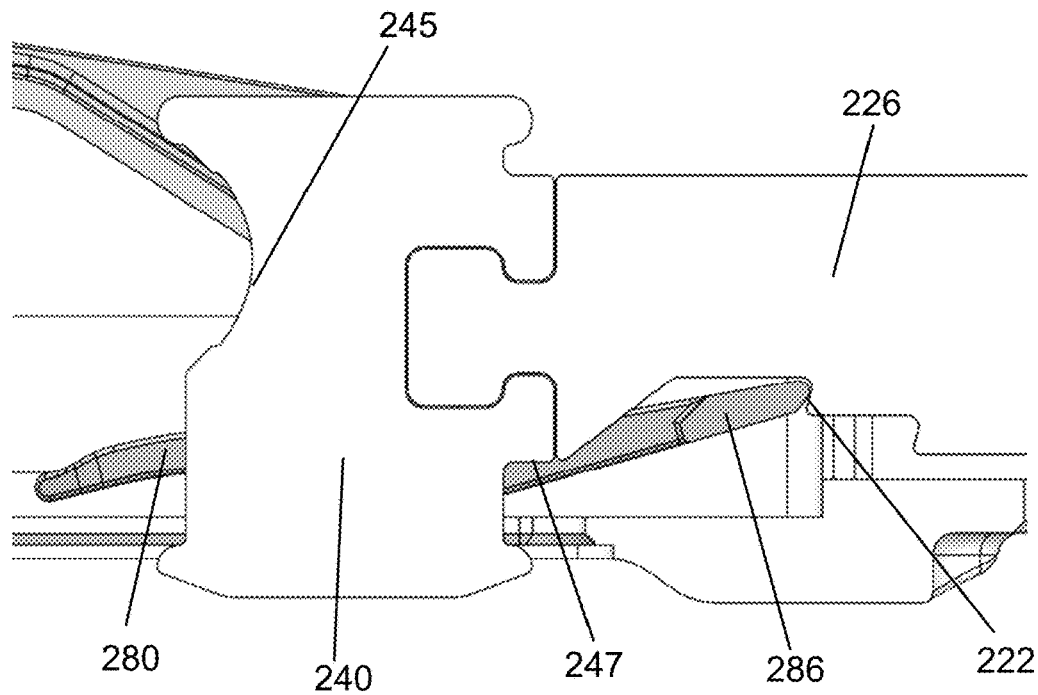
FIG. 41 is a cut away side view of the proximal end of the jaw assembly of FIG. 35 with no reload inserted.

With reference to FIGS. 36-41, operation of the two lockout mechanisms is illustrated. In these partial cut away side views of a proximal end of certain embodiments of jaw assembly, certain elements of the jaw assembly (such as biasing spring) are not illustrated, and certain components (such as firing member 240) are illustrated as transparent elements to enhance visibility of the operation of the lockout mechanisms. FIGS. 36-39 illustrate functioning of the lockout mechanisms as a full, unfired staple reload 250 cartridge is positioned in the reload support of the second jaw 274. FIG. 40 illustrates operation of the fired reload lockout mechanism. FIG. 41 illustrates operation of the empty jaw assembly lockout mechanism.

Figure 36:
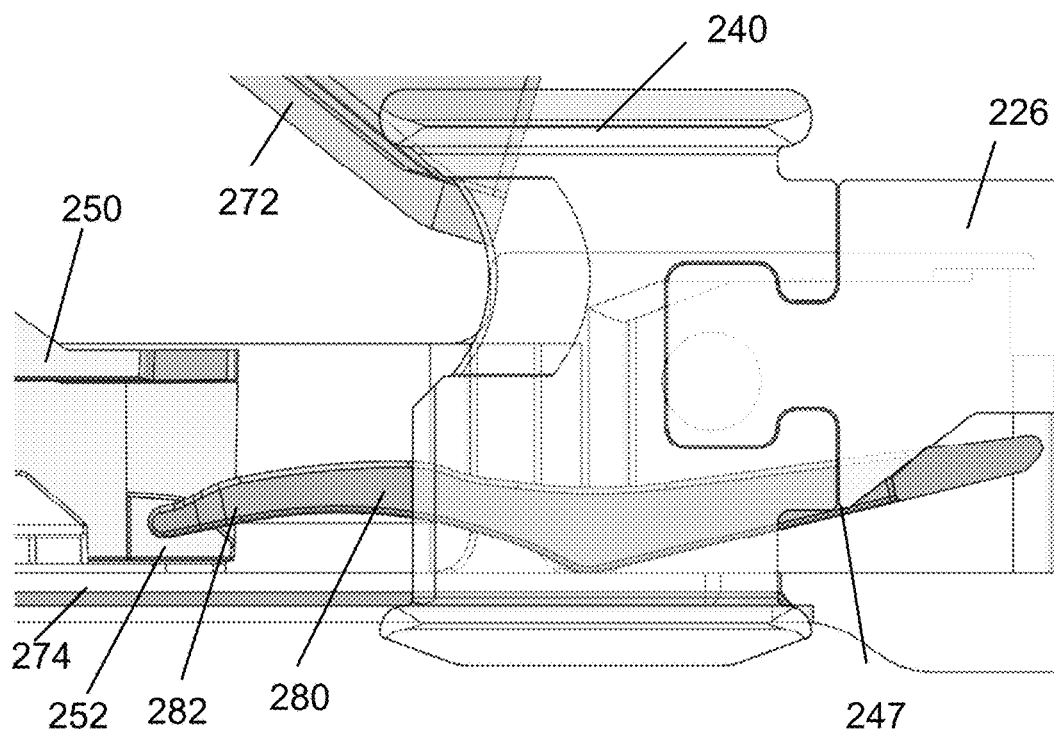
FIG. 36 is a cut away side view of the proximal end of the jaw assembly of FIG. 35 with an unfired reload partially inserted.

With reference to FIG. 36, a cut away view of the proximal end of the jaw assembly is illustrated. The jaw assembly is in an open configuration such that the first jaw 272 is biased to an open position relative to the second jaw 274. The firing member 240 and firing beam 226 are in a fully proximally retracted position such that a proximal surface of the lockout lever 280 rests on a proximally extending tail 247 of the firing member 240. Thus, the distal end 282 of the lockout lever 280 is raised slightly away from the reload support such that a lockout actuator can be positioned between the reload support and the lockout lever 280.

With continued reference to FIG. 36, the slight raise of the distal end 282 of the lockout lever 280 can accept a ramped proximal surface of the first lockout actuator or ramped boss 252 formed on the reload cartridge body. The distal end 282 of the lockout lever 280 has a lateral extension 283 (FIG. 34) positioned to engage the first lockout actuator and a medial surface 281 (FIG. 34) positioned to engage the second lockout actuator as the reload cartridge 250 is slid proximally upon insertion to the reload support of the jaw assembly.

Figure 37:
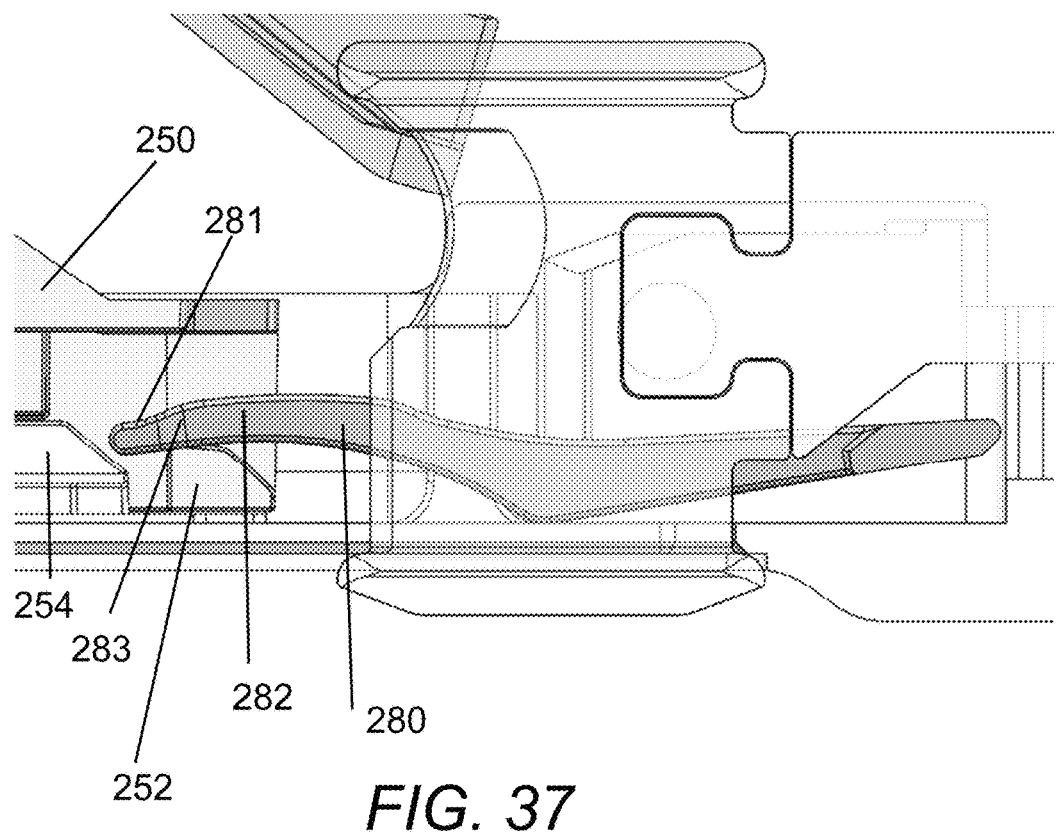
FIG. 37 is a cut away side view of the proximal end of the jaw assembly of FIG. 35 with an unfired reload partially inserted.

With reference to FIG. 37, a cut away view of the proximal end of the jaw assembly is illustrated with the reload 250 cartridge partially inserted. As illustrated, the lateral extension 283 of the distal end 282 of the lockout lever 280 has engaged a ramped proximal surface 283 of the ramped boss 252. As the reload 250 cartridge is further slid proximally, the lateral extension 283 travels up the ramped surface to a first height relative to the reload support, pivoting the lockout lever 280 into the second position and defeating the empty jaw assembly lockout mechanism. Operation of the empty jaw assembly lockout mechanism is further described below with reference to FIG. 41. In the illustrated embodiment, the second lockout actuator or slider tail 254 of an unfired reload 250 cartridge is positioned just distal of the first lockout actuator at a height positioned to engage with the medial surface 281 of the distal end 282 of the lockout lever 280 once the distal end 282 of the lockout lever 280 has been raised to the first height from the reload support by the first lockout actuator. Accordingly, when viewed in a cut away side view, as illustrated in FIG. 37, the first lockout actuator and second lockout actuator define a progressive ramped profile arranged to elevate the distal end 282 of the lockout lever 280 to two predefined positions as a reload 250 cartridge is inserted into the reload support.

With reference to FIG. 38, a cut away view of the proximal end of the jaw assembly is illustrated with the reload 250 cartridge almost fully inserted. As illustrated, the medial surface 281 on the distal end 282 of the lockout lever 280 has engaged a ramped proximal surface of the second lockout actuator or slider tail 254. In the illustrated embodiment, the proximally extending tail 254 of the slider of the reload 250 has a lead-in ramped surface that, with the reload cartridge in an unfired state, engages the distal end 282 of the lockout lever 280. In certain embodiments, the lockout lever 280 and slider tail 254 can be configured to provide a smooth, relatively low friction reload insertion and reduce the possibility of binding or inadvertent advancement of the slider during insertion of the cartridge. For example, in certain embodiments, the medial surface 281 of the distal end 282 of the lockout lever 280 can have a radiused distal tip such that the lockout lever 280 will be pivoted by interaction with the slider tail despite potential slight angular misalignments between the reload 250 cartridge and the reload support. Moreover, in certain embodiments, the ramped proximal surface of the slider tail 254 can extend from a first height relative to the reload support at a proximal end that is smaller than a height of the first lockout actuator relative to the reload support. Accordingly, as an unfired reload 250 cartridge is positioned in the reload support, the distal end 282 of the lockout lever 280 can transition from the first lockout actuator to the second lockout actuator smoothly at a wide range of angular alignments between the reload cartridge and reload support.

With reference to FIG. 39, a cut away view of the proximal end of the jaw assembly is illustrated with the reload 250 cartridge fully inserted. As illustrated, the medial surface 281 on the distal end 282 of the lockout lever 280 has been advanced along the ramped proximal surface of the second lockout actuator and onto the second lockout actuator or slider tail 254. This advancement along the ramped surface of the slider tail 254 pivots the lockout lever 280 about the pivot 284 such that the distal end 282 of the lockout lever 280 is at a second height with respect to the reload support. With the distal end of the lockout lever 280 at the second height, the lockout lever is in an unlocked position, corresponding to an unlocked state of the empty jaw assembly lockout mechanism and an unlocked state of the fired reload lockout mechanism.

With continued reference to FIG. 39, with the lockout lever 280 in the unlocked position, the proximal end 286 of the lockout lever 280 is positioned at a height below a lower edge of the firing beam. Accordingly, the firing member 240 and firing beam 226 can be distally advanced through an open-close stroke and a firing stroke responsive to user input from an operatively coupled mechanical or powered handle assembly (FIGS. 1-5). Accordingly, when an unfired reload cartridge is inserted to the reload support of the jaw assembly, both the empty jaw assembly lockout mechanism and the fired reload lockout mechanism are defeated to allow a user to operate a stapler handle assembly to grasp tissue with the jaw assembly and fire staples from the jaw assembly by distal translation of the firing beam and firing member within the jaw assembly.

With reference to FIG. 40, once a reload 250 cartridge has been at least partially fired, the slider within the reload 250 is advanced distally from a proximal, unfired position. Upon completion of a firing stroke, the slider remains at a distal location within the reload cartridge while the firing beam 226 and firing member 240 can be retracted proximally responsive to operation of a handle assembly in a return or retraction stroke. Thus, once a reload 250 cartridge has been partially or fully fired the second lockout actuator or slider tail is not in position to engage the distal end 282 of the lockout lever 280. In certain embodiments, the first lockout actuator or ramped boss 252, however, is stationary relative to a body of the cartridge. Thus, with a partially or fully fired reload 250 positioned in the reload support, the distal end 282 of the lockout lever 280 is engaged by the first lockout actuator to position the distal end 282 of the lockout lever 280 at the first height relative to the reload support. With the distal end 282 of the lockout lever 280 at the first height, corresponding to the second position of the lockout lever, the empty jaw assembly lockout mechanism is defeated, but the fired reload lockout mechanism is locked.

With continued reference to FIG. 40, with the lockout lever 280 in the second position, the proximal end 286 of the lockout lever 280 is at a height corresponding to the second lockout notch 224 on the firing beam 226. Moreover, in certain embodiments, the biasing spring 290 (FIG. 34) exerts a force on an upper surface of the distal end 282 of the lockout lever 280, tending to maintain the proximal end 286 of the lockout lever 280 at the height corresponding to the second lockout notch 224 on the firing beam 226. Accordingly, if a user attempts to actuate the jaw assembly with a fired reload cartridge present in the jaw assembly, the firing beam 226 can be distally advanced until the proximal end 286 of the lockout lever 280 seats within the second lockout notch 224 of the firing beam 226, indicating engagement of the fired reload lockout mechanism and preventing further distal motion of the firing beam and the firing member.

With continued reference to FIG. 40, in certain embodiments the fired reload lockout mechanism can be configured to permit operation of the jaw assembly of the stapling device in at least a portion of an open-close stroke. For example, in certain embodiments, the position of the second lockout notch 224 and the length of the lockout lever 280 can be sized and configured such that the firing beam 226 is arrested upon engagement of the fired reload mechanism at a position corresponding to a fully closed or almost fully closed configuration of the jaw assembly. With the jaw assembly in such a configuration, the firing member 240 has advanced to a distal position that approximates the first jaw and the second jaw, but maintains the cutting edge 245 in a substantially recessed location. Advantageously, with the fired reload lockout configured to permit an open-close stroke, after firing staples from a reload cartridge, a user can operate the jaw assembly in one or more open-close strokes to assess tissue thicknesses and consistency at various locations for application of a potential second reload. Likewise, as insertion of a stapling device through a surgical access port such as a trocar can typically require the jaw assembly to be in a closed configuration, a user could withdraw and reinsert the jaw assembly through one or more surgical access ports to evaluate tissue thicknesses and consistency at various locations in a surgical site.

With continued reference to FIG. 40, in certain embodiments, the fired reload lockout mechanism can be further configured to prevent operation of the stapling device in a firing stroke. Mechanical and powered stapler handle assemblies configured for use with an elongate shaft and jaw assembly as described herein, such as those discussed above with respect to FIGS. 1-5, typically include firing mode selector mechanisms or firing safety switches to allow a user to affirmatively select operation of a firing stroke of the jaw assembly only once the jaw assembly has been positioned in a closed configuration. Thus, in certain embodiments, the position of the second lockout notch 224 and the length of the lockout lever 280 can be sized and configured such that the firing beam is arrested upon engagement of the fired reload lockout mechanism at a position corresponding to a position proximal to a fully closed configuration of the jaw assembly. Thus, in these embodiments, once the fired reload lockout mechanism has been engaged, a user would be unable to select operation of the firing stroke on the handle assembly. Advantageously, operation of the fired reload lockout mechanism to prevent selection of the firing stroke on the handle assembly would serve as an indication to the user that a lockout had been engaged.

With reference to FIG. 41, a cut away view of the proximal end of the jaw assembly is illustrated with no reload cartridge inserted and the firing member and firing beam slightly longitudinally advanced. With no reload present, once the tail 247 of the firing member 240 advances off of the proximal end 286 of the lockout lever 280, the biasing spring 290 (FIG. 34) exerts force on the upper surface of the distal end 282 of the lockout lever 280 towards the reload support. Thus, upon initial advancement of the firing beam 226 responsive to a user actuating a handle assembly to advance the jaw assembly in an open-close stroke, the lockout lever 280 is pivoted into a first position corresponding to a locked configuration of the empty jaw assembly lockout mechanism. As the firing beam 226 is advanced distally, the proximal end 286 of the lockout lever 280 seats in the first lockout notch 222 on the firing beam 226 and engages the empty jaw assembly lockout mechanism, preventing further distal translation of the firing beam 226 and firing member 240.

With continued reference to FIG. 41, in certain embodiments the empty jaw assembly lockout mechanism can be configured to arrest motion of the firing beam at a position corresponding to a substantially open configuration of the jaw assembly. For example, the position of the first lockout notch 222 on the firing beam 226, the length of the lockout lever 280, and the length of the tail 247 of the firing member 240 can be sized and configured such that the empty reload lockout mechanism is locked early in an open-close stroke of the jaw assembly. Advantageously, with the empty jaw assembly lockout mechanism configured to lock during an initial portion of the open-close stroke, a user would be unable to actuate a handle assembly to close the jaw assembly sufficiently to be inserted through a surgical access port if no reload cartridge were present in the jaw assembly. Thus, with an empty jaw assembly lockout mechanism so configured, a user would have a tactile indication that no reload cartridge is present in the jaw assembly before inadvertently introducing an empty jaw assembly to a surgical site. Moreover, such an empty jaw assembly lockout desirably maintains the cutting edge 245 of the firing member 240 in a substantially retracted, shielded position relative to the jaw assembly with no reload present in the jaw assembly.

Light Ring User Display

In certain embodiments, the handle assembly can include a control unit that processes and, in some instances stores or saves to a memory module, operating data including information about difficulty of firing, information about the test time, and state of the device. It can thus be desirable that the stapler include a user display to convey certain operational information to a surgeon so that he or she can make an intelligent decision about the firing they are about to perform. For example, in some instances, it can be desirable to provide a user with certain information regarding clamping time and whether the clamped tissue has a thickness that is appropriate to staple over within the operational parameters of the staple reload cartridge in the end effector of the stapler.

Figure 42:
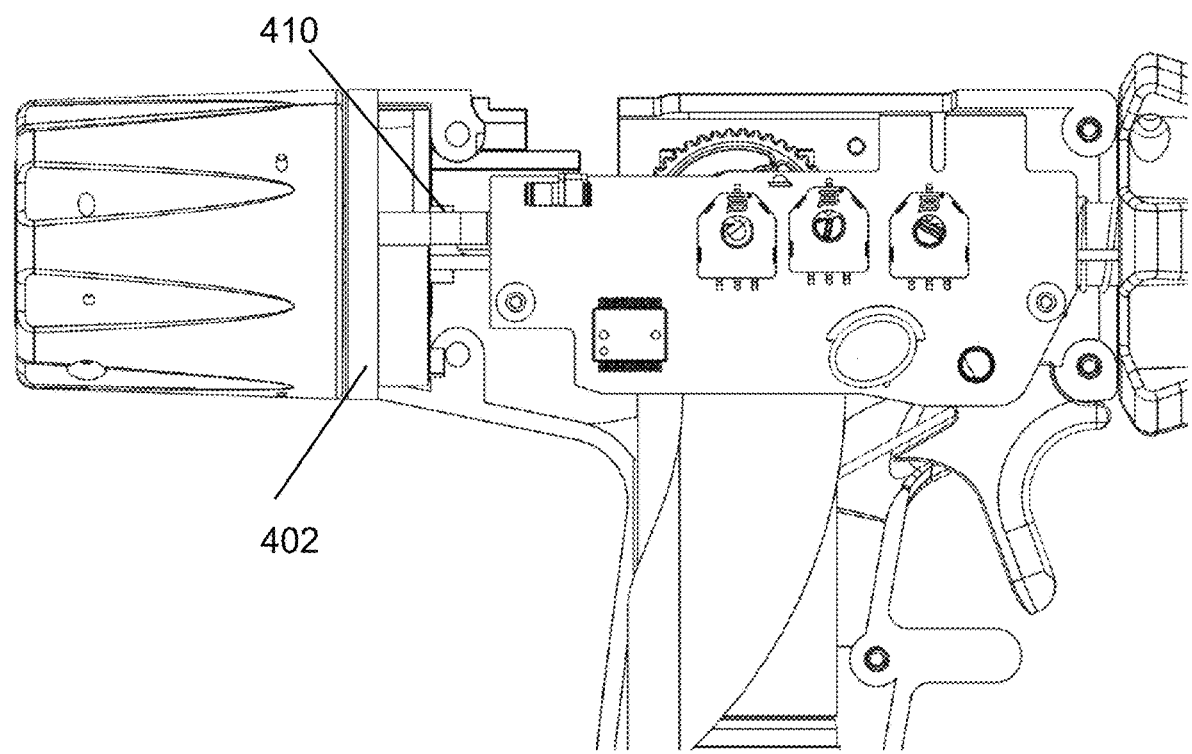
FIG. 42 is a partial cut-away side view of the powered handle of FIG. 2 with an electrically coupled light ring user display.

With reference to FIG. 42, in certain embodiments, the handle assembly can include a multifunction illuminated display such as an annular illuminated "light ring" user display 402 subassembly as a user display. Advantageously, the annular configuration of the light ring subassembly provides high visibility of the user display to the operator from any device orientation as the handle assembly is repositioned and manipulated to various angular orientations during a surgical procedure.

Figure 43:
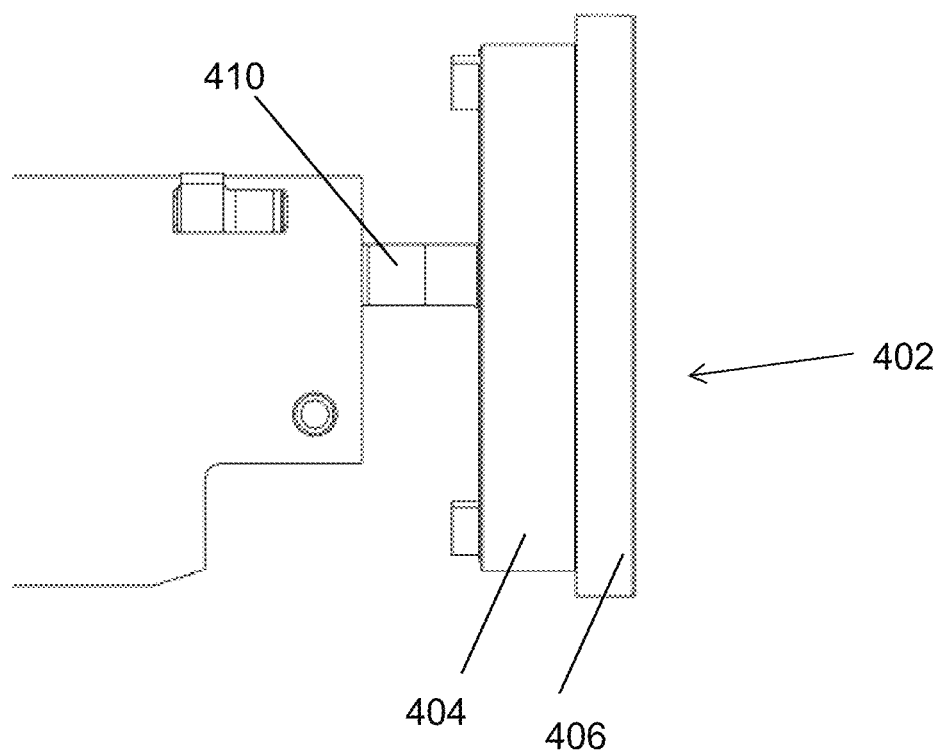
FIG. 43 is a side view of the light ring user display of the powered handle of FIG. 2.
Figure 44:
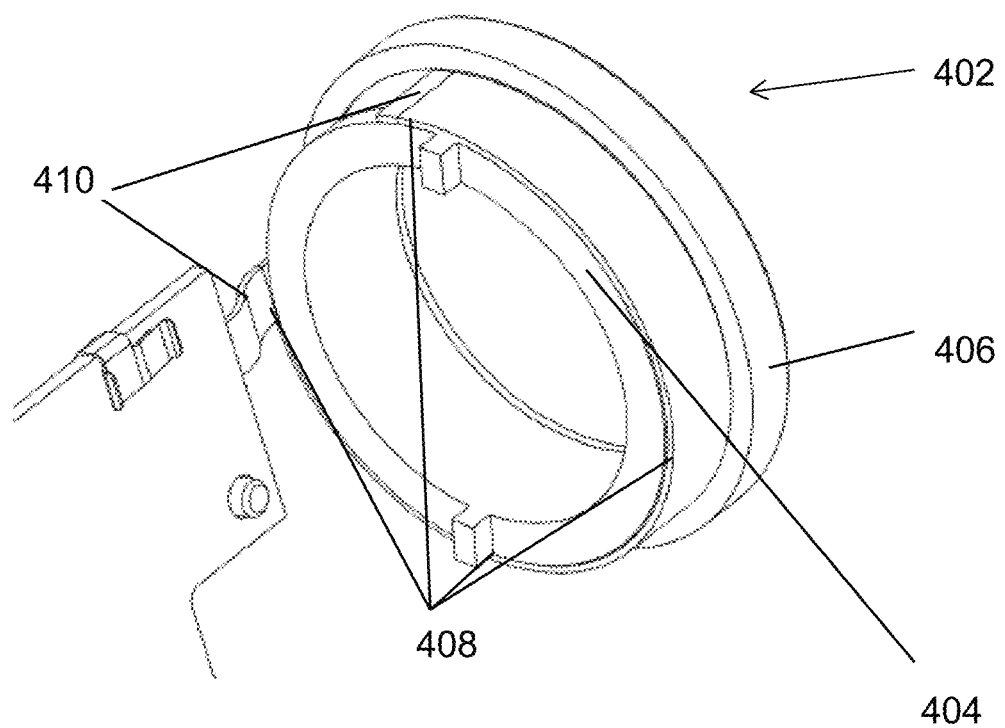
FIG. 44 is a perspective view of the light ring user display of the powered handle of FIG. 2.

With reference to FIGS. 43-44, in the illustrated embodiment, the light ring user display 402 comprises an annular light reflector 404, an annular light ring 406, and a plurality of light sources 408. The annular light reflector 404 is positioned radially inwardly of the annular light ring 406 such that illumination from light sources 408 shining radially inwardly reflect off of the annular light reflector and are transmitted through the annular light ring. The material of the light ring 406 can be selected to allow a high degree of light transmission while controlling light dispersion to avoid external bright spots visible to the user. As illustrated, the user display 402 comprises four light sources 408, approximately equally spaced about the light ring user display 402. In certain embodiments, the light sources can each comprise an RGB light emitting diode that is capable of illuminating in a wide variety of colors and brightnesses. The light ring user display 402 can be electrically coupled to the control unit of the handle assembly, such as a circuit board over a flexible printed circuit board such as a Rigid Flex printed circuit board. As illustrated, the flexible printed circuit board 410 can be formed into an annular configuration and positioned between the annular light ring 406 and the annular light reflector 404. The light sources 408 can be mounted to an inner surface of the flexible electrical cable 410 to emit light radially inwardly towards the annular light reflector 404. Desirably, the shape of the flexible printed circuit board and the housing reflector can easily allow the light sources to be held at any angle to maximize reflected light and minimize bright spots.

Although one embodiment of a light ring user display 402 is illustrated and discussed above, it is contemplated that other embodiments of light ring user display can include other aspects. For example, in certain embodiments, more or fewer than four light sources 408 can be used in the light ring user display and different or additional illuminating technologies can be used. In some embodiments, the light sources can be positioned on an outer surface of the flexible electrical cable 410 to emit directly through the annular light ring 406 with no annular light reflector in the light ring user display. In other embodiments, a surface formed on one or both halves of a housing of the handle assembly can be used to emit light from the light sources without the use of a separate annular light ring.

With reference to FIG. 42, it is contemplated that the light ring user display 402 can be electrically coupled to the control unit and configured to display a variety of status messages to a user. For example the color, brightness, flashing sequence, or steady on/off illumination can be controlled to convey desired information to a user. Additionally, in some embodiments, the occurrence of and/or speed of a particular color transition, or brightness transition can be used to convey information to a user. In some display control profiles, a first color can be used to indicate the handle is in an open-to-clamp functionality with no possibility of a firing actuation while a second color can be used to indicate the stapler is in a firing mode configured to fire staples. Additional colors or other indicia can be used to represent other events or operational states of the stapler such as: a firing has been completed and the firing mechanism is being reversed; and that a firing error has occurred.

Control Unit

As previously discussed with respect to certain features of the illustrated handle assembly, the handle assembly can further comprise a control unit. As illustrated, the control unit can comprise a microcontroller electrically coupled to a circuit board to which various additional sensor, power supply, and user display components are electrically coupled. The control unit can be configured to drive the motor to provide open-to-clamp functionality followed by staple firing functionality at a stapler jaw assembly. The control unit can additionally be configured to modify the operational parameters of the motor based on sensory data from one or more of: a motor load sensor, an actuation rack position sensor, a shaft recognition sensor, and an articulation position sensor.

Figure 45:
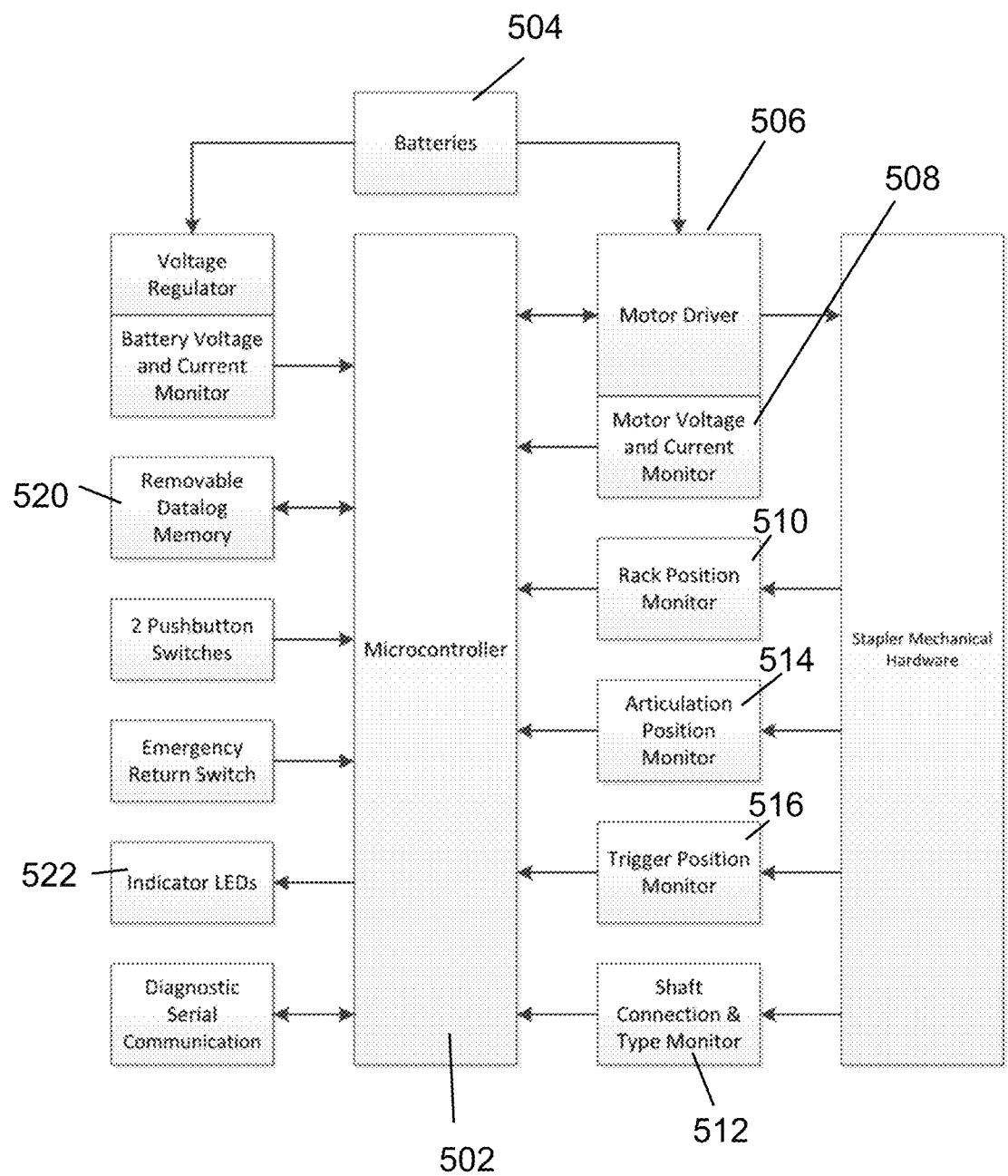
FIG. 45 is a block diagram of information and power flow for an embodiment of control system for the powered handle of FIG. 2.

With respect to FIG. 45, a schematic flow diagram indicating data and power flow for an exemplary control system for a powered handle is illustrated. In the illustrated flow diagram, the control system comprises the illustrated microcontroller 502. In various embodiments, the microcontroller can comprise an application specific integrated circuit or a general purpose microcontroller running application specific firmware and/or software. As illustrated, the microcontroller receives power and data regarding battery status from the batteries 504 in the power supply. The microcontroller further receives data from various mechanical hardware of the stapler such as a motor driver 506 and current monitor 508, an actuation rack position sensing mechanism 510, and a shaft connection and type monitor 512. As discussed above with respect to the articulation mechanism, the microcontroller 502 can additionally receive articulation position information from an articulation position sensing mechanism 514. The microcontroller can further receive data from a user via a trigger position sensor 516, and pushbutton switches. The control system can output a control signal to actuate the drive system of the powered handle through a motor driver 506. The control system can also output certain operational parameter information to a memory module 520, which, in certain embodiments, can comprise a removable module, and can output certain data for user viewing through LED lights 522 on the handle, such as the light ring user display discussed herein. In some embodiments, the control system can be configured to provide haptic feedback to a user such as by actuation of a separate haptic module or by actuation of a haptic generation motor drive profile that can direct rotation of the motor one or more small displacements in forward and reverse directions, as described further herein with reference to FIGS. 56-57, such that a user would feel a feedback sensation but the position of the actuation rack would not be significantly affected. In some embodiments, the microcontroller can be configured to transmit and receive information wirelessly, such as, for example over a Bluetooth, WiFi, or another wireless protocol.

In certain embodiments, the control system is also configured to further define operational parameters of the powered handle. For example, by querying a memory module on the power supply or on the control system itself, the control system can detect whether the powered handle has been used for more than a single procedure. In some embodiments, the stapling system is designed for use in a single procedure and is not designed for resterilization. Additionally, the control system can also query the memory modules on the power supply or the control system to detect a number of staple firings to assess whether sufficient battery power remains to complete an additional firing.

In certain embodiments, the control system is configured to detect tissue characteristics that can prevent staple firing. In some embodiments, the control system can monitor position, velocity, and supplied torque of the motor in the drive system. The control system can detect whether excessive torque is required to close the jaw assembly, if excess time is needed to close the jaw assembly, or if the jaws are closing at a low speed. These conditions may indicate that the tissue in the jaw assembly is too thick or too dense for the stapler to be effective. In certain embodiments, the control system can monitor the position of the actuation shaft with respect to time and evaluate this monitored position and time with respect to a baseline 'zero load' time reference position and time to assess the tissue characteristics such as thickness and density. In instances where the drive system exceeds predetermined operational parameters, the control system can indicate an error condition and stop a firing operation.

Figure 46:
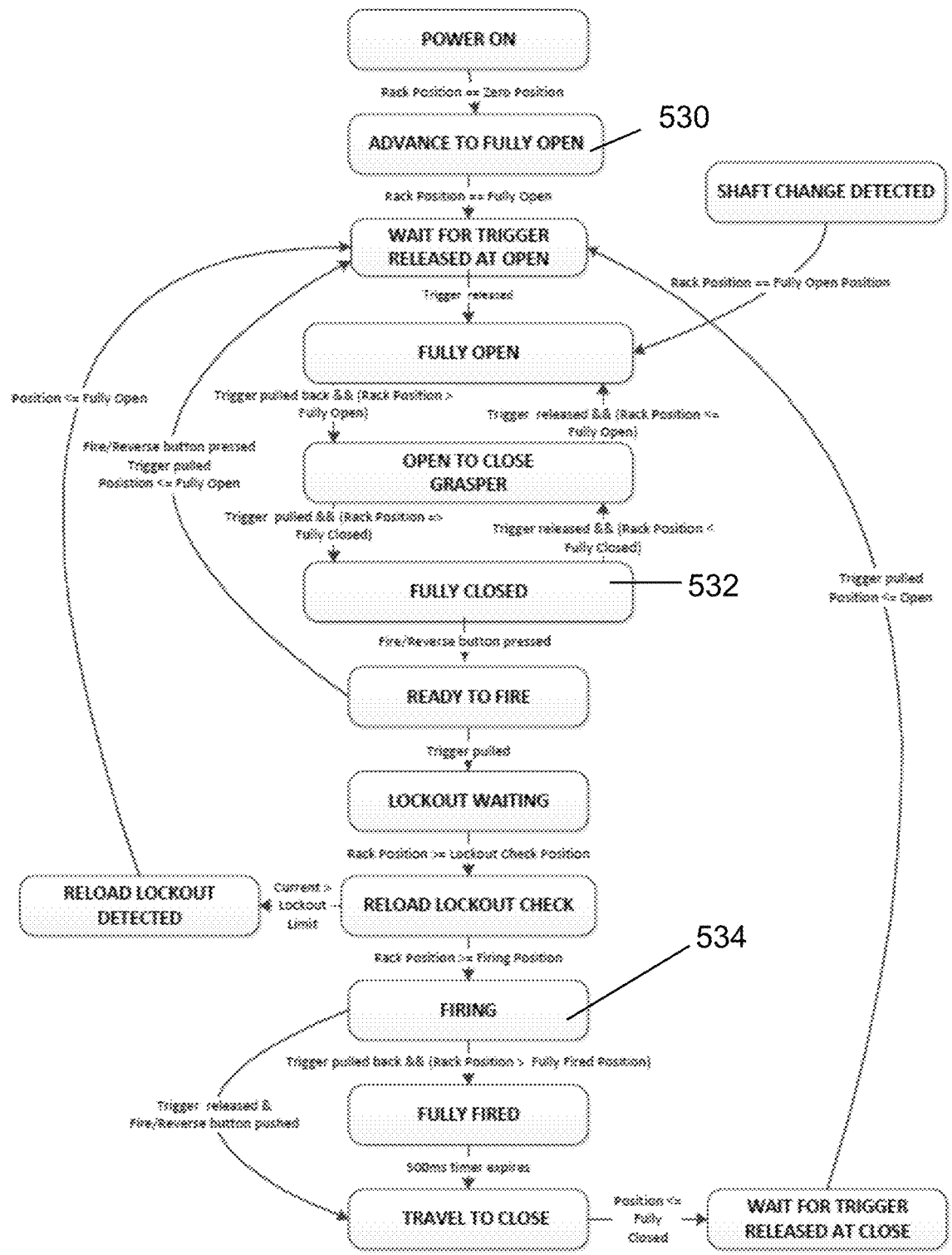
FIG. 46 is an operational sequence flow chart for an exemplary operational sequence of the powered handle of FIG. 2.

With reference to FIG. 46, a block diagram of an operational flow chart for an exemplary firing sequence of the control system is illustrated. As illustrated, the control system integrates user inputs from the trigger and firing button as well as hardware inputs from various sensors and monitors to advance the jaw assembly from a fully open condition 530 to a fully closed condition 532 to a firing sequence 534, then back to the fully open condition 530.

During a firing operation, the control unit can monitor a position of the actuation shaft to provide and provide a desired motor drive profile. In certain embodiments, the microcontroller can operate using a motor drive logic profile that identifies various operational zones of the actuation rack position and can apply predetermined motor drive parameters, such as, for example motor speed, and motor load monitoring, for each of these zones and for various actuation rack positions within these zones. In certain embodiments, the motor drive logic profile can be a software or firmware based computing program stored in a memory module such as computer readable media in or electrically coupled to the control unit. In certain embodiments, the motor drive logic profile can define operational parameters for and an operational sequence through one or more of: a grasper zone, a lockout zone, a firing zone, a full fired zone, a returning zone, and an opening zone. In certain embodiments, the motor drive logic profile can be configured to adjust zones and certain positions associated therewith responsive to sensor input received from one or more of the articulation position sensor, the shaft recognition sensor, the motor load monitor, or other sensor input.

The grasper zone corresponds to a zone of movement of the actuation rack between a jaws open position and a jaws clamped position of an attached end effector on an instrument shaft. In this region, the microcontroller can be configured to drive the jaw assembly proportionally to the degree of trigger movement input by the user and transmitted to the microcontroller by a trigger position sensor such as a trigger potentiometer. If the trigger is fully depressed, the device will advance the actuation shaft to position the jaws of the end effector in a fully closed position. If the trigger is fully released, the device will return to jaws open. Fully pulling the trigger while simultaneously pressing the firing button will advance the actuation shaft to the lockout zone. In other embodiments, in the grasper zone, the microcontroller can be configured to drive the motor at a rate proportional to the angle of trigger displacement, such that rather than the amount of jaw closure being defined by trigger movement, the speed of jaw closure in the grasper zone would be defined by trigger movement.

In certain embodiments, the motor speed can be varied through pulse width modulation to a desired travel speed for a particular zone. In certain embodiments, the motor can be pulse width modulated at a duty cycle less than 100% for the grasper zone. In certain embodiments, it can be desirable to drive the motor at a duty cycle between approximately 50% and 90% in the grasper zone. In certain embodiments, the motor drive logic profile can be configured such that the motor is pulse width modulated at a 70% duty cycle in the grasper zone.

From a jaws closed position in the grasper zone, if a user depresses a firing button on the handle, the control unit will advance to the lockout zone of the motor drive logic profile. The lockout zone can be configured to provide a motor control profile for an instrument shaft and jaw assembly that includes a firing lockout to prevent a firing actuation of the stapler if either a fired stapler reload cartridge is present or no stapler reload cartridge is present. Operation of this type of lockout can result in significantly increased loading of the motor as a portion of the firing mechanism in the instrument shaft or jaw assembly is prevented from advancing further at a predetermined actuation position of the actuator. Accordingly, during the lockout zone, the control unit can monitor sensor information from the actuator rack position sensor and a motor load sensor for an expected spike in motor load.

While the embodiments of handle assembly and control unit illustrated herein include a trigger and firing button, it is contemplated that in other embodiments, the handle assembly and control unit can be configured to operate with a single control, such as a single trigger with no firing button or a single button with no trigger. In these single-control embodiments, the control unit can be configured to operate in the grasping zone upon an initial trigger squeeze or button push, then to advance to the lockout zone upon release and a second trigger squeeze or button push. Moreover, in still other embodiments, the handle assembly and control unit can be configured to operate with a dual-input trigger, such as, for example a firing button configured with the control unit to advance the motor and actuator through a firing sequence in a distal or forward direction and a reversing button configured to operate the motor and actuator in a proximal or reverse direction.

From an initial stopped position at the initiation of the lockout zone, the control unit will apply a motor drive profile that ramps up the pulse width modulated duty cycle to achieve a lockout zone motor speed. In certain embodiments, the lockout zone duty cycle is less than the grasper zone duty cycle. For example, in some embodiments, it can be desirable that the lockout zone duty cycle is between approximately 30% and approximately 60%. In other embodiments, the lockout zone duty cycle is between approximately 45% and 55%. In certain embodiments, the lockout zone duty cycle can be approximately 50% throughout the lockout zone. Within the lockout zone, the control unit will monitor actuation rack position and assess motor load with reference to certain predefined positions. From the jaws closed position, initially, the control unit does not actively monitor motor load for a load spike. There can be a relatively high load as the actuator duty cycle is ramped up to the lockout zone duty cycle that settles to a relatively lower, operational load. When the actuation rack position reaches a predetermined lockout low position, the control unit will monitor for a potential motor load spike. The control unit will continue to monitor the motor load until the actuation rack is translated to a position defined as a lockout high position.

The lockout low and lockout high position define a predetermined buffer around a lockout nominal position. The lockout nominal position corresponds to an expected position of a motor load spike due to operation of a lockout mechanism. However, various factors related to tissue thickness and jaw articulation may shift the position of an actual motor load spike from the expected lockout nominal position, so the lockout zone is configured to detect the motor load spike in a range extending in a buffer zone on either side of the lockout nominal position.

In certain embodiments, control unit monitors the motor load by tracking the electrical current drawn by the motor. In certain embodiments, a lockout current spike is defined as any value that exceeds a predetermined current threshold. As discussed further below, in other embodiments of control system, the control unit can include a lockout module to detect engagement of other embodiments of lockout mechanism that engage in the grasper zone. In certain embodiments, the threshold can be defined as a current value sampled at a predetermined position, such as the lockout low position, plus an additional amount that can indicate a spike in load. In certain embodiments, the threshold can be the lockout low current value plus an additional at least 20 mA. In other embodiments, the threshold can be defined to be the lockout low current value plus an additional at least 50 mA. In still other embodiments, the threshold can be defined as a current value sampled at the lockout low position plus 30 mA. In other embodiments, other motor parameters could be monitored and other threshold values can be used to define a load spike. If the control unit detects a motor load spike between the lockout low position and the lockout high position, typically this condition indicates that a firing lockout has been triggered due to a missing or used reload. If the control unit detects a firing lockout, the motor drive profile is configured to immediately return the actuation shaft to return the jaw assembly to jaws open. If the control unit does not detect a motor load spike corresponding to a firing lockout in the lockout zone, then the control unit will advance to the firing zone.

The firing zone occurs between the lockout high at an end of the lockout zone and a full fire start at the beginning of the full fired zone. The control unit has a motor drive profile ramping up the motor drive duty cycle from the lockout zone duty cycle to a relatively high duty cycle and travels at this speed for the duration of this zone. For example, in some embodiments, the firing zone duty cycle can be between 70% and 100%. In certain embodiments, the firing zone duty cycle can be approximately 100% for the duration of the cycle.

The full fired zone begins when translation of the actuation rack reaches a predefined full fire start position. Once the actuation rack has been translated to the full fire start position, the control unit applies a motor drive profile ramping motor duty cycle down to a full fire zone duty cycle. In some embodiments, the full fire zone duty cycle can be between approximately 30% and 80%, and desirably between approximately 40% and 60%. In certain embodiments, the full fire zone duty cycle can be approximately 50%. The control unit also monitors motor load to begin detecting a current spike. A current spike in the full fired zone indicates a firing mechanism in the jaw assembly and reload has reached the distal end of its travel. In some embodiments, an I-beam jaw closure and firing beam has been fully extended and has hit the distal end of the jaw assembly. In some embodiments, the motor load can be monitored during the full fired zone to detect a current spike defined as any value that exceeds a current sampled at the full fire start position.

The control unit can incorporate sensor data from the shaft recognition sensor described above to assign different values for the full fire start position initiating the full fired zone based on a length of the jaw assembly coupled to the handle assembly. For example, the full fire start position would be relatively low for a jaw assembly having 30 mm jaws as compared with a jaw assembly having 45 mm jaws. Likewise, the full fire start position would be relatively low for a jaw assembly having 45 mm jaws as compared with a jaw assembly having 60 mm jaws. In certain embodiments, the shaft recognition sensor and control unit can be configured to recognize several shaft lengths and define full fire zone positions corresponding to these recognized shaft lengths. For example, in one embodiment, the shaft recognition sensor and control unit can be configured to define discrete full fire zone positions for shafts including jaw assemblies of one or more of 30 mm, 45 mm, and 60 mm. Additionally, the shaft recognition sensor and control unit can be configured to recognize when no shaft is coupled to the handle assembly and prevent actuation of the motor through some or all of the actuation zones when such a condition is recognized.

The full fire zone ends at a full fire position. The full fire position corresponds to a calculated position at which the control unit should detect a full fire current spike. However, in some embodiments, the control unit advances to the return zone only once a current spike is detected, which can occur either before or after this position due to a variety of factors including tissue thickness and articulation. Like the full fire start position, the control unit can incorporate sensor data from the shaft recognition sensor to assign different values for the full fire position based on a length of the jaw assembly coupled to the handle assembly. Furthermore, in some embodiments, the control unit can incorporate sensor data from the articulation sensor described above with reference to FIG. 19 to define adjusted positions of the full fire start position and full fire position.

Once the device has been fully fired, the control unit advances to the returning zone. In the returning zone, the control unit is configured to drive the motor at a relatively high speed. For example, in some embodiments, the control unit can drive the motor at between 70% and 100% duty cycle in the returning zone. In other embodiments, the control unit can drive the motor at between 85% and 100% duty cycle in the returning zone. In still other embodiments, the control unit can drive the motor at approximately 100% duty cycle until the actuation shaft is positioned at a position corresponding to jaws closed position of the jaw assembly. A user can then advance the control unit to the opening zone by pulling the trigger to drive the motor at 100% duty cycle to an actuation rack position corresponding to the jaws open position of the jaw assembly.

Figure 47:
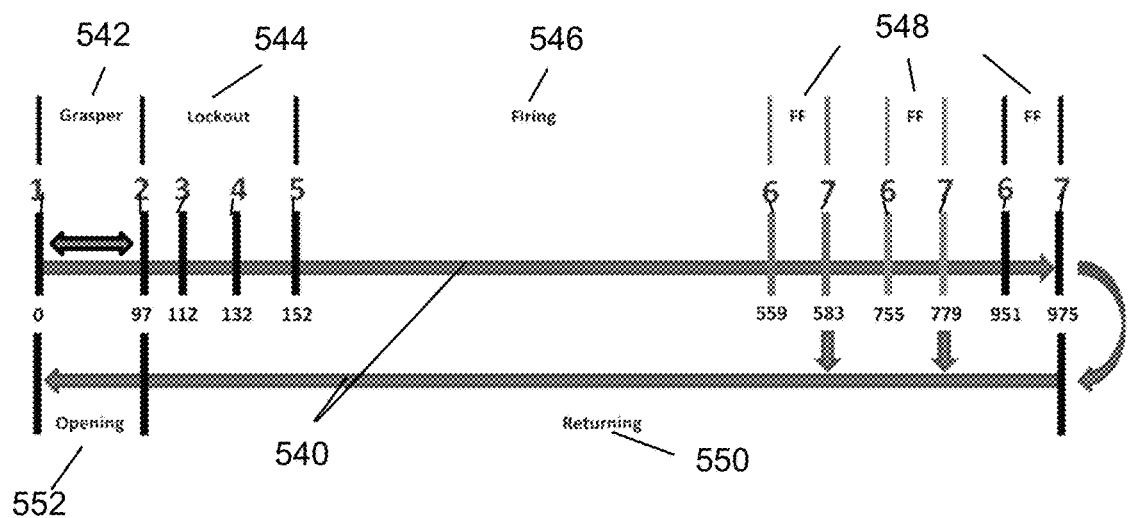
FIG. 47 is a schematic of one embodiment of motor control logic profile that can be implemented by a control unit of the powered handle of FIG. 2.
Figure 48:
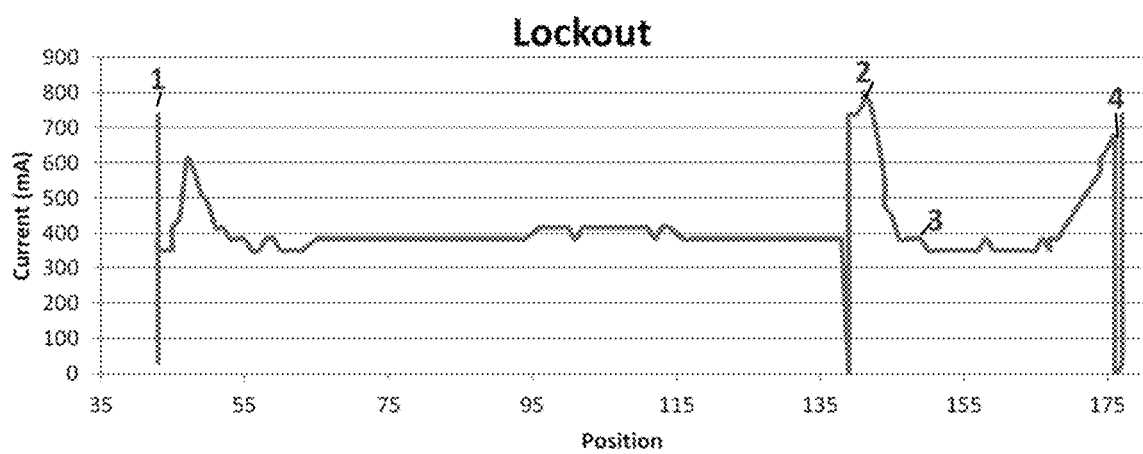
FIG. 48 is a plot of motor load versus actuation rack position for one exemplary jaw assembly grasping and pre-firing lockout for a powered handle such as the powered handle of FIG. 2.
Figure 49:
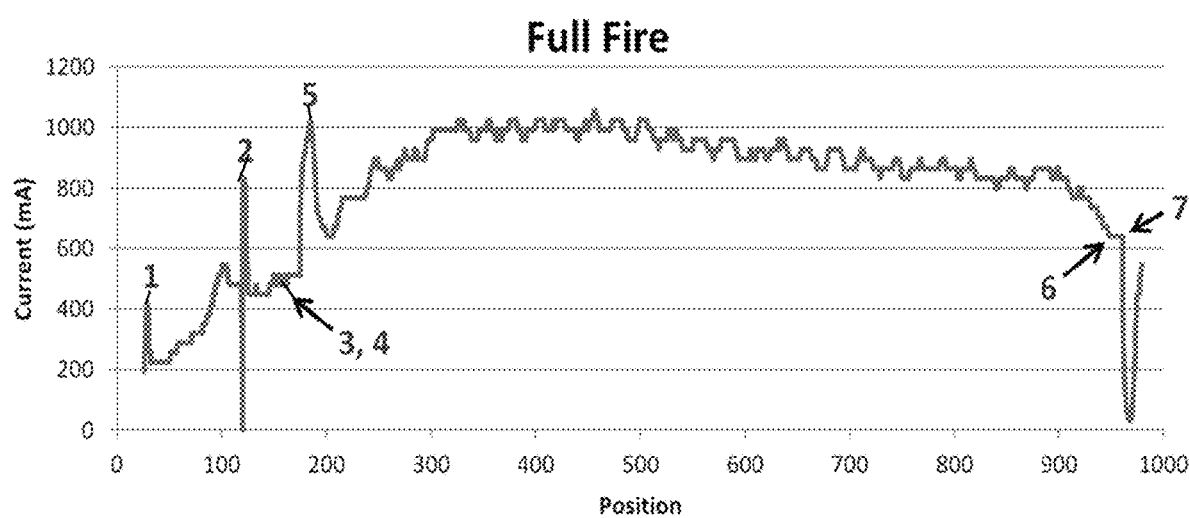
FIG. 49 is a plot of motor load versus actuation rack position for one exemplary jaw assembly grasping through full firing for a powered handle such as the powered handle of FIG. 2.

FIGS. 47-49 illustrate aspects of an exemplary operation of the handle assembly using an example of the motor drive logic profile discussed above. FIG. 47 illustrates a schematic view of a full firing and return operational cycle of a powered handle assembly including certain aspects of the motor drive logic profile. The central arrow 540 represents a position of the actuation rack starting from a calibrated '0' corresponding to a jaws open position of a coupled jaw assembly and increasing, as labeled, by an indicated number of 'counts' defined by monitoring an actuation rack sensor such as the actuation rack potentiometer described herein. The various zones discussed above are labeled astride the central arrow, and certain positions are numbered with: a first position corresponding to the jaws open position 1; a second position corresponding to the jaws closed position 2; a third position corresponding to the lockout low position 4; a fourth position corresponding to the lockout nominal position 4; a fifth corresponding to the lockout high position 5; a sixth position corresponding to the full fire start position 6; and a seventh position corresponding to the full fire position 7. The full fire start position 6 and the full fire position 7 are repeated to indicate different position values associated with different shaft geometries recognized by the shaft recognition sensor. While the above discussion includes certain motor operational speeds, positions, and jaw sizes, it is contemplated that in other embodiments, the control unit of the present handle assembly can incorporate a motor drive logic profile including different speeds, positions, and jaw sizes, or a motor drive logic profile incorporating sensor data from other sensors.

With reference to FIG. 47, the motor control logic profile can include a grasper zone 542 extending between the jaws open position 1 and the jaws closed position 2, a lockout zone 544 extending between the jaws closed position 2 and the lockout high position 5, a firing zone 546 extending between the lockout high position 5 and the full fire start position 6, a full fire zone 548 extending between the full fire start position 6 and the full fire position 7, a returning zone 550 extending from the full fire position 7 to the jaws closed position 2, and an opening zone 552 extending from the jaws closed position 2 to the jaws open position 1. While the illustrated embodiment of motor control logic profile includes a lockout zone 544 outside the grasper zone 542, as further discussed with respect to the lockout mechanisms of FIGS. 32-41, that the lockout zone can overlap with the grasper zone such that the control system can include a lockout module as discussed with reference to FIGS. 58-61.

FIGS. 48 and 49 illustrate plots of motor load (in milliamps) vs. actuation rack position (in counts) in an exemplary firing stroke of a handle assembly operating with an embodiment of motor control logic profile discussed herein. FIG. 48 illustrates one example of motor load through the closing and lockout zones, where a lockout motor load spike has been encountered during the lockout zone, between the lockout low position 3 and the lockout nominal position 4 of the actuation rack. As discussed above, encountering such a motor load spike would result in the control unit returning the actuation rack to a position corresponding to the jaws open configuration of the end effector. As illustrated, the motor load also spikes around the jaws closed position 2. This load spike can correspond to a motor stop and restart at a different speed as the control unit advances from the grasper zone to the lockout zone. This initial movement load spike can take a small translation of the actuation rack, for example approximately 15 counts, to settle. Thus, in the lockout zone, the control unit does not monitor for load spikes corresponding to a lockout condition until the lockout low position 3, which is beyond the transient load spike at the beginning of the lockout zone.

FIG. 49 illustrates one example of motor load versus actuation rack position 1 from the jaws open through a full fire position 7. As illustrated, the motor load can temporarily spike at actuation rack positions corresponding to the initiation of the lockout zone at a jaws closed position 2 and the initiation of the firing zone at the lockout high position 5. At these positions, the control unit can direct motor speed changes that temporarily increase the monitored motor load.

Figure 50:
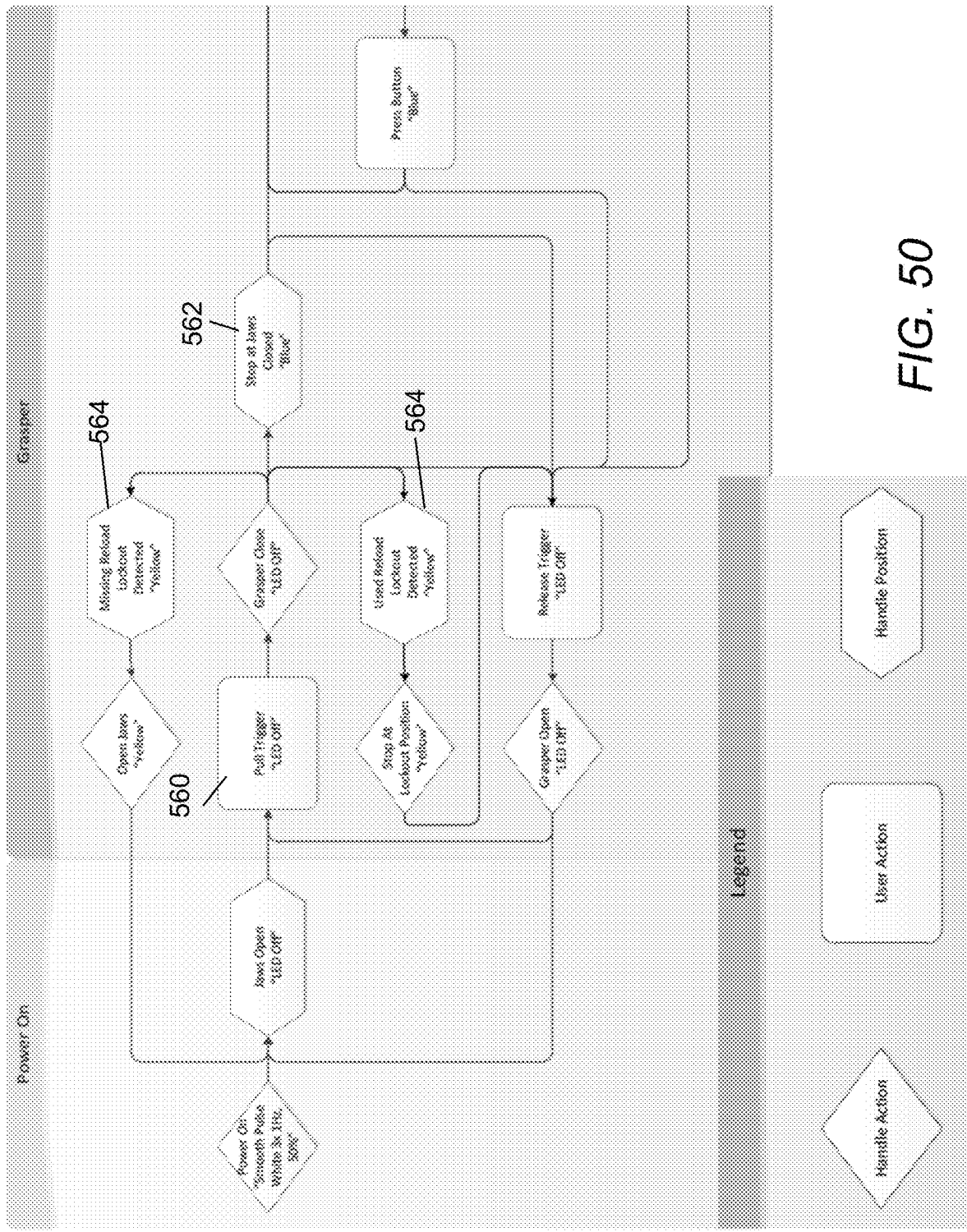
FIG. 50 is schematic diagram of one embodiment of motor control logic profile that can be implemented by a control unit of the powered handle of FIG. 2 operating in a powered on and tissue grasping configurations.
Figure 51:
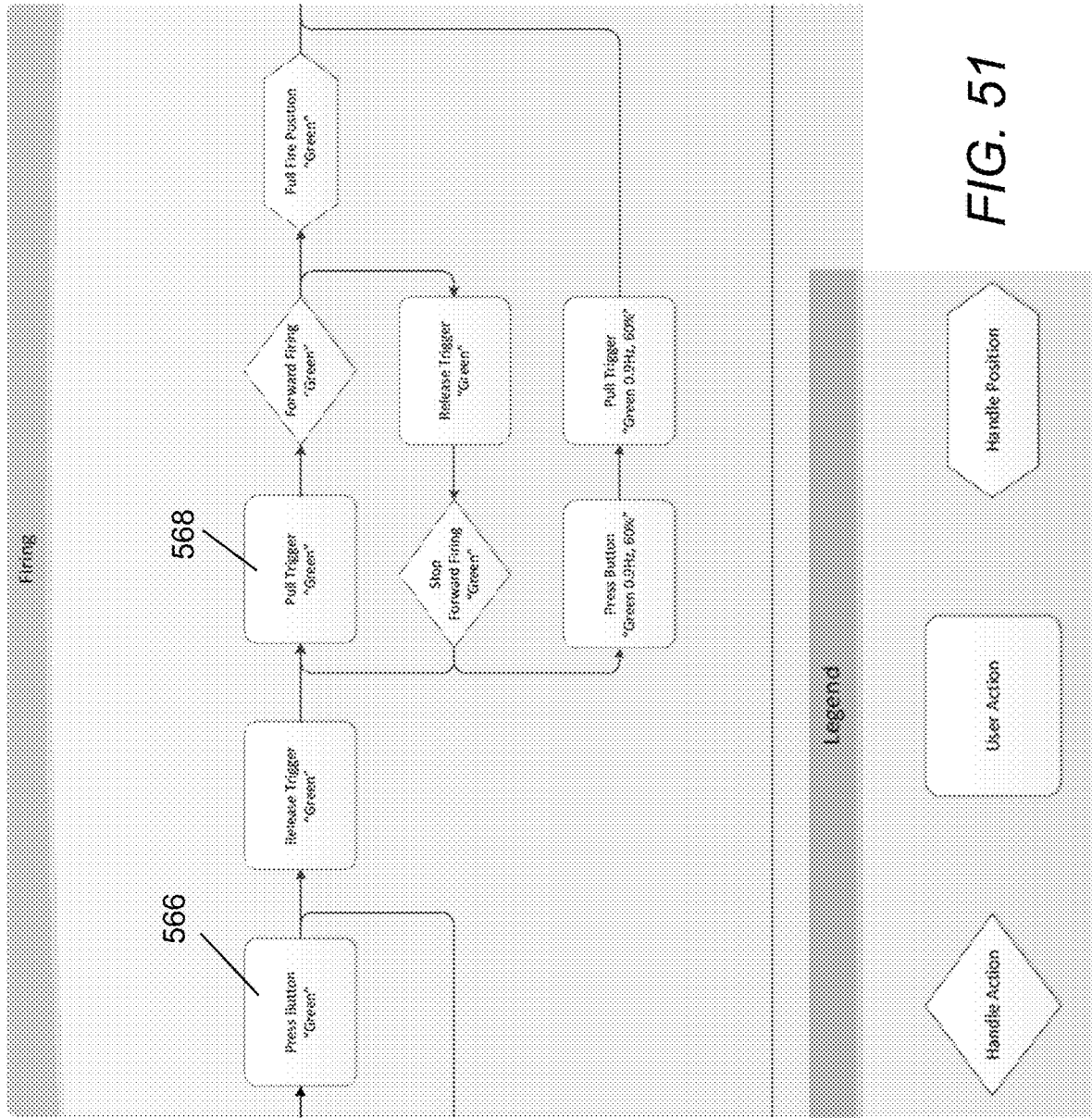
FIG. 51 is schematic diagram of the embodiment of motor control logic profile of FIG. 50 operating in a firing configuration.
Figure 52:
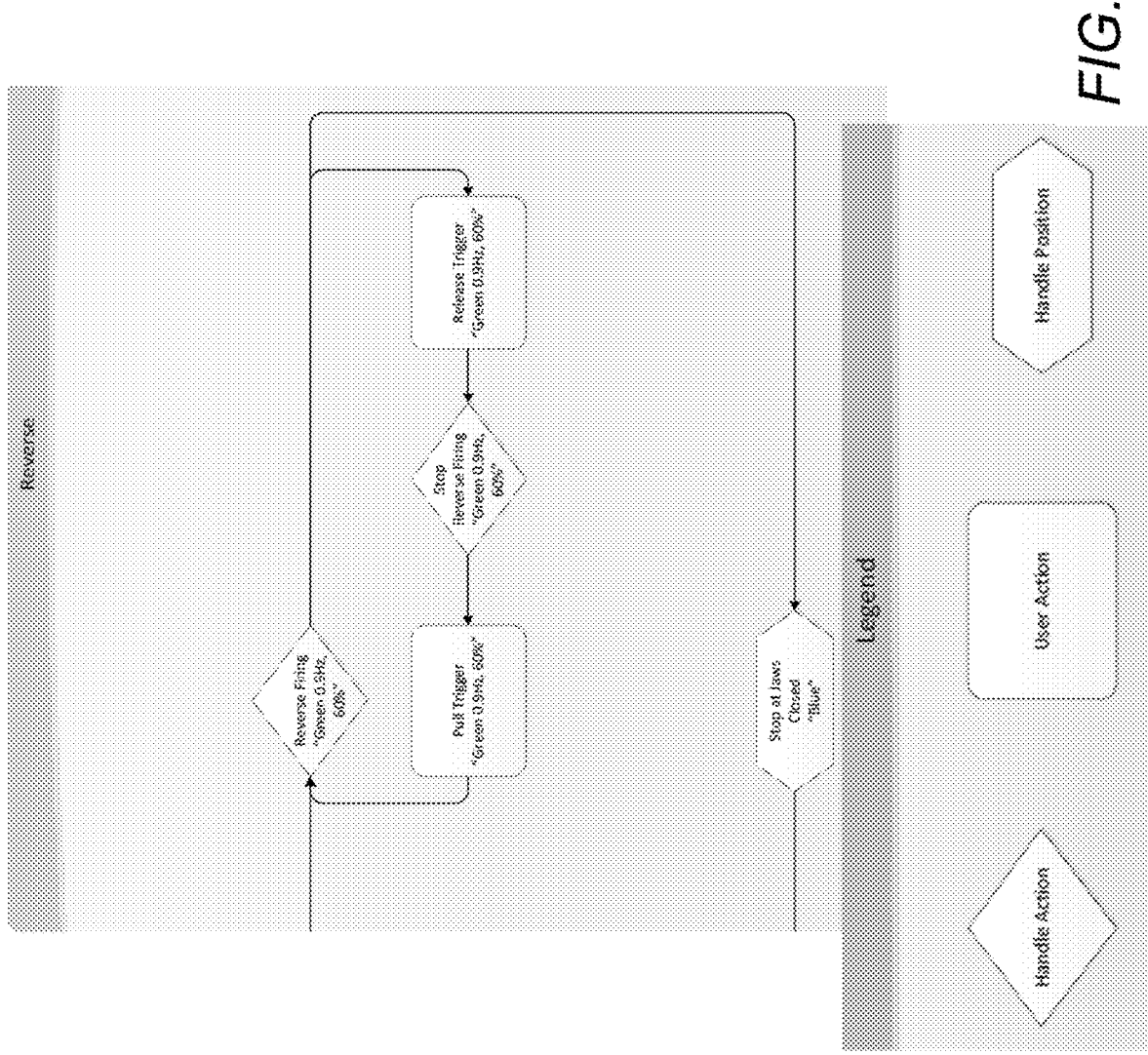
FIG. 52 is schematic diagram of the embodiment of motor control logic profile of FIG. 50 operating in a reverse configuration.
Figure 53:
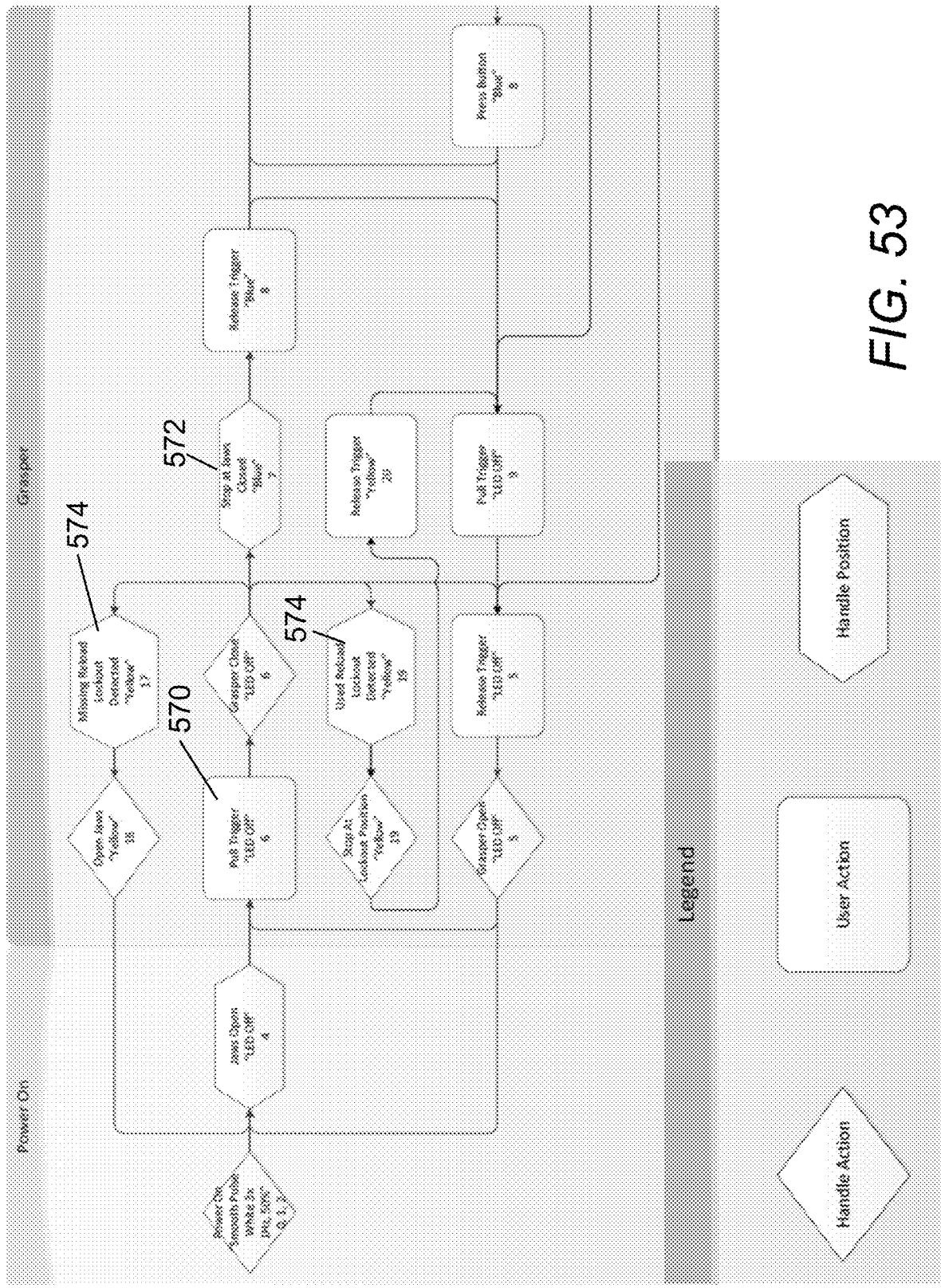
FIG. 53 is schematic diagram of another embodiment of motor control logic profile that can be implemented by a control unit of the powered handle of FIG. 2 operating in a powered on and tissue grasping configurations.
Figure 54:
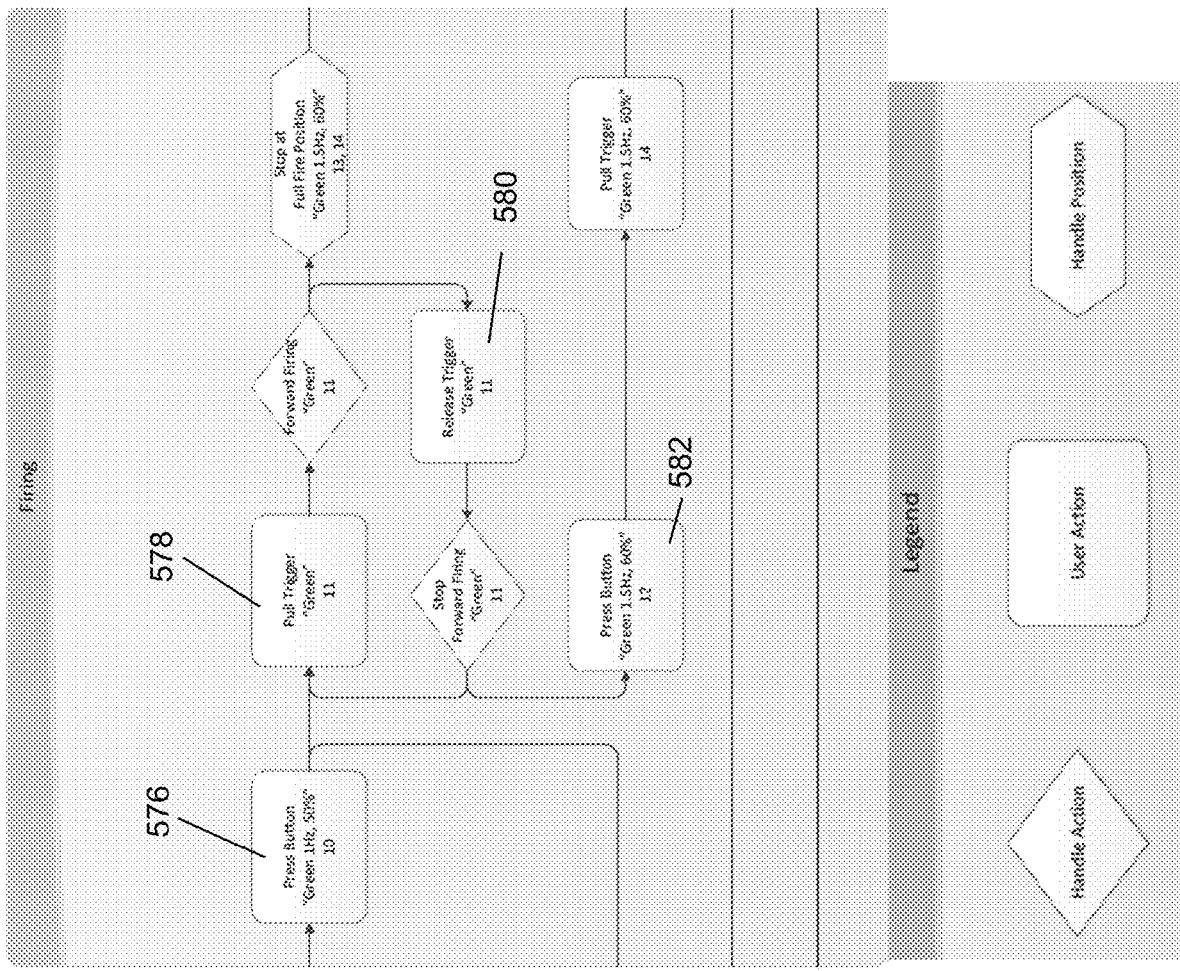
FIG. 54 is schematic diagram of the embodiment of motor control logic profile of FIG. 53 operating in a firing configuration.
Figure 55:
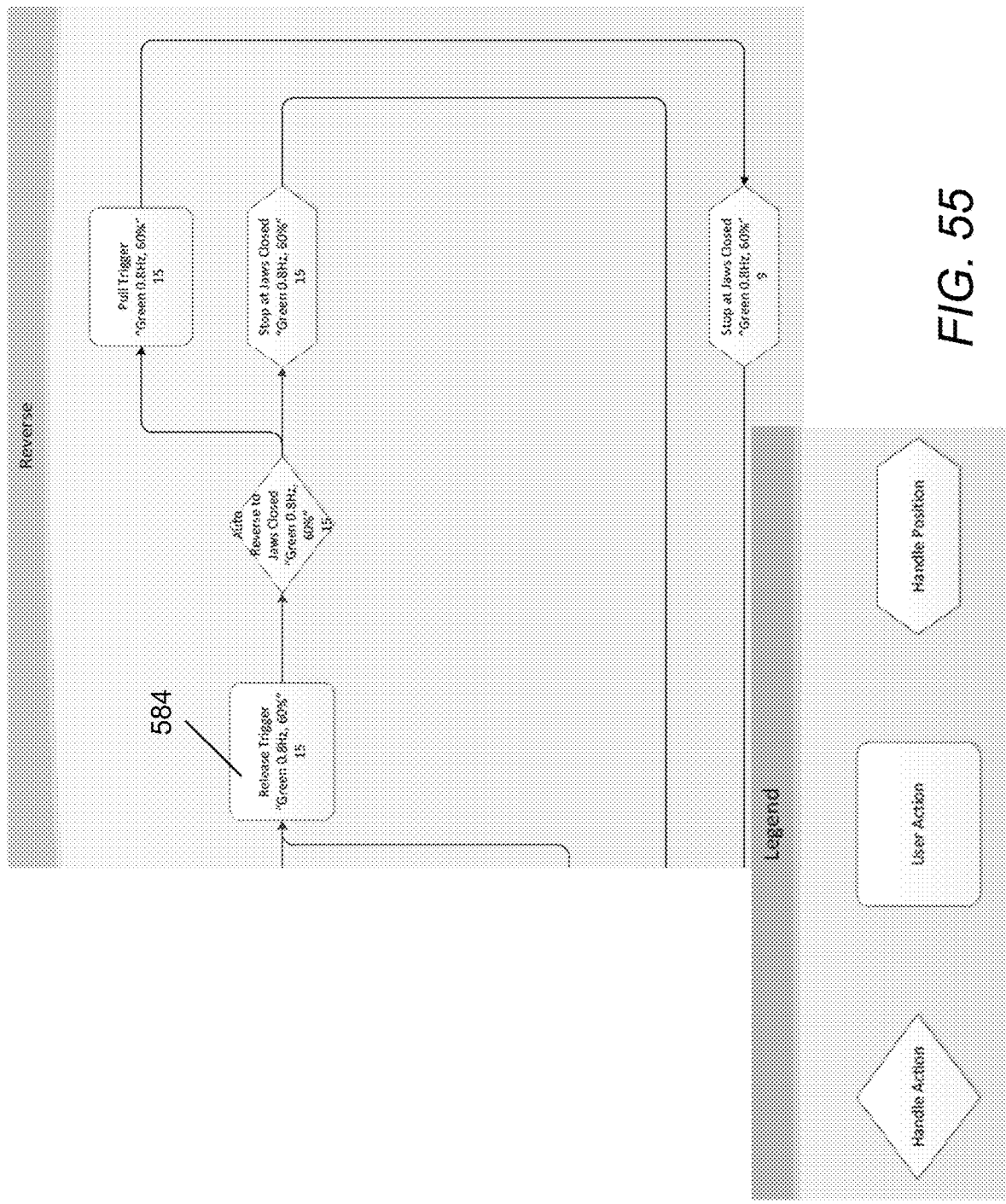
FIG. 55 is schematic diagram of the embodiment of motor control logic profile of FIG. 53 operating in a reverse configuration.

As discussed above with respect to FIGS. 45-46, the microcontroller can be configured with a control system to integrate user inputs and system hardware inputs in grasping, firing, and return sequences of the powered handles described herein. The control system can be embodied in a software or firmware system operating on the microcontroller. In some embodiments, the microcontroller can be configured with a single control system defining an operational sequence of the powered handle. In other embodiments, the microcontroller can be configured with more than one control system such that a user can select a desired operational sequence for desired stapling operation characteristics. Certain aspects of two exemplary control systems are discussed with respect to the schematic diagrams of FIGS. 50-52 and 53-55. In general, the control system of FIGS. 50-52 is configured to require manual input from a user in the form of actuation of a trigger or firing button before the handle will commence an operation. Desirably, such a control system can provide a high degree of user control and predictability to the stapling operation. The control system of FIGS. 53-55 is configured to automate certain portions of the stapling operation such that they proceed without further user input. Desirably, such a control system can facilitate more efficient stapling sequences and reduce the potential for user fatigue. It is contemplated that in other embodiments, a control system can include some but not all of the automated features of the system illustrated in FIGS. 53-55 in a more manually controlled system such as that of FIGS. 50-52. In still other embodiments of control system it is contemplated that further automated operational sequences can be added to the system of FIGS. 53-55.

With reference to FIGS. 50-52, block diagrams schematically illustrating an operational flow chart for exemplary grasping (FIG. 50), firing (FIG. 51), and return (FIG. 52) sequences of the control systems are illustrated. As illustrated, the control system integrates user inputs from the trigger and firing button (illustrated as 'user actions' in generally rectangular blocks), as well as handle positioning information (illustrated as 'handle positions,' in elongate hexagonal blocks) reported from various sensors and monitors, and corresponding handle actions (illustrated as 'handle actions' in diamond shaped blocks) as a handle assembly is operated to advance the jaw assembly from a fully open condition to a fully closed condition to a firing sequence, then back to the fully open condition.

With reference to FIG. 50, certain aspects of a power on and grasping operations of the control system are schematically illustrated. In addition to the various shapes schematically illustrating certain aspects of the control system as described above and illustrated in the Legend, one example of user feedback indicia, which can be presented for example in a multicolor LED such as the light ring described with respect to FIGS. 42-44, is described in quotation marks, with one example of a selected color, a flashing frequency, and duty cycle to indicate an operational condition of the handle to the user. It is contemplated that in other embodiments, other user feedback indicia can be presented in connection with the control system of FIGS. 50-52.

With continued reference to FIG. 50, an initial powered on operation is indicated with a smooth pulse of a white color. In an initial position, the jaw assembly is open, and the stapler is in a grasping configuration in which the jaws can be opened and closed responsive to movement of the trigger 560. If an unfired reload cartridge is present in the jaw assembly, the handle assembly is configured to operate such that movement of the jaw assembly between the open and closed position generally corresponds to movement of the trigger from an initial position spaced apart from the handle to a squeezed position approximated with the handle. Advantageously, this generally proportional operation of trigger and jaw assembly allows a user to repeatedly open and close the jaws to precisely find a desired stapling location and tissue placement within a surgical field.

With continued reference to FIG. 50, in the illustrated control system, if a user fully approximates the trigger against the handle, the jaws are closed and the user feedback indicia indicates this closed configuration 562 with a blue illumination. With the jaws in this closed state, the illustrated control system will maintain the handle in a grasping configuration absent further user input. Thus, if the user releases the trigger from the fully approximated position, the jaws will open (to a position corresponding to the amount of trigger release). Further user input is required to configure the control system to direct the handle assembly to enter a firing configuration.

With continued reference to FIG. 50, if no reload is present in the jaw assembly, or a used or partially used reload is present in the jaw assembly, the jaws will not be fully closed. In the illustrated control system, the user feedback indicia displays a yellow light 564, prompting a user to release the trigger to allow the jaws to return to an open configuration.

With reference to FIGS. 50 and 51, operation of grasping and firing configurations of a control system of the powered handle are schematically illustrated. In the illustrated control system, with the trigger held in a fully approximated position and the jaws fully closed (indicated by solid blue lighted user feedback indicia), a user must depress a firing button 566 on the handle for the control system to direct the handle to enter a firing configuration (FIG. 51). Once the firing configuration has been entered, the user feedback indicia displays a solid green light. With the trigger maintained in the fully approximated position, a second press of the button causes the control system to direct the handle to return to the grasping configuration and causes the user feedback indicia to display a blue light. With the handle assembly in the firing configuration and user feedback indicia displaying a green light, to initiate firing, a user first releases the trigger, then approximates the trigger 568, holding it in the fully approximated position to direct the handle to power the motor and advance a firing member in the jaw assembly towards a fully fired position in which all the staples have been deployed from the stapler. If a user desires to pause the staple firing, releasing the trigger will cause the control system to direct the motor to stop. If a user desires to return to a firing operation from the paused condition, the user can reapproximate the trigger to reenter the firing operation. Alternately, from this paused condition, with the trigger released, if a user desires to discontinue stapling, the user can depress the button, which causes the control system to direct the handle to bypass the fully fired position and enter a return configuration, and results in a distinct, pulsing of the user feedback indicia to reflect this return configuration.

With reference to FIGS. 51 and 52, certain aspects of firing and return operations of a control system for a powered stapler handle are schematically illustrated. If a user has caused the control system to direct the handle to enter the reverse configuration, either by fully executing a firing operation or by pausing then stopping a firing operation by releasing the trigger and subsequently depressing the firing button, maintaining the trigger in an approximated condition causes the control system to direct the handle to operate in a reverse direction to retract the firing member longitudinally within the jaw assembly. If a user desires to pause the return operation, the user can release the trigger. The user can then resume the return operation by reapproximating the trigger with respect to the handle. Advantageously, this manual control of the return operation can provide a user the option of inspecting staple formation and tissue compression, should it be desired, without fully retracting the firing member. The return operation is completed with the jaw assembly in the closed position and the trigger still approximated to the handle body.

With reference to FIGS. 50 and 52, Upon completion of the return operation, the control system directs the handle assembly to return to the grasping configuration. The user can then release the trigger to return the jaw assembly to an open configuration. Advantageously, this manual control of jaw opening following firing and return operations allows a user to monitor and allow additional time for tissue compression before fully releasing the jaw assembly from stapled tissue.

With reference to FIG. 53, certain aspects of a power on and grasping operations of the control system of FIGS. 53-55 are schematically illustrated. In the schematic illustration of the control system of FIGS. 53-55, the block shapes and user feedback indicia correspond to the conventions presented with respect to the control system of FIGS. 50-52.

With continued reference to FIG. 53, an initial powered on operation is indicated with a smooth pulse of a white color. In an initial position, the jaw assembly is open, and the control system directs the handle to remain in a grasping configuration in which the jaws can be opened and closed responsive to movement of the trigger 570. If an unfired reload cartridge is present in the jaw assembly, the handle assembly is configured to operate such that movement of the jaw assembly between the open and closed position generally corresponds to movement of the trigger from an initial position spaced apart from the handle to a squeezed position approximated with the handle. Advantageously, this generally proportional operation of trigger and jaw assembly allows a user to repeatedly open and close the jaws to precisely find a desired stapling location and tissue placement within a surgical field.

With continued reference to FIG. 53, in the illustrated control system, if a user fully approximates the trigger against the handle, the jaws are closed and the user feedback indicia indicates this closed configuration 572 with a blue illumination. The control system directs the handle to automatically maintain this closed configuration even when the trigger is subsequently released. With the jaws in this latched closed state, the illustrated control system will maintain the handle in a grasping configuration with the jaws fully closed absent further user input. Advantageously, this latched closed position allows a user to release the trigger and maintain tissue compression while manipulating the handle to obtain visibility at the surgical site. If a user desires to unlatch the jaw assembly from the latched closed configuration, the user can reapproximate the trigger, which causes the control system to direct the handle to position the jaws in an unlatched closed configuration (with a corresponding "off" user feedback indicia). Subsequently releasing the trigger causes the control system to direct the handle to move the jaws to an open configuration.

With continued reference to FIG. 53, if no reload is present in the jaw assembly, or a used or partially used reload is present in the jaw assembly, the jaws will not be fully closed. In the illustrated control system, the user feedback indicia displays a yellow light 574, prompting a user to release the trigger to allow the jaws to return to an open configuration.

With reference to FIGS. 53 and 54, operation of grasping and firing configurations of a control system of the powered handle are schematically illustrated. In the illustrated control system, with the trigger released and the jaws in the fully closed and latched configuration (indicated by solid blue lighted user feedback indicia), a user must depress a firing button on the handle for the control system to direct the handle to enter a firing configuration (FIG. 54). Once the firing configuration has been entered, the user feedback indicia displays a flashing green light. With the trigger maintained in the fully released position, a second press of the button 576 causes the control system to direct the handle to return to the grasping configuration with the jaw assembly in the latched closed configuration and causes the user feedback indicia to display a blue light. With the handle assembly in the firing configuration and user feedback indicia displaying a flashing green light, to initiate firing, a user approximates the trigger 578, holding it in the fully approximated position to cause the control system to direct the handle to power the motor and advance a firing member in the jaw assembly towards a fully fired position in which all the staples have been deployed from the stapler. The user feedback indicia displays a solid green illumination once the trigger has been approximated in this firing operation. Once the fully fired position has been reached, the control system directs the handle to stop movement of the motor and directs the user display indicia to present a distinct pattern indicating the handle has entered the return configuration. If a user desires to pause the staple firing during the firing operation, releasing the trigger 580 will cause the control system to direct the motor to stop. If a user desires to return to a firing operation from the paused condition, the user can reapproximate the trigger 578 to reenter the firing operation. Alternately, from this paused condition, with the trigger released, if a user desires to discontinue stapling, the user can depress the button 582, which causes the control system to direct the handle to bypass the fully fired position and enter a return configuration, and results in a distinct, pulsing of the user feedback indicia to reflect this return configuration.

With reference to FIGS. 54 and 55, certain aspects of firing and return operations of a control system for a powered stapler handle are schematically illustrated. If a user has caused the control system to direct the handle to enter the reverse configuration, either by fully executing a firing operation or by pausing then stopping a firing operation by releasing the trigger and subsequently depressing the firing button, returning the trigger to an approximated condition, then releasing the trigger 584 causes the control system to direct the handle to operate in a reverse direction to retract the firing member longitudinally within the jaw assembly. This return operation proceeds automatically until the firing member has been retracted to a jaws closed position within the jaws such that the user can release the trigger during the return operation. The user can then resume the return operation by reapproximating the trigger with respect to the handle. Desirably, this automated control of the return operation can enhance user convenience by reducing the need for user interaction once staple firing is complete. The return operation is completed with the jaw assembly in the closed position.

With reference to FIGS. 53 and 55, upon completion of the return operation, the control system directs the handle assembly to return to the grasping configuration with the jaws in the latched closed configuration and the user feedback indicia illuminated in blue. The user can then reapproximate, then release the trigger to unlatch the closed jaw assembly and return the jaw assembly to an open configuration. Advantageously, this manual control of jaw opening following firing and return operations allows a user to monitor and allow additional time for tissue compression before fully releasing the jaw assembly from stapled tissue.

Haptic Feedback Module

Figure 56:
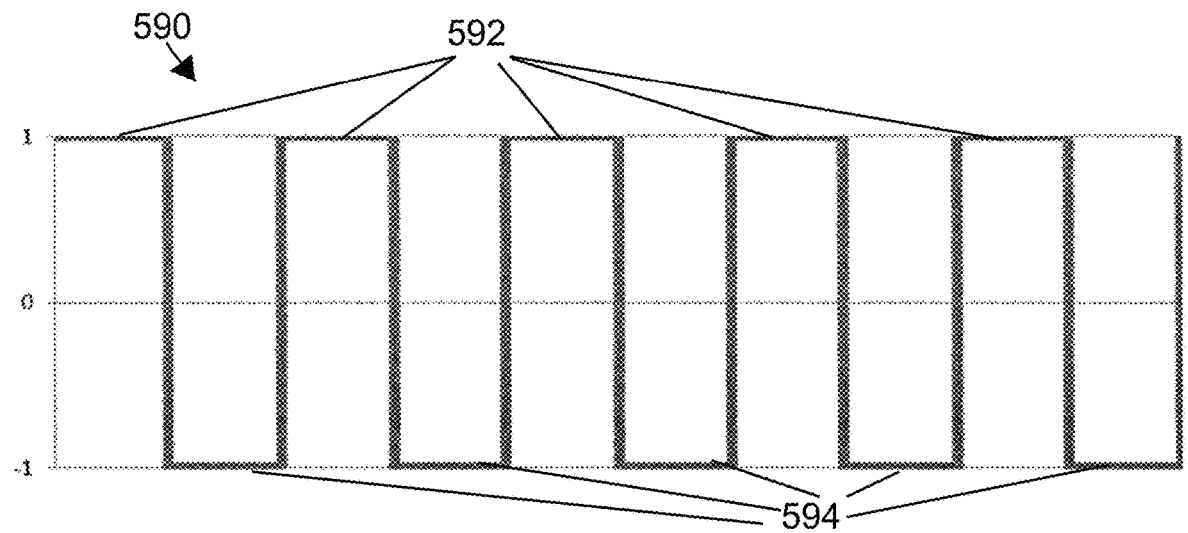
FIG. 56 is schematic diagram of an embodiment of motor drive profile of a haptic feedback module.
Figure 57:
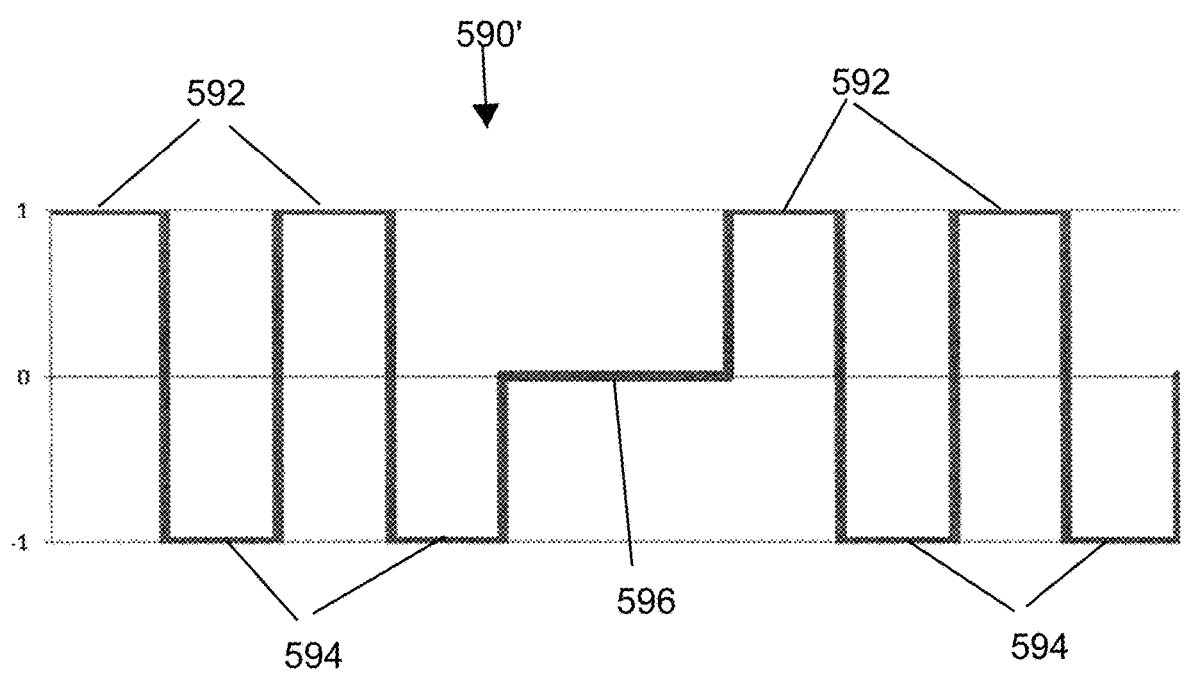
FIG. 57 is schematic diagram of another embodiment of motor drive profile of a haptic feedback module.

In addition to the light ring user display discussed with reference to FIGS. 42-44, additional user feedback can be provided through the use of haptic feedback such as a buzzing or vibrating handle in certain patterns to indicate certain operational states of the handle assembly. In certain embodiments, a dedicated haptic feedback generator such as a vibrating feedback motor can be positioned within the handle assembly and configured to provide user feedback in certain conditions. However, in certain embodiments, haptic feedback can desirably be provided without the use of additional components. As the handle assembly can include a DC motor and reduction drive to provide the linear actuation force for transecting and approximating tissue, this motor and drive system can include backlash resulting from mechanical clearances between components. Due to this backlash, there is a period of initial actuation of the DC motor output shaft that does not result in movement of the actuator and jaw assembly of the stapling system. Accordingly, in some embodiments, the DC motor can be driven clockwise and counterclockwise in rapid succession, resulting in a noticeable vibration of the handle assembly to the user without a significant translation of the actuator. To achieve this haptic feedback mode of the DC motor, the control system can include a haptic feedback module which can be activated to drive the motor in a substantially square wave motor drive waveform profile 590 alternating between peaks of clockwise rotation 592 and counterclockwise rotation 594 each peak having a duration of a predetermined time that does not produce movement of the actuation shaft due to backlash of the motor and drive system. FIG. 56 illustrates an exemplary motor drive profile 590 to produce haptic feedback with a handle buzz or vibrate sensation in a handle assembly. Additionally, the square waveform, and resulting motor vibration, can be altered by, for example, introducing a depowered pause or delay between adjacent peaks of the waveform. FIG. 57 illustrates an exemplary motor drive waveform profile 590' incorporating a depowered time delay 596 among the alternating peaks of clockwise rotation 592 and counterclockwise rotation 594 to produce a pulsing sensation with the haptic feedback. Thus, the haptic feed module can be configured to produce different patterned or pulsating buzzing or vibrating patterns that can correspond to different operational conditions of the handle assembly. While the exemplary motor drive waveform profiles 590, 590' are illustrated as idealized square waves, it is contemplated that in other embodiments, the haptic module can include other waveform profiles configured to produce movement of the motor without significant movement of the actuation shaft.

Lockout Control Modules

As discussed above with reference to FIGS. 47 to 49, in certain embodiments, the control system can be configured to monitor current within a defined 'lockout zone' of actuator position. In these embodiments, the control system can rely solely on a current threshold to determine the presence of a lockout mechanism engagement. In certain embodiments, the current threshold was determined based off a sample at the beginning of the lockout zone plus a constant 300 mA, indicating that a reload lockout had not been defeated and travel of the actuator had been arrested. However, this one factor lockout sensing module of the control system is most effective outside of the grasping region as the actuator is entering a firing stroke of the jaw assembly. Outside the grasping region, the control system directs constant pwm operation of the motor. Moreover, when the actuator had been advanced distally beyond the grasping region, tissue clamping had already occurred, so any potential current fluctuations attributable to tissue thickness and consistency variations would be minimized. However, the two-position lockout mechanisms described above with reference to FIGS. 32-41 can require further refinement of lockout detection modules of the control system as they provide certain operational advantages when the lockout mechanisms are engageable within the grasper zone.

As discussed above with respect to FIGS. 32-41, the two-position lockout mechanisms can desirably engage at two distinct actuator positions corresponding to an empty jaw assembly and an at least partially fired reload. In some embodiments, these locked out actuator positions are relatively close to one another as lockout notches formed in the firing beam can be substantially contiguous. Moreover, in certain embodiments, each of these actuator positions can fall within the grasping zone or region of control system operation. In the grasping region, the control system can be configured to provide a user full control over the opening and closing of the jaws of the jaw assembly prior to entering a firing state. The user can partially close the jaws, re-open, and re-close without limit. In certain embodiments, in the grasping region, the trigger is mapped to proportional jaw closure, which means pulling the trigger 25% will result in 25% jaw closure. However, every time the user pauses, opens, or closes the jaws, the motor stops and restarts. It takes additional power for the motor to overcome inertia and ramp up to full speed, resulting in a large momentary current spike. Moreover, as the jaw assembly typically compresses tissue during jaw closure in the grasping region, the load on the motor can be elevated in response to thicker or denser tissues positioned between the jaws. Accordingly, in some instances, a lockout module in the control system based on current detection alone can lead to false positive indications where one or more lockout mechanisms can engage at an actuator position in the grasper region due to transient user input and tissue compression conditions.

Figure 58:
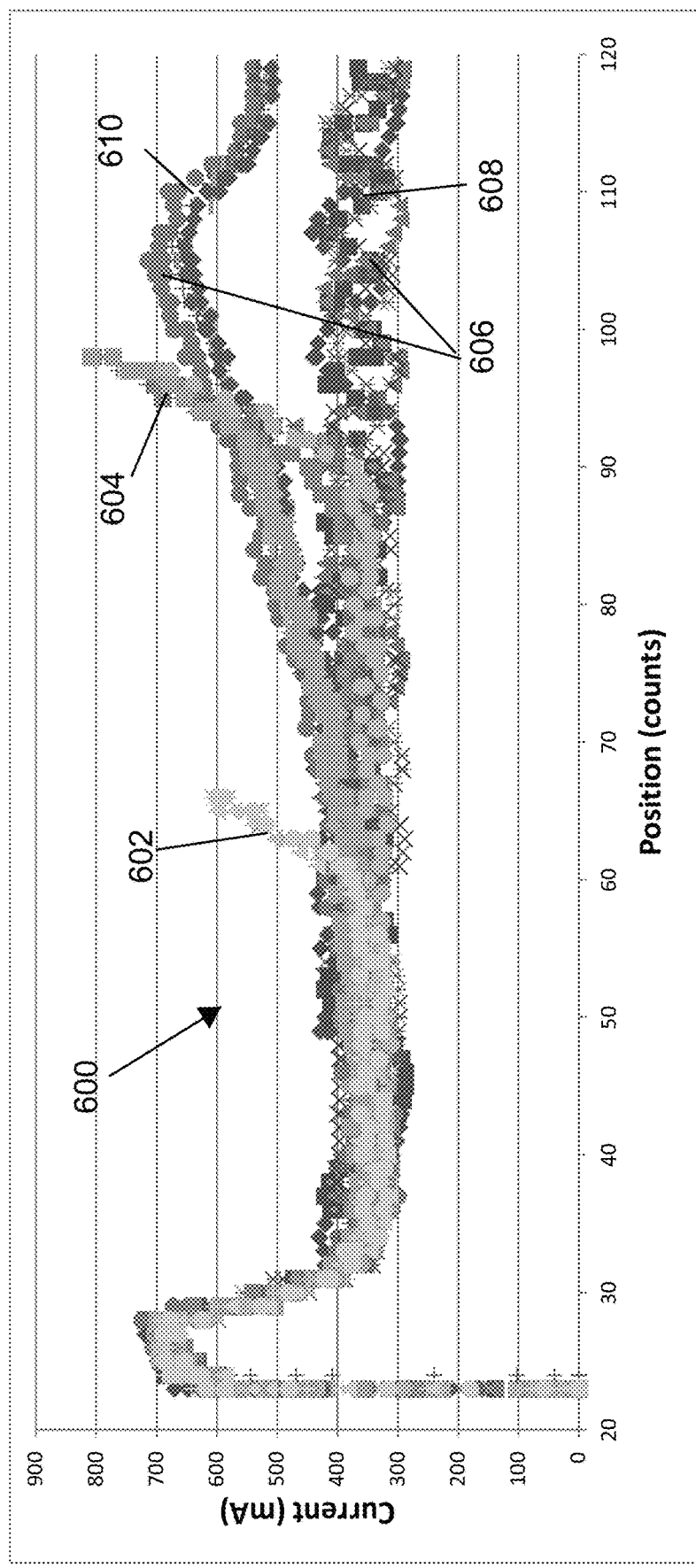
FIG. 58 is an exemplary plot of measured current draw versus actuation shaft position over certain operational conditions for an embodiment of powered handle assembly.

With reference to FIG. 58 an overlap plot of 25 exemplary current profiles 600 for various operational conditions of a powered stapler is illustrated. The plot illustrates motor load or current draw (measured in milliamps) tracked over actuated position of the actuation shaft or actuator, measured in 'counts' of a position detection device, such as a potentiometer. It is noted that the loads experienced and position detected can vary based on the size and configuration of the elongate shaft, jaw assembly, and lockout mechanisms in addition to the specifications of the motor, battery, and gearing. Thus, the plot is merely illustrative of performance of certain embodiments of powered stapler. The plot illustrates current versus position for a powered handle assembly operating with no reload 602 to trigger an empty jaw assembly lockout mechanism as discussed above with respect to FIG. 41, operating with a fired reload 604 to trigger a fired reload lockout mechanism as discussed above with respect to FIG. 40, and operating with an unfired reload 606 to complete a grasping operation with no lockout mechanism engagement. The plot illustrates data from operation of the handle assembly with an unfired reload with both light 608 and heavy 610 simulated tissue loads positioned in the jaw assembly for comparison of the impact of tissue compression on current draw. Despite the differing lockout locations and nominal current draws, the slope of the current profile when a lockout condition engages appears consistent between all tests.

Figure 59:
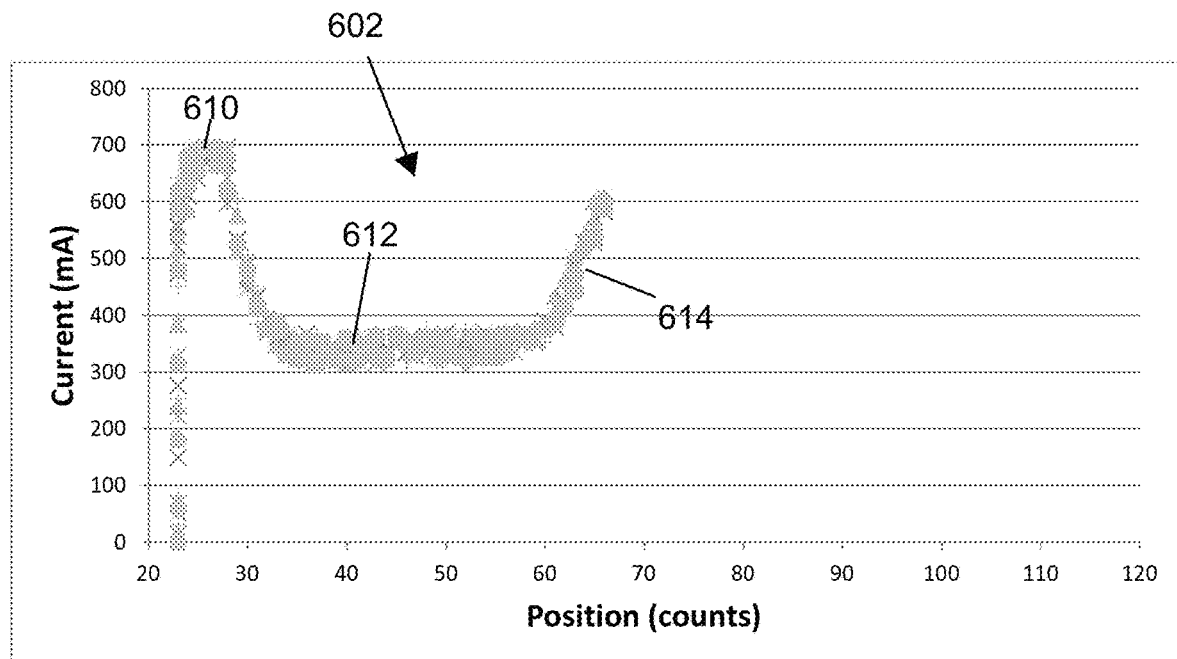
FIG. 59 is an exemplary plot of measured current draw versus actuation position over a first lockout engagement condition for an embodiment of powered handle assembly.
Figure 60:
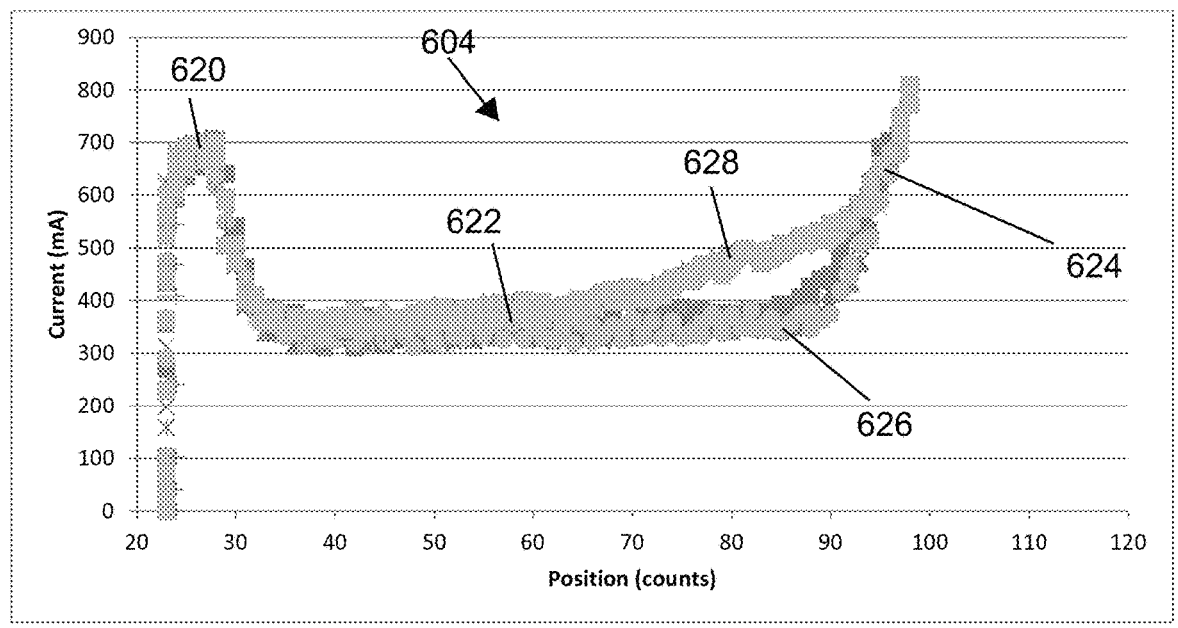
FIG. 60 is an exemplary plot of measured current draw versus actuation position over a second lockout engagement condition for an embodiment of powered handle assembly.
Figure 61:
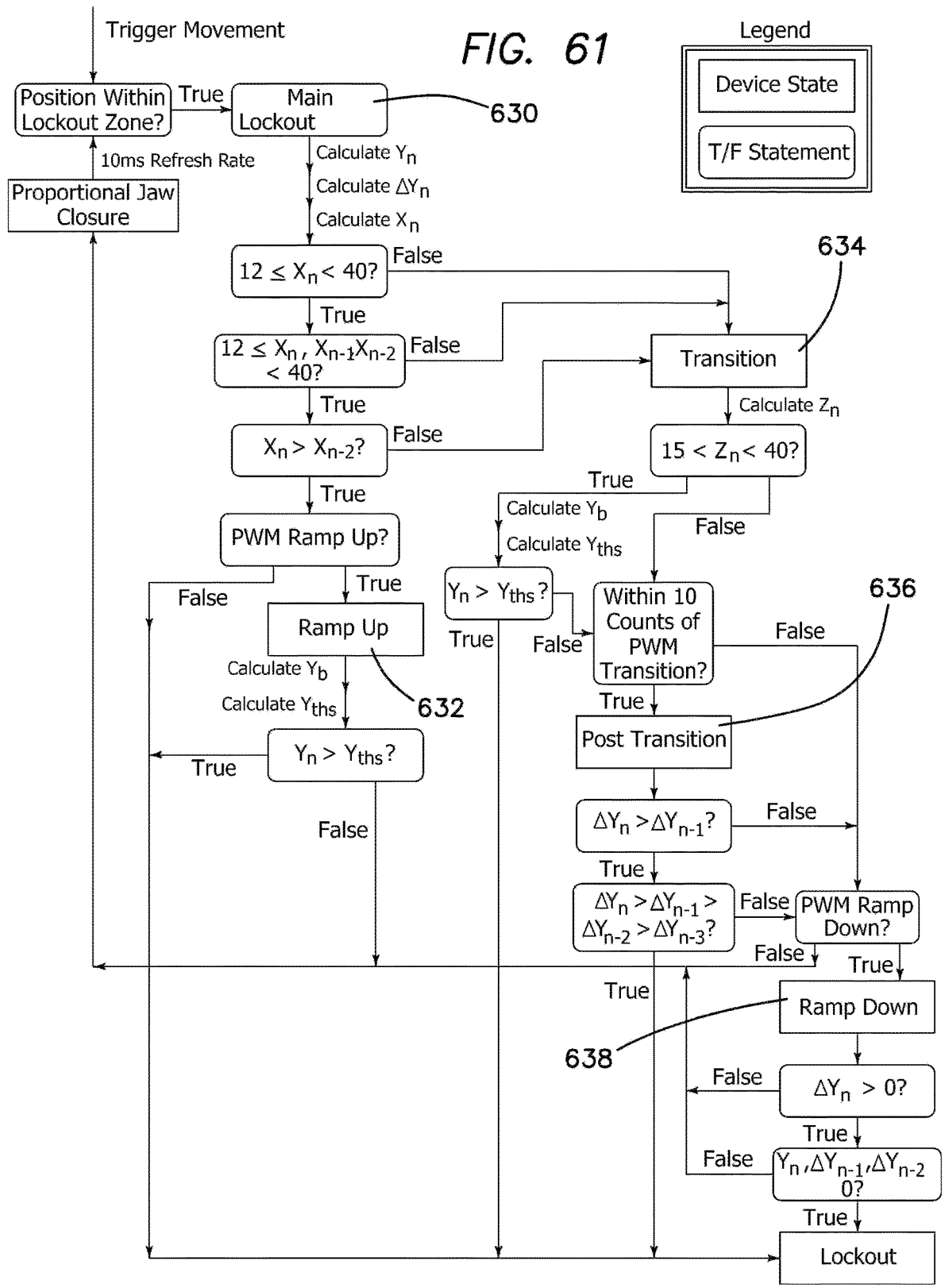
FIG. 61 is an exemplary lockout mechanism control logic profile for an embodiment of powered handle assembly.

In terms of lockout conditions that can be monitored by the control system, time and position can be unreliable and their rate of change is inconsistent between different loads that may be generated in a grasping zone of actuator travel. A current threshold alone can be falsely triggered by current draw conditions generated in normal grasper usage, and the voltage varies as the batteries are drained. However, one consistent lockout condition is the slope of the current profile with respect to actuator position as illustrated in FIG. 58, which falls within a distinct acceptance range when a lockout condition is present. Nominal current draw exhibits a lower slope, while grasper usage has a much steeper slope. Except for rare occurrences, a lockout engagement has a unique current vs. time plot that falls between the other cases. A lockout slope acceptance range for a particular configuration of elongate shaft can be calculated by examining the lockout slopes from a large sample size. In certain embodiments, the control system can include a lockout module which monitors the slope of the current draw with respect to actuation shaft position to detect whether a current profile slope falls within the lockout acceptance range, indicating a lockout mechanism has engaged. The lockout module of the control system can be configured to disengage the motor and configure the control system to take further actions discussed with respect to the motor drive profiles of FIGS. 50-55 upon indication of engagement of a lockout mechanism 564, 574. FIG. 59 illustrates plotted motor current draw data versus actuator position for exemplary actuation sequences with not reload 602 such that the empty jaw assembly lockout mechanism of FIG. 41 has been engaged. The plotted data reflects an initial current spike 610, a nominal current draw region 612, and a lockout engagement region 614 having a relatively consistent current profile slope. FIG. 60 illustrates plotted motor current draw data versus actuator position for exemplary actuation sequences with a previously-fired reload 604 where the fired reload lockout mechanism of FIG. 40 has been engaged. The plotted data reflects an initial current spike 620, a nominal current draw region 622, and a lockout engagement region 624 having a relatively consistent current profile slope. The plotted data includes exemplary actuation sequences with light tissue compression 626 by a jaw assembly and exemplary actuation sequences with heavy tissue compression 628 by a jaw assembly to illustrate the consistency of the slope of the current profile in the lockout engagement region 624 regardless of tissue load in the jaw assembly.

In certain embodiments, the lockout module of the control system can be further refined to provide more consistent lockout engagement detection even in cases of transient inconsistencies in the motor draw versus position monitoring that would otherwise indicate a slope corresponding to engagement of a lockout mechanism. In certain instances, the current profile can be prone to instantaneous inconsistencies due to varying tissue density, drivetrain component wear, or delayed data collection. The current can temporarily deviate from the expected slope if one of the gears has a nick or a burr, or if an unusually thick pocket of tissue is compressed. To combat these fluctuations, in certain embodiments of lockout module in the control system, the change in current (slope) can be averaged across a plurality of data entries to display a stable, reliable trend. In some embodiments, the sloe of the current profile can be averaged across five data entries. This averaging can delay the detection of lockout slightly, but the benefit to the false detection rate can outweigh the minor additional forces that the components can endure during this delay period.

As previously mentioned, there are rare occurrences where the slope can coincidentally fall within the acceptance window. One such instance is attributable to transient load conditions around trigger actuation. Following trigger movement, the current profile exhibits a corresponding current spike. At the peak of this spike, the current settles momentarily before decreasing back to nominal. During these few counts of settling, the change in current occasionally falls within a lockout acceptance range.

In embodiments of lockout module detecting lockout engagement based solely on the current slope or profile, these data points would falsely indicate engagement of a lockout mechanism. Thus, in certain embodiments, the lockout module can be configured to detect a lockout mechanism engagement only upon, a minimum of a plurality of consecutive averages of the current slope falling within the predetermined acceptance range. For example, the lockout module can be configured to detect a lockout mechanism engagement only upon three consecutive averages of the current slope falling within the acceptance range. If the average (of the previous plurality of current slope profiles) is within the lockout acceptance range, the control system stores this average and upon the next data acquisition by the control system (which, in certain embodiments, is 10 ms later), the lockout module will again calculate the average of the previous plurality of current profiles using the new data point (and with the oldest current profile value from the initial plurality of current profiles no longer present in the calculation) and compare this new average to the lockout acceptance range. If three consecutive values fall within the lockout acceptance range, the lockout module can indicate a lockout mechanism has been engaged. If a second or third average does not fall within the acceptance window, the control system can erase any stored averages and continue monitoring for three consecutive current profile adjectives within the predetermined lockout range.

In certain embodiments, the lockout module can be further refined to eliminate transient conditions that could provide false indications of lockout engagement. In certain motor load profiles in the grasping region, current spikes exist which can generate a plurality of consecutive current profile averages within a predetermined acceptance range corresponding to a slope of the current profile empirically determined to be within a lockout engagement region. In certain embodiments, the acceptance range can be between 12 and 40 calculated from a current profile with a current draw measured in mA and an actuator position measured in counts in a potentiometer based position sensing mechanism. In other embodiments, the acceptance range can have a different range based on different computational units or different handle assembly, shaft assembly, or lockout mechanism configurations. Thus, in certain embodiments, in addition to monitoring for lockout engagement upon a plurality of consecutive averages falling within the predetermined lockout acceptance range, the lockout module can compare the final of the plurality of consecutive acceptable averages to the first of the plurality. The lockout module can then indicate a lockout mechanism has been engaged if the final average is greater than the first. With reference to FIG. 56, during engagement of a lockout mechanism, the slope falls within a consistent range but still gradually increases over time. However, current slope averages following a current spike typically decrease over time. Accordingly, the lockout module can be configured to further reduce error in detection of lockout mechanism engagement by assessing whether a plurality of current slope averages is likely to be indicative of a transient current spike.

In light of the above discussion of certain aspects of detecting lockout mechanism engagement in a grasping region, in some embodiments, the control system can include a lockout module configured to consistently distinguish engagement of a lockout mechanism from other transient load conditions on the motor in the grasping region. In certain embodiments, the control system can periodically monitor motor current, actuator position, and elapsed time, and the lockout module can comprise a series of computer processor implementable instructions embodied in software or firmware to calculate whether the current slope profile is indicative of lockout mechanism engagement. In one embodiment, the lockout module can be structured to indicate a lockout has been engaged based on the following criteria:

IF: pwm=max pwm
yn=motor current
$\Delta yn$=slope=change in current=$(yn-yn-1)$
Xn=average of previous $5\Delta y = [(\Delta yn + \Delta yn-1 + \Delta yn-2 + \Delta yn-3 + \Delta yn-4)/5]$
12-40=acceptance range=$12 \leq Xn < 40$
Three consecutive values required=$12 \leq Xn$, $Xn-1$, $Xn-2 < 40$
Last consecutive value must be greater than the first=$Xn > Xn-2$
If the above is TRUE=LOCKOUT ENGAGED While a majority of lockout engagements are detected by a lockout module applying the logical structure above, in certain embodiments, the control system can comprise further refinements to the lockout module to further enhance lockout engagement detection under certain operational conditions. As indicated above, one of the operational conditions for the lockout module is that the monitored pwm of the motor is pwm max, that is, the lockout module is utilized when the trigger is fully depressed and the control system instructs the motor in the handle to operate at full speed.

However, if during a grasping engagement the PLLC's trigger is depressed or released, the motor must transition from stationary to full speed. If the motor was instantly instructed to rotate at full speed, the resulting current spike would be large due to the jump in speed. Instead, the current spike can be minimized by controlling the speed of the motor through a ramp up cycle. This control utilizes pwm, or pulse-width modulation. The pwm governs the percentage of power that the motor receives. If the pwm=100, the motor will operate at full speed. If the pwm=50, the motor will operate at 50% of its max speed. By ramping up the pwm in set intervals following trigger movement, the motor more slowly transitions to full speed and any resulting current spike, although still present, is greatly diminished. In certain embodiments, the ramp up profile of a pwm ramp up in the grasping region takes less than 100 ms to complete, so for the majority of the lockout region (which, in certain embodiments can be transitioned in approximately 1.5 seconds), the lockout module described above is running.

When the pwm is not the max pwm, however, lockout detection by the lockout module can be improved by application of certain corrective sub-modules to account for certain unlikely, but possible usage scenarios. For example, if a user were to pull the trigger just enough to move the actuator within a few position counts of the lockout mechanism and then stop. Upon reengaging the trigger, the user would cause the pwm to ramp up the shaft and jaw assembly would simultaneously physically engage a lockout mechanism. Relying on the lockout module described above during this unstable region would undesirably delay lockout mechanism detection. Instead, in certain embodiments, the lockout module can further comprise a lockout ramp up submodule to more quickly detect engagement of a lockout mechanism in the above usage scenario.

The lockout ramp up submodule can be structured as an end condition to the lockout module. Following an indication by the lockout module that a lockout mechanism is engaged, the lockout ramp up submodule can be run to determine if the pwm is in a current ramping up state, which can be identified by the monitored current increasing across position index counts. If so, the lockout ramp up submodule can apply an additional assessment before the lockout module can indicate a lockout mechanism has been engaged. Advantageously, this lockout ramp up submodule can reduce the risk of false lockout mechanism detection due to transient user trigger inputs. For example, in addition to the use scenario described above, if a user deliberately and repeatedly depresses and releases the trigger slight amounts, the trigger oscillates and the current follows suit. If the user continues to wiggle the trigger in this manner, the current can eventually coincide with the lockout acceptance range, including within the consecutive averages required for the lockout module to indicate a lockout mechanism has been engaged. This trigger oscillation usage scenario requires deliberate action beyond normal hand tremors, but the ramp up submodule can be configured to identify whether a particular monitored current profile is due to engagement of a lockout mechanism or trigger oscillation.

Where the lockout ramp up submodule has been initiated (after the lockout module would indicate a lockout mechanism is present and the pwm was assessed to be in a ramping up state), the lockout ramp up submodule compares the monitored current to a calculated threshold value. This current threshold ensures that the current is above nominal, thus signifying that the motor is being loaded by engagement of a lockout mechanism. To calculate the current threshold that needs to be overcome, the submodule assesses a first instance of pwm=max pwm thus far. This current value can be stored by the control system as a current baseline, and resets whenever the trigger is fully released and the jaws return to their open position. If the trigger is depressed incrementally, only the first instance of pwm=max pwm is saved as the current baseline. This baseline provides a reference for the expected current value at that point given the specific motor, drivetrain components, and batteries, in the handle. This initial value can be stored as the current baseline as there is no risk in lockout occurring prior as drivetrain travel has been minimal so far, and the lockout mechanism is still relatively far away.

A position-dependent current correction value is added to the current baseline to establish the current threshold. This current correction value accounts for the increase in nominal current with position due to clamping and tissue compression occurring later on within the grasping region. Position based current correction values can be empirically determined for a given elongate shaft and lockout mechanism assembly by plotting the max nominal current values at the ideal lockout locations and calculating the linear equation connecting them. These predetermined current correction values can then be stored for use by the lockout ramp up submodule in assessing the presence of a lockout mechanism engagement.

In operation of the lockout ramp up submodule, once the current threshold is established, the monitored current is compared and if it exceeds the threshold, then the lockout ramp up submodule indicates that a lockout mechanism is engaged. In certain embodiments, the lockout ramp up submodule can be embodied in a software or firmware program operating according to the following logical structure:

IF: Lockout Module=TRUE
IF: pwm≠max pwm (ramping up)
$y_n$=motor current
$y_b$=current baseline=y at first instance of max pwm
$y_{ths}$=current threshold=current baseline+[(5*position)−200]
Current must exceed current threshold=$y_n$>$y_{ths}$
If the above is TRUE=LOCKOUT ENGAGEMENT In certain embodiments, the lockout module of the control system can comprise a lockout transition submodule to further improve lockout mechanism detection by the lockout module. The lockout transition submodule can activate at the peak of the pwm ramp up. When the motor finally reaches maximum speed (pwm=max pwm) following trigger movement and a current spike, the current settles and stabilizes and can often experience a slight dip. If during a stapler usage scenario a lockout mechanism is engaged as the current is settling from reaching max speed, the lockout module can fail to indicate a lockout mechanism is engaged. In such a scenario, the final current average is lower than the first current average. To prevent this false negative, in certain embodiments, the lockout transition submodule is run during the first instance of pwm=max pwm for each ramp up.

The lockout transition submodule can further enhance lockout mechanism detection in the event of a current dip by taking an additional average. The lockout transition submodule can be activated during the transition from ramp up to max pwm. In operation, the lockout transition submodule averages the previous three averages (each average representing the previous five changes in current) to create a more stable data point. Instead of comparing the initial averages to an acceptance range, lockout transition submodule compares a second obtained average to a separate acceptance window. As this submodule is activated only once for each ramp up, it cannot wait for consecutive values and therefore only that single second average value will be analyzed. If the second average falls within the acceptance range (which was empirically determined for a particular stapler configuration), the next step is to calculate the current threshold using the same current threshold computation as in the lockout ramp up submodule. Once the current threshold is established, the monitored current is compared to the current threshold and if it exceeds the threshold, then the lockout transition submodule indicates a lockout mechanism is engaged.

In certain embodiments, the lockout transition submodule can be embodied in a software or firmware program operating according to the following logical structure:
IF: Lockout Module=FALSE
IF: pwm=max pwm (first instance per ramp up)
yn=motor current
$\Delta yn$=slope=change in current=$(yn-yn-1)$
Xn=average of previous $5\Delta y$=$[(\Delta yn+\Delta yn-1+\Delta yn-2+\Delta yn-3+\Delta yn-4)/5]$
Zn=average of previous 3X=$(Xn+Xn-1+Xn-2)/3$
15-40=acceptance range=$15<Zn<40$
yb=current baseline=y at first instance of max pwm
yths=current threshold=current baseline+$[(5*position)-225]$
Current must exceed current threshold=$yn>yths$
If the above is TRUE=LOCKOUT ENGAGED In certain embodiments, the lockout module can further comprise a lockout post transition submodule that is activated for a predetermined actuation shaft movement range following the lockout transition submodule. In one embodiment, the lockout post transition submodule is activated in the 10 counts following the lockout transition submodule. Once the current has settled from a transition to pwm max, it can oscillate and experience slight dips and gains in quick succession. If a lockout mechanism is engaged, however, the current will steadily increase throughout this post transition or 10 count window. With the transient, oscillatory current draw conditions during the post-transition period, the lockout module can take several counts to indicate the presence of an engaged lockout mechanism due to the necessity for several counts of a trend to influence the calculated averages. Thus, performance of the lockout module can be enhanced, and wear on the device can be reduced through activation of the lockout post-transition submodule following the lockout transition submodule. The lockout post transition submodule activates for a predetermined displacement following the lockout transition module and compares a change in monitored current to the previous index's change in current to see if there is an upwards trend for a predetermined measuring period. In certain embodiments, if the change is current is increasing three consecutive times, then the lockout post transition submodule indicates a lockout mechanism is engaged.

In certain embodiments, the lockout post transition submodule can be embodied in a software or firmware program operating according to the following logical structure:
IF: Lockout Module=FALSE
IF: Transition Submodule=FALSE
IF: within 10 counts following max pwm transition
yn=motor current
$\Delta yn$=slope=change in current=$(yn-yn-1)$
Change in current increasing=$\Delta yn>\Delta yn-1$
Three consecutive values required=$\Delta yn>\Delta yn-1>\Delta yn-2>\Delta yn-3$
If the above is TRUE=LOCKOUT ENGAGED The lockout module can further comprise a lockout ramp down submodule to improve lockout mechanism detection during a pwm ramp down of the motor drive from the control system. In certain embodiments, the lockout ramp down submodule activates during a pwm ramp down, which occurs anytime the control system directs the motor to slow down or stop. Just as the control system directs motor via a pwm ramp up to avoid current spikes, the pwm ramps down when the trigger is released or the actuator reaches a position proportional to the trigger position in the grasping region. As the pwm ramps down, the current is expected to similarly decrease due to the lessened power requirements. The lockout ramp down submodule verifies that the current decreasing as expected during a pwm ramp down event. The lockout ramp down submodule can compare the change in current to a zero state. If the change in current is greater than zero over several consecutive measurements, the lockout ramp down submodule indicates that a lockout mechanism is engaged. In certain embodiments, the lockout ramp down submodule compares the change in current to a zero state over three measurement periods.

In certain embodiments, the lockout ramp down submodule can be embodied in a software or firmware program operating according to the following logical structure:
IF: Lockout Module=FALSE
IF: Transition Submodule=FALSE
IF: Post-Transition Submodule=FALSE
IF: pwm≠max pwm (ramping down)
yn=motor current
$\Delta yn$=slope=change in current=$(yn-yn-1)$
Change in current increasing=$\Delta yn>0$
Three consecutive values required=$\Delta yn, \Delta yn-1, \Delta yn-2>0$
If the above is TRUE=LOCKOUT ENGAGED With reference to FIG. 61, an exemplary flow chart for a lockout module including various submodules is illustrated. In the illustrated embodiment, as the control system refreshes current and position monitoring (in certain embodiments, every 10 ms), the handle reads the actuation shaft position potentiometer to determine if it is still within the lockout region. If the actuator is in the lockout region, the control system of the handle assembly performs the lockout module 630. If the lockout module indicates a lockout mechanism is engaged, the control system determines if the lockout ramp up submodule 632 is applicable and if so, performs it. If the ramp up submodule 632 is not applicable, the control system indicates that a lockout mechanism is engaged and depowers the motor. If the ramp up submodule 632 is applicable and indicates a lockout mechanism is engaged, the control system indicates a lockout mechanism is engaged and depowers the motor. If the ramp up submodule 632 is applicable and fails to find a lockout mechanism engaged, the lockout module 630 ends and waits 10 ms to restart. If the lockout module 630 fails to find a lockout mechanism engaged, the control system assesses the transition submodule 634, then the post-transition submodule 636, and finally the ramp down submodule 638.

In certain embodiments, if the lockout module and various submodules of the control system fails to indicate the presence of a lockout mechanism engagement, the control system can erase any stored X and Z variables (averages) used in the lockout module. If the control system resets the lockout module because there have not been three consecutive passes yet (but the current attempt did pass), then the handle retains the variable values. The current baseline is also retained until the handle is completely reset to jaws open position.

Motor Polarity Verification Module

In some embodiments, the control system can include a polarity verification module to assess and correct a direction of travel of the DC motor. During stapler handle assembly manufacture, it is possible for a DC motor to be installed in a reverse-polarity orientation. Certain handle assembly and testing procedures can be implemented to significantly reduce the incidence of reversed motor polarity. However, these procedures can be time intensive and add to production expenses. If a motor is inadvertently installed in a reversed-polarity orientation the stapler will not function as intended in response to user input. To reduce the impact of a reverse-polarity motor installation, in certain embodiments the control system can comprise a motor polarity verification module configured to monitor actuator position upon application of power to the DC motor. Thus, advantageously, the motor polarity verification module can increase handle assembly production efficiency and reduce costs as polarity verification procedures can be removed from handle assembly production. The polarity verification module can include a default polarity assumption that a particular motor polarity will result in a particular direction of actuation. The polarity verification module can then apply power to the motor with a known polarity and monitor the change in position of the actuator.

Figure 62:
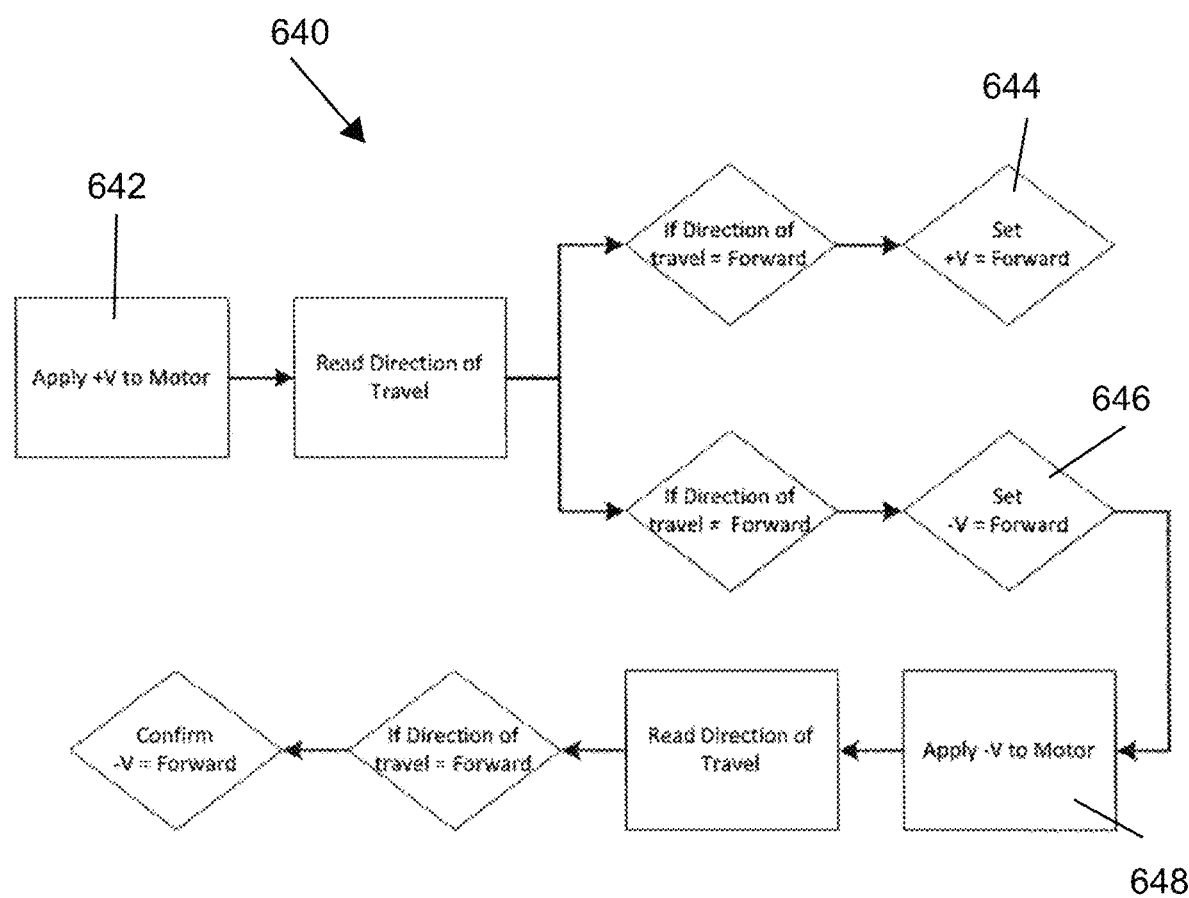
FIG. 62 is an motor polarity verification logical structure for an embodiment of powered handle assembly.

FIG. 62 illustrates an exemplary logical flow structure of a motor polarity verification module 640 that can be incorporated into the control system of the handle assembly. After the application of power to the motor 642, if the actuator position has changed consistently with the default polarity assumption, then the motor drive logic of the control system remains unaltered 644. If, after the application of power to the motor 642, the actuator position has changed position in a direction opposite that of the default polarity assumption, then the motor drive logic of the control system is revised to reverse the polarity of power 646 to be applied in grasping, stapling, and return operations. In certain embodiments, where polarity is reversed by the polarity verification module, following the reversal of polarity, the polarity verification module can be configured to retest the direction of travel by applying power to the motor at the reversed polarity 648 and verifying that the direction of travel of the actuation shaft is forward.

Removable Data Log

As can be appreciated, with the operation of the control system in one or more grasping, firing, and retraction operations of a surgical stapler, a variety of data regarding motor current draw, motor speed, power, torque, lockout actuation, number of reload cartridges fired, battery life, and the like can be stored on a memory device such as a solid state memory module positioned within the handle assembly. It can be desirable to retrieve and analyze this data. In some embodiments, the data can be retrieved by electronically coupling to the handle assembly via wired or wireless communications protocol. However, since the handle assembly is a surgical device, there can be logistical challenges associated with accessing previously-used handle assembly to retrieve the data. Accordingly, in certain embodiments, the surgical stapler handle assembly can comprise a removable memory module that can be removed from the handle assembly upon completion of a surgical procedure.

With reference to FIGS. 63 and 64A-64B, in certain embodiments, the power source or battery pack 650 can comprise a removable memory module 652. In the illustrated embodiment, the battery pack comprises an electrically coupled printed circuit board assembly (PCBA) including the memory module 652. The PCBA can be connected through a communication interface with the microprocessor for read write access of operational data parameters of the handle assembly with the memory module 652. The PCBA can further comprise a data interface surface such as electrical contact pads disposed thereon. In use, upon completion of a surgical procedure, a user can remove the battery pack 650 from the handle assembly and remove the PCBA including the memory module 652 form the battery pack 650. In some embodiments, the PCBA can be coupled to the battery pack 650 by a removable pull-tab to facilitate rapid decoupling of the memory module 652. In other embodiments, the memory module 652 can be removable from the battery pack through use of a dedicated removal tool or other hand tool. Upon removal of the memory module 652, the stapler and battery pack can be processed appropriately as medical waste.

With continued reference to FIGS. 63 and 64A-64B, in certain embodiments, the battery pack 650 can further comprise a battery discharge circuit 654 electronically coupled to the memory module 652 and one or more battery cells 656. As illustrated, upon removal of the memory module form the battery pack, the discharge circuit 654 housed within the battery pack 650 drains the battery to reduce electrical or fire hazards presented by a potential short of battery terminals following disposal. In certain embodiments, the battery discharge circuit 654 can comprise a discharge resistor configured to drain the battery upon removal of the memory module.

Figure 65:
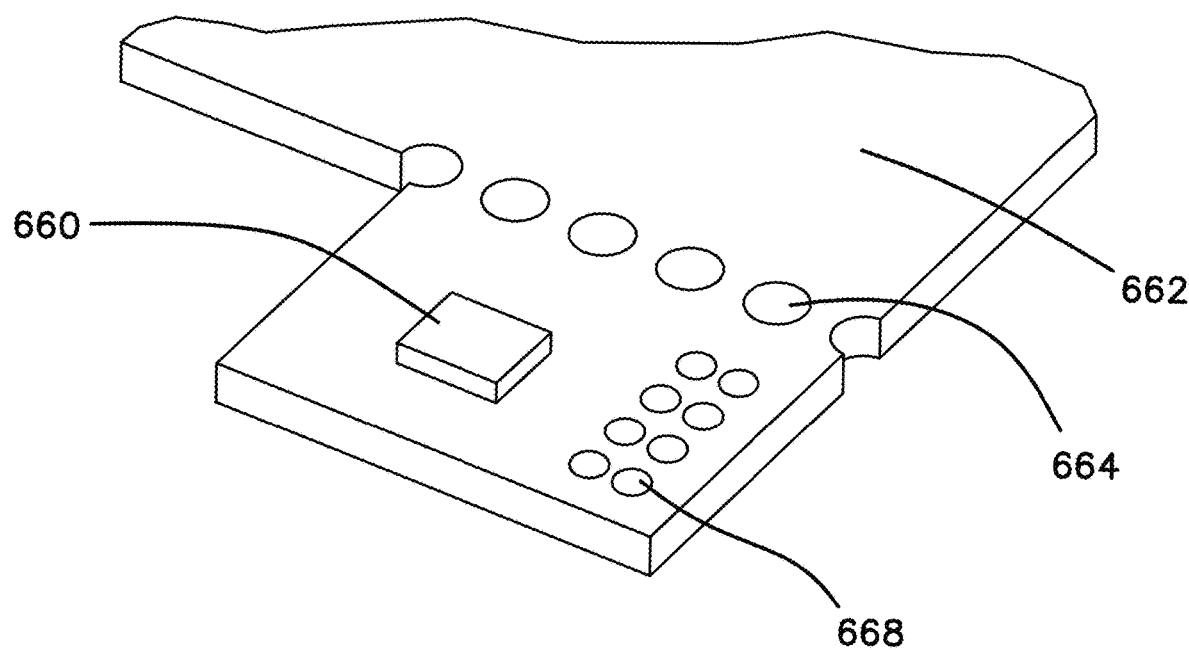
FIG. 65 is a perspective view of another embodiment of removable memory module for certain embodiments of powered handle assembly.

With reference to FIG. 65, in certain embodiments, a removable memory module 660 can be positioned on a removable section of the PCB. As illustrated, the removable section of the PCB can be joined to the PCB by a breakaway or perforated section 664 such that a user can rapidly detach the memory module 660 from the PCB 662. The removable section of the PCB can further comprise an electronic interface surface 668 such as a plurality of contact pads electrically coupled to the memory module 660.

Figure 66:
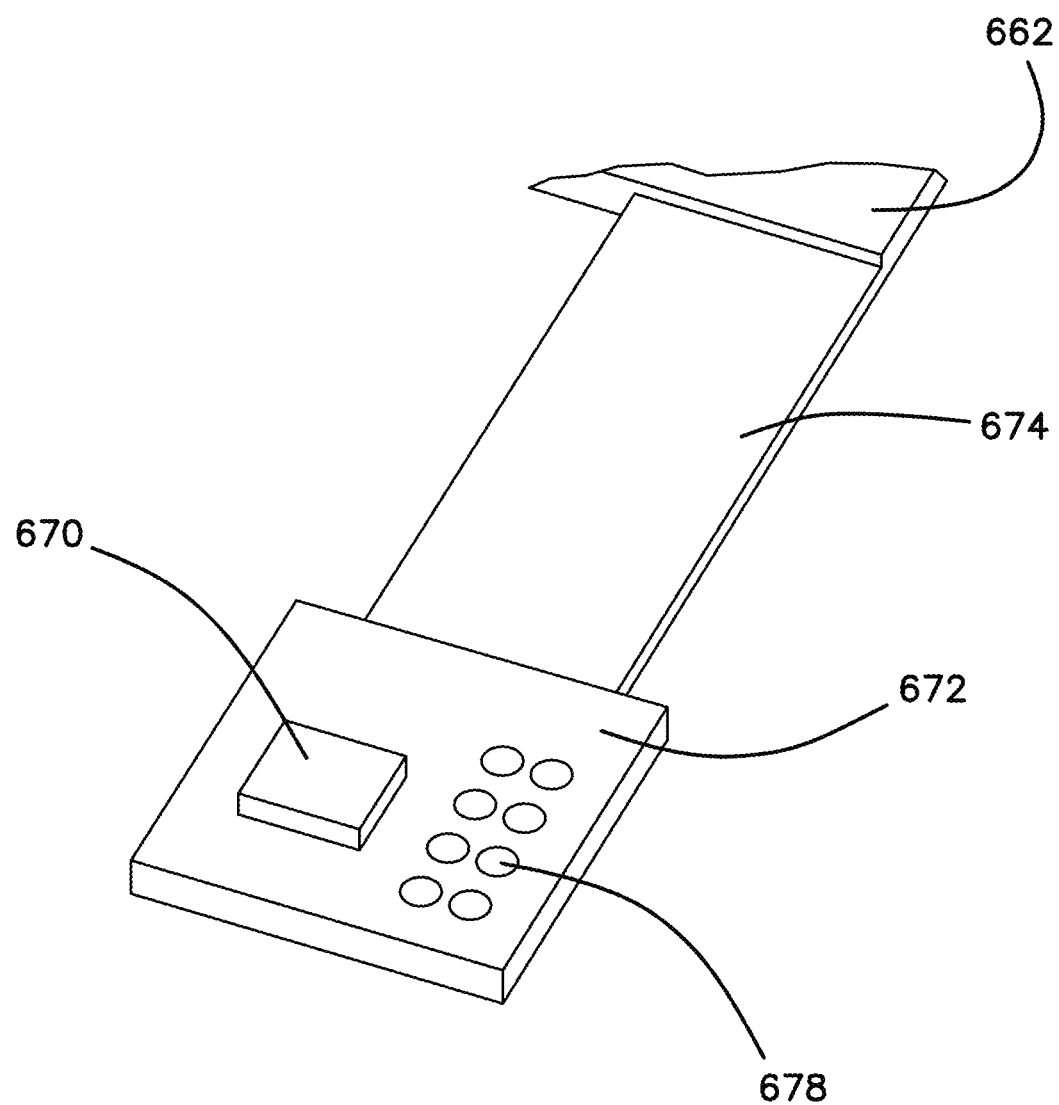
FIG. 66 is a perspective view of another embodiment of removable memory module for certain embodiments of powered handle assembly.

With reference to FIG. 66, in certain embodiments, a removable memory module 670 can be coupled to a main printed circuit board 662 (PCB) within the handle assembly by a connector that can be selected to be easily cut with scissors or other readily available implements. In the illustrated embodiment, the memory module is positioned on a memory PCB 672 that is electronically coupled to the main PCB 662 by a flexible PCB 674. After a use of the handle assembly, the user can cut the flexible PCB 674 and remove the memory module 670 and memory PCB 672. The memory PCB 672 can further comprise an electronic interface surface 678 such as a plurality of contact pads electrically coupled to the memory module 670.

The memory modules described herein can be positioned in the handle assembly to prevent inadvertent access to the memory module during operation of the handle assembly, but provide access to the memory module upon completion of a handle assembly. For example, as described with reference to FIGS. 63 and 64A-64B, in certain embodiments, the memory module can be housed within a battery pack or battery compartment of the handle assembly such that it can be removed upon removal of the battery. In other embodiments, the memory module can be positioned behind a dedicated access panel on the handle assembly. In certain embodiments, the dedicated access panel can require a dedicated tool or key to open. In other embodiments, the memory module can be accessible upon operation of a manual override return system such as that described with reference to FIGS. 21-31.

Although this application discloses certain preferred embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above, but should be determined only by a fair reading of the claims which follow.

What is claimed is:

1. A handle assembly for a surgical stapler, the handle assembly comprising:
   a handle body, the handle body comprising a stationary handle and a trigger pivotably coupled to the handle body;
   an electric motor disposed within the handle body;
   a control system disposed within the handle body and coupled to the electric motor, wherein the control system is configured to control an operation of the electric motor;
   an actuation shaft having a distal end and a proximal end, wherein the actuation shaft is slidable within the handle body along a longitudinal axis; and
   a lockout mechanism that is operably coupled to the distal end of the actuation shaft, wherein the lockout mechanism has at least one notch corresponding to a lockout region,
   wherein the control system comprises computer-readable memory that configures the control system to:
   monitor a position of the actuation shaft,
   monitor a current draw from the electric motor,
   calculate a rate of change of the current draw from the electric motor, and
   adjust an operation of the electric motor based on the monitored position and the calculated rate of change of the current draw, wherein the electric motor is depowered when the position of the actuation shaft is at a predetermined location and the calculated rate of change of the current draw is equal to or exceeds a predetermined threshold, and
   wherein a lockout condition associated with the lockout mechanism is detected after calculating the rate of change of the current draw a pre-determined number of times consecutively, and wherein an average of each of the consecutively calculated rate of changes of the current draw fall within a predetermined range.

2. The handle of claim 1 further comprising a battery supply, and wherein the control system further monitors a remaining battery life of the battery supply to further adjust the operation of the electric motor based on the monitored remaining battery life.

3. The handle of claim 1, wherein the monitoring of the position of the actuation shaft is with respect to the at least one notch associated with the lockout region, and wherein the at least one notch corresponds to the predetermined location.

4. The handle of claim 1 further comprising a dedicated haptic feedback generator that generates feedback for a user regarding a status of the electric motor.

5. The handle of claim 1, wherein the actuation shaft comprises a rack formed near a proximal end of the actuation shaft, the rack configured to engage with the electric motor to facilitate in the sliding of the actuation shaft along the longitudinal axis within the handle body.

6. The handle assembly of claim 1, wherein the rate of change of the current draw from the electric motor is calculated using a pre-determined number of consecutive measurements.

7. The handle assembly of claim 1, wherein the monitoring of the current draw from the electric motor comprises detecting whether the current draw exceeds a pre-determined current threshold.

8. The handle assembly of claim 1, wherein the monitoring of the current draw from the electric motor comprises monitoring the current draw with respect to one or more current thresholds, and wherein at least one of the one or more current thresholds is dependent on the position of the actuation shaft.

9. The handle assembly of claim 1, wherein the computer-readable memory is removable from the surgical stapler upon completion of a surgical procedure.

10. The handle assembly of claim 1, wherein the computer-readable memory further configures the control system to generate a feedback for the user regarding a status of the surgical stapler based on the detecting of the lockout condition, and wherein the feedback that is generated comprises at least one of a color-based feedback indicia or haptic feedback.

11. The handle assembly of claim 1, wherein the computer-readable memory configures the control system to further detect the lockout condition for the electric motor when the current draw from the electric motor exceeds a predetermined current threshold while the electric motor is in a duty cycle ramp up.

12. The handle assembly of claim 1, wherein the computer-readable memory configures the control system to further detect the lockout condition for the electric motor when a power system driving the electric motor is in a transition period after a duty cycle ramp up.

13. The handle assembly of claim 12, wherein the computer-readable memory configures the control system to further detect the lockout condition for the electric motor in a duty cycle ramp down where the current draw from the electric motor does not decrease over a plurality of consecutive monitored events.

14. The handle assembly of claim 1, wherein the computer-readable memory configures the control system to further detect the lockout condition for the electric motor when the electric motor is driven over a predetermined range of actuation shaft positions following the transition period after a duty cycle ramp up.

15. The handle assembly of claim 1, wherein the computer-readable memory configures the control system to further detect the lockout condition for the electric motor based on detecting the current draw from the electric motor at a predetermined position of the actuation shaft.

\* \* \* \* \*